US010233229B2

(12) United States Patent
Ishino et al.

(10) Patent No.: US 10,233,229 B2
(45) **Date of Patent: *Mar. 19, 2019**

(54) ENGINEERED MONOMERIC ANTIBODY FRAGMENTS

(71) Applicant: Pfizer Inc., New York, NY (US)

(72) Inventors: Tetsuya Ishino, Izumo (JP); Weili Duan, North Reading, MA (US); Ronald William Kriz, Northborough, MA (US)

(73) Assignee: Pfizer Inc., New York, NY (US)

( * ) Notice: Subject to any disclaimer, the term of this patent is extended or adjusted under 35 U.S.C. 154(b) by 533 days.

This patent is subject to a terminal disclaimer.

(21) Appl. No.: 14/650,188

(22) PCT Filed: Nov. 25, 2013

(86) PCT No.: PCT/IB2013/060384

§ 371 (c)(1),
(2) Date: Jun. 5, 2015

(87) PCT Pub. No.: WO2014/087299

PCT Pub. Date: Jun. 12, 2014

(65) Prior Publication Data

US 2015/0322135 A1 Nov. 12, 2015

Related U.S. Application Data

(60) Provisional application No. 61/734,841, filed on Dec. 7, 2012.

(51) Int. Cl.

| | |
|---|---|
| ***C07K 1/00*** | (2006.01) |
| ***C07K 16/00*** | (2006.01) |
| ***C12P 21/08*** | (2006.01) |
| ***C07H 21/04*** | (2006.01) |
| ***C12P 21/06*** | (2006.01) |
| ***C12P 21/04*** | (2006.01) |
| ***C12N 5/00*** | (2006.01) |

(52) U.S. Cl.

CPC .......... *C07K 16/00* (2013.01); *C07K 2299/00* (2013.01); *C07K 2317/41* (2013.01); *C07K 2317/524* (2013.01); *C07K 2317/526* (2013.01); *C07K 2317/55* (2013.01); *C07K 2317/64* (2013.01); *C07K 2317/94* (2013.01)

(58) Field of Classification Search

None

See application file for complete search history.

(56) References Cited

U.S. PATENT DOCUMENTS

| | | | | |
|---|---|---|---|---|
| 7,393,662 B2 * | 7/2008 | Heavner | .............. | C07K 14/505 424/178.1 |
| 2006/0074225 A1 | 4/2006 | Chamberlain et al. | | |
| 2006/0247425 A1 | 11/2006 | Chung et al. | | |

FOREIGN PATENT DOCUMENTS

| | | |
|---|---|---|
| WO | 2006031994 | 3/2006 |
| WO | 2007059782 | 5/2007 |
| WO | 2008145139 | 12/2008 |
| WO | 2011005621 | 1/2011 |
| WO | 2011059684 | 5/2011 |
| WO | 2011063348 | 5/2011 |

OTHER PUBLICATIONS

Vitetta et al. Science 2006 313:308-309. (Year: 2006).*

Ishino, Tetsuya et al: "Engineering a Monomeric Fc Domain Modality by N-Giycosylation for the Half-life Extension of Biotherapeutics", Journal of Biological Chemistry,vol. 288, No. 23, Apr. 24, 2013, pp. 16529-16537.

T. Ying et al: "Soluble Monomeric IgG1 Fc", Journal of Biological Chemistry, vol. 287, No. 23, Jun. 1, 2012, pp. 19399-19408.

Database Geneseq [Online] Feb. 17, 2011, "Human IgG1 Fc mutant protein (S160N).", retrieved from EBI accession No. GSP:AYN30516, Database accession No. AYN30516.

International Search Report and Written Opinion; International No. PCT/IB2013/060384, dated Jun. 12, 2015, 14 pages.

Prat et al. "Agonistic monoclonal antibodies against the Met receptor dissect the biological responses to HGF." J. of Cell Science; vol. 111, 237-247; (1998).

Lobo et al. "Antibody Pharmacokinetics and Pharmacodynamics." J. of Pharmaceutical Sciences, vol. 93, No. 11, (2004).

* cited by examiner

*Primary Examiner* — Chun W Dahle

(57) ABSTRACT

The present invention relates to monomeric polypeptides comprising an engineered monomeric antibody fragment (e.g., monomeric Fc-containing polypeptides) wherein the monomeric Fc comprises one or more engineered N-linked glycosylation sites in the CH3-CH3 dimerization interface. Methods for producing such engineered monomeric antibody fragments and their use in diagnostics and therapeutics are also provided.

21 Claims, 6 Drawing Sheets

Specification includes a Sequence Listing.

$C_H3$-$C_H3$ interface $C_H2$-$C_H2$ interface

FIG. 2

```
      344*                 * * *                      *
hIgG1 REPQVYTLPPSRDELTKNQVSLTCLVKGFYPSDIAVEWESNGQPENNYKTTP
hIgG2 REPQVYTLPPSREEMTKNQVSLTCLVKGFYPSDISVEWESNGQPENNYKTTP
hIgG3 REPQVYTLPPSREEMTKNQVSLTCLVKGFYPSDIAVEWESSGQPENNYNTTP
hIgG4 REPQVYTLPPSQEEMTKNQVSLTCLVKGFYPSDIAVEWESNGQPENNYKTTP
mIgG1 KAPQVYTIPPPKEQMAKDKVSLTCMITDFFPEDITVEWQWNGQPAENYKNTQ
mIG2A RAPQVYVLPPPEEEMTKKQVTLTCMVTDFMPEDIYVEWTNNGKTELNYKNTE
mIG2B RAPQVYILPPPAEQLSRKDVSLTCLVVGFNPGDISVEWTSNGHTEENYKDTA
mIgG3 QTPQVYTIPPPREQMSKKKVSLTCLVTNFFSEAISVEWERNGELEQDYKNTP

      396  *   * * *
hIgG1 PVLDSDGSFFLYSKLTVDKSRWQQGNVFSCSVMHEALHNHYTQKSLSLSPGK
hIgG2 PMLDSDGSFFLYSKLTVDKSRWQQGNVFSCSVMHEALHNHYTQKSLSLSPGK
hIgG3 PMLDSDGSFFLYSKLTVDKSRWQQGNIFSCSVMHEALHNRFTQKSLSLSPGK
hIgG4 PVLDSDGSFFLYSRLTVDKSRWQEGNVFSCSVMHEALHNHYTQKSLSLSLGK
mIgG1 PIMNTNGSYFVYSKLNVQKSNWEAGNTFTCSVLHEGLHNHHTEKSLSHSPGK
mIG2A PVLDSDGSYFMYSKLRVEKKNWVERNSYSCSVVHEGLHNHHTTKSFSRTPGK
mIG2B PVLDSDGSYFIYSKLNMKTSKWEKTDSFSCNVRHEGLKNYYLKKTISRSPGK
mIgG3 PILDSDGTYFLYSKLTVDTDSWLQGEIFTCSVVHEALHNHHTQKNLSRSPGK
```

FIG. 3

```
        236                             *                                 *
hIgG1   GGPSVFLFPPKPKDTLMISRTPEVTCVVVDVSHEDPEVKFNWYVDGVEVHNAKT
hIgG2   AGPSVFLFPPKPKDTLMISRTPEVTCVVVDVSHEDPEVQFNWYVDGVEVHNAKT
hIgG3   GGPSVFLFPPKPKDTLMISRTPEVTCVVVDVSHEDPEVQFKWYVDGVEVHNAKT
hIgG4   GGPSVFLFPPKPKDTLMISRTPEVTCVVVDVSQEDPEVQFNWYVDGVEVHNAKT
mIgG1   EVSSVFIFPPKPKDVLTITLTPKVTCVVVDISKDDPEVQFSWFVDDVEVHTAQT
mIG2A   GGPSVFIFPPKIKDVLMISLSPIVTCVVVDVSEDDPDVQISWFVNNVEVHTAQT
mIG2B   GGPSVFIFPPNIKDVLMISLTPKVTCVVVDVSEDDPDVQISWFVNNVEVHTAQT
mIgG3   GGPSVFIFPPKPKDALMISLTPKVTCVVVDVSEDDPDVHVSWFVDNKEVHTAWT

        290                 *  *
hIgG1   KPREEQYNSTYRVVSVLTVLHQDWLNGKEYKCKVSNKALPAPIEKTISKAKGQP
hIgG2   KPREEQFNSTFRVVSVLTVVHQDWLNGKEYKCKVSNKGLPAPIEKTISKTKGQP
hIgG3   KPREEQYNSTFRVVSV LTVLHQDWLNGKEYKCKVSNKALPAPIEKTISKTKGQP
hIgG4   KPREEQFNSTYRVVSVLTVLHQDWLNGKEYKCKVSNKGLPSSIEKTISKAKGQP
mIgG1   QPREEQFNSTFRSVSELPIMHQDWLNGKEFKCRVNSAAFPAPIEKTISKTKGRP
mIG2A   QTHREDYNSTLRVVSALPIQHQDWMSGKEFKCKVNNKDLPAPIERTISKPKGSV
mIG2B   QTHREDYNSTIRVVSTLPIQHQD WMSGKEFKCKVNNKDLPSPIERTISKIKGLV
mIgG3   QPREAQYNSTFRVVSALPIQHQDWMRGKEFKCKVNNKALPAPIERTISKPKGRA
```

ENGINEERED MONOMERIC ANTIBODY FRAGMENTS

CROSS-REFERENCE TO RELATED APPLICATIONS

This application is the U.S. National Phase of International Application No. PCT/IB2013/060384, filed Nov. 25, 2013 and published in English, which claims the benefit of U.S. provisional application No. 61/734,841, filed Dec. 7, 2012, the complete contents of both hereby incorporated herein by reference for all purposes.

REFERENCE TO SEQUENCE LISTING

This application contains a Sequence Listing which has been submitted electronically in ASCII format and is hereby incorporated by reference in its entirety. Said ASCII copy, created on Jun. 4, 2105, is named PC71962A SEQUENCE PROJECT FILE_ST25.txt and is 177,573 bytes in size.

FIELD

The present invention relates to engineered monomeric antibody fragments (e.g., monomeric Fc-containing polypeptides) comprising one or more engineered N-linked glycosylation sites in the CH3-CH3 dimerization interface. The invention also relates to methods for making such engineered monomeric antibody fragments and their use in diagnostics and therapeutics.

BACKGROUND

Antibodies and Fc-fusion biologics have been used as therapeutic molecules for the treatment of various diseases in the past decade. Most antibodies on the market are full length antibodies (e.g., IgGs) because their long half-lives allow for less frequent dosing in patients. See, e.g., Lobo et al., *J. Pharm. Sci.* 93, 2645-2668 (2004). A full-length IgG is composed of two identical Fab fragments which are connected by the dimeric form of Fc fragments through two identical hinge regions. While the Fab region is responsible for targeting the antigen, the Fc region of IgG has been implicated in the antibody's prolonged survival time in serum via the neonatal Fc receptor (FcRn) recycling pathway. See, e.g., Brambell et al., *Nature* 203, 1352-1354 (1964) and Raghavan et al., *Biochemistry* 34, 14649-14657 (1995). The intrinsic association constant for monovalent binding by each Fab is usually referred to as the affinity of the antibody, while the bivalent binding ability of two Fabs in an intact IgG antibody is referred to as the avidity of the antibody. In some cases, the apparent equilibrium binding due to the avidity of IgG can be increased up to 100-fold compared with the affinity of the Fab. See, e.g., Ways et al., *Biochem J* 216, 423-432 (1983). For therapeutic purposes, however, the bivalency of IgG might not always be necessary or desired. For example, a therapeutic IgG would not take advantage of avidity if the targets are monomeric soluble molecules. Additionally, if the targets are multimeric soluble molecules, the dimeric nature of IgG can result in formation of a cross-linked network in plasma leading to formation of aggregates. See, e.g., Marrack, *Annu. Rev. Microbiol.* 9, 369-386 (1955). Furthermore, when the targets to be antagonized are on a cell-surface, binding of two cell surface targets by a single IgG may result in unwanted agonist activity via cross-linking or bringing together of the two molecules by the antibody. See, e.g., Prat et al., *J. Cell. Sci.* 111 9Pt2), 237-247 (1998). In addition, some full-size IgGs also exhibit poor penetration into tissues, especially solid tumors, and poor or absent binding to regions of some antigens that are occluded and can only be accessed by molecules of smaller size. See, Ying et al., *J. Biol. Chem.* (2012). Accordingly, in order to overcome the potential drawbacks associated with the bivalency of therapeutic antibodies and dimeric Fc fusion proteins, "one-armed" antibody, "one-armed" Fc fusion proteins, or a variety of antibody fragments of smaller size, have been recently explored for various therapeutic targets in order to improve a biological activity, bioavailability, and/or pharmacokinetics of therapeutic molecules. See, e.g., Demignot et al., *Cancer Res.* 50, 2936-2942 (1990), and Dumont et al., *BioDrugs* 20, 151-160 (2006). Thus, monomeric immunoglobulin Fc molecules, monovalent antibodies, and antibody Fc molecules have been described. See, e.g., US2006/0074225, WO2007/059782, WO2008/145139, WO2011/005621, and WO2011/063348. Despite the recognition that monomeric forms of antibodies and Fc molecules, and proteins comprising them, would provide certain advantages in development of therapeutic molecules, there remains a long-felt need for monomeric antibodies and fusion proteins which are stable but which do not exhibit increased immunogenicity or suffer from other drawbacks of the protein engineering required to achieve stable monomeric proteins.

N-glycosylation can have an impact on the protein stability, susceptibility to protease and immunogenicity as well as on the in vivo bioactivity of therapeutic proteins. See, e.g., Sola et al., *J. Pharm. Sci.* 98, 1223-1245 (2009), and Elliott et al., *Nature Biotechnology* 21, 414-421 (2003). Asparagine-linked glycosylation (Asn-linked or N-linked glycosylation) is one of the most common forms of post-translational modification of proteins in eukaryotic organisms. In general, the modification occurs at an asparagine residue in the first position of the consensus sequence of Asn-X-Ser/Thr, where the second position, "X", is any amino acid except proline and wherein the third position is either serine or threonine such that Asn-X-Ser and Asn-X-Thr are considered canonical potential glycosylation sites in mammalian proteins. Shakin-Eshleman et al., *J. Biol. Chem.* 271, 6363-6366 (1996). Native human IgG antibodies have an N-glycan at $Asn^{297}$ on the CH2 region of Fc domain. Crystal structures of the Fc domains have also revealed that the carbohydrates are packed within the internal space enclosed by the CH2 domain. While CH2 domains from two polypeptide chains make no direct interactions due to the carbohydrate moieties, the CH3 domains associate with each other through a large hydrophobic interface. Accordingly, it would be desirable to generate a stable monomeric form of a Fc domain with a prolonged in vivo half-life and other improved pharmacokinetics using the N-glycosylation engineering approach, in which the engineered glycan not only can separate the CH3-CH3 interface, but also can cover the exposed hydrophobic surface of CH3 domain to avoid aggregation and potential immunogenicity. The present invention fulfills this need.

SUMMARY

The invention disclosed herein is directed to a monomeric antibody fragment (e.g., monomeric Fc-containing polypeptide) comprising one or more engineered N-linked glycosylation sites in the CH3-CH3 dimerization interface or both the CH3-CH3 dimerization interface and the CH2-CH2 interface. In one aspect, the invention provides a monomeric Fc-containing polypeptide comprising an IgG CH2 and an IgG CH3 domain, wherein the CH3 domain comprises one or more engineered N-linked glycosylation sites in the CH3-CH3 dimerization interface, wherein the engineered N-linked glycosylation site comprises at least one, more preferably, two amino acid modifications having a consensus sequence of Asn-X-Ser or Asn-X-Thr, and wherein X is any amino acid except Pro.

In one variation, the invention provides a polypeptide comprising at least two recombinantly linked monomeric Fc-containing polypeptides as described herein, wherein each Fc-containing polypeptide has the same or different engineered N-linked glycosylation sites in the CH3-CH3 dimerization interface. In some embodiments, each Fc-containing polypeptide has the same engineered N-linked glycosylation sites in each CH3-CH3 dimerization interface, and further wherein the engineered N-linked glycosylation sites are S364N-X-T366 and Y407N-X-K409T. In some embodiments, the amino acid modifications in the CH3-CH3 dimerization interface are selected from the group consisting of Q347N-X-Y349T, Q347N-X-Y349S, Y349N-X-L351T, Y349N-X-L351S, L351N-X-P353T, L351N-X-P353S, S354N-X-D356T, S354N-X-D356S, D356N-X-L358T, D356N-X-L358S, E357N-X-T359S, K360N-X-Q362T, K360N-X-Q362S, S364N-X-T366S, L368N-X-K370T, L368N-X-K370S, K370N-X-F372T, K370N-X-F372S, K392N-X-T394S, V397N-X-D399T, V397N-X-D399S, S400N-X-G402T, S400N-X-G402S, D401N-X-S403T, F405N-X-Y407T, F405N-X-Y407S, Y407N-X-K409T, Y407N-X-K409S, K409N-X-T411S, K439N-X-L441T, K439N-X-L441S, S444N-X-G446T, and S444N-X-G446S. In other embodiments, the amino acid modifications in the CH3-CH3 dimerization interface are selected from the group consisting of S364N-X-T366S, L368N-X-K370T, L368N-X-K370S, F405N-X-Y407T, F405N-X-Y407S, Y407N-X-K409T, and Y407N-X-K409S In another aspect, the invention provides a monomeric Fc-containing polypeptide comprising an IgG CH2 and an IgG CH3 domain, wherein the CH3 domain comprises two engineered N-linked glycosylation sites in the CH3-CH3 dimerization interface, wherein the engineered N-linked glycosylation site comprises one or more amino acid modifications having a consensus sequence of Asn-X-Ser or Asn-X-Thr, and wherein X is any amino acid except Pro. In one variation, the invention provides a polypeptide comprising at least two recombinantly linked monomeric Fc-containing polypeptides as described herein, wherein each Fc-containing polypeptide has the same or different engineered N-linked glycosylation sites in the CH3-CH3 dimerization interface. In some embodiments, the amino acid modifications in the CH3-CH3 dimerization interface are selected from the group consisting of a) S364N-X-T366 and Y407N-X-K409T; b) S364N-X-T366S and Y407N-X-K409T; c) S364N-X-T366 and Y407N-X-K409S; and d) S364N-X-T366S and Y407N-X-K409S.

In another aspect, the invention provides a monomeric Fc-containing polypeptide or a polypeptide comprising at least two recombinantly linked monomeric Fc-containing polypeptides as described herein, which further comprise one or more engineered N-linked glycosylation sites in the CH2-CH2 interface. In some embodiments, the amino acid modification in the CH2 domain is selected from the group consisting of S239N-X-F241S, S239N-X-F241T, F241N-X-243T, F241N-X-243S, E258N-X-T260, E258N-X-T260S, T260N-X-V262T, T260N-X-V262S, V262N-X-V264S, V262N-X-V264T, N286-X-K288T, K288S, K288N-K290T, K288N-X-K290S, V305N-X-T307, and V305-X-T307S.

In yet another aspect, the invention provides a monomeric Fc-containing polypeptide comprising at least one engineered N-linked glycosylation site, wherein the engineered N-linked glycosylation site comprises at least one amino acid modification selected from the group consisting of E258N-X-T260S, T260N-X-V262T, T260N-X-V262S, V305N, V305N-X-T307S, Q347N-X-Y349T, Q347N-X-Y349S, S364N-X-T366S, T366N-X-L368T, T366N-X-L368S, L368N-X-K370T, L368N-X-K370S, D401N, D401N-X-S403T, F405N-X-Y407T, F405N-X-Y407S, Y407N-X-K409T, Y407N-X-K409S, and K409N-X-T411S, wherein X is any amino acid except Pro. In one variation, the invention provides a polypeptide comprising at least two recombinantly linked monomeric Fc-containing polypeptides as described herein, wherein each Fc-containing polypeptide has the same or different engineered N-linked glycosylation sites.

In some embodiments, the CH3 and/or CH2 region is an IgG1, IgG2, IgG3, or IgG4 CH2 and/or CH3 region. In some embodiments, the CH3 and/or CH2 region comprises a human IgG CH3 and/or CH2 region (e.g., human IgG1, IgG2, IgG3, or IgG4 CH3 and/or CH2 region). In some embodiments, the monomeric Fc-containing polypeptide as described herein further comprises a Fab. In some embodiments, the monomeric Fc-containing polypeptide is a Fc fusion protein.

In some embodiments, each monomeric Fc-containing polypeptide in the polypeptide comprising at least two recombinantly linked monomeric Fc-containing polypeptides as described herein is linked recombinantly via C—N terminus linkage or via a linker. In some embodiments, the linker comprises the amino acid sequence (GGGGS)n (SEQ ID NO: 89), wherein n=1-10.

In some embodiments, the monomeric Fc-containing polypeptide as described herein is stabilized by the N-linked glycosylation.

In another aspect, the invention provides an isolated polynucleotide comprising a nucleotide sequence encoding the monomeric Fc-containing polypeptide as described herein. In some embodiments, the invention provides a vector comprising the polynucleotide. In some embodiments, the invention provides a host cell comprising the monomeric Fc-containing polypeptide or the vector as described herein or a cell line expressing the monomeric Fc-containing polypeptide as described herein.

In another aspect, the invention provides a method for producing the monomeric Fc-containing polypeptide as described herein comprising the step of culturing the host cell and, optionally, recovering the polypeptide. This invention also provides pharmaceutical compositions/formulations that comprise the monomeric Fc-containing polypeptide as described herein.

In another aspect, the invention provides a method for treating a condition, disorder, or disease in a subject in need of, the method comprising administering to the subject an effective amount of a pharmaceutical composition comprising the monomeric Fc-containing polypeptide as described herein.

BRIEF DESCRIPTION OF THE DRAWINGS

FIG. 2 depicts a sequence alignment of CH3 domains of human and mouse IgG isotypes. hIgG1, hIgG2, hIgG3, hIgG4, mIgG1, mIgG2A, mIgG2B, and mIgG3 corresponding to SEQ ID NOs: 1, 2, 3, 4, 5, 6, 7, and 8, respectively. The asterisk "*" denotes the positions rationally selected for N-glycosylation according to the present invention.

FIG. 3 depicts a sequence alignment of CH2 domains of human and mouse IgG isotypes. hIgG1, hIgG2, hIgG3, hIgG4, mIgG1, mIgG2A, mIgG2B, and mIgG3 corresponding to SEQ ID NOs: 9, 10, 11, 12, 13, 14, 15, and 16, respectively. The asterisk "*" denotes the potential N-glycosylation sites according to the present invention.

FIG. 5, comprising panels A, B and C, depicts drawings illustrating various constructs of monomeric Fc-containing polypeptide variants fused to a Fab.

DETAILED DESCRIPTION

Figure 1B:
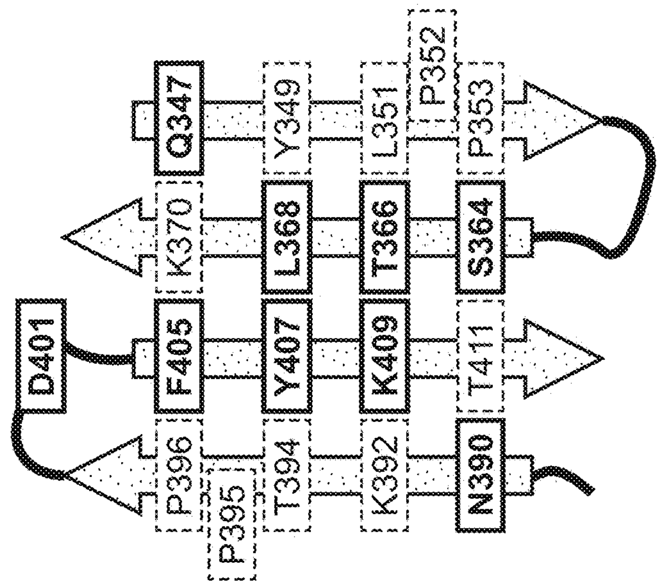
FIG. 1, comprising panels A and B, depicts schematic drawing of the amino acid residues present in the CH2-CH2 interface (FIG. 1A) and in the CH3-CH3 interface (FIG. 1B) of wild-type CH2 and CH3 domains of human IgG Fc domain.

The invention provides a monomeric Fc-containing polypeptide stabilized by one or more engineered N-linked glycosylation sites in the hydrophobic CH3-CH3 dimerization interface or in both the hydrophobic CH3-CH3 dimerization interface and the CH2-CH2 interface. The inventors have discovered that N-glycosylation incorporation at specific site(s) of the Fc-containing polypeptide can disrupt the CH3-CH3 dimerization interface, mask the exposed hydrophobic surface of the CH3 domain, monomerize a Fc dimer, provide a stable monomeric form of the Fc domain of an antibody, and/or improve physical-chemical properties of the Fc monomer (e.g., solubility and stability). In addition, the engineered glycan moieties could also sterically shield mutated amino acid residues and mask potential immune recognition or anti-drug antibody binding. The monomeric Fc-containing polypeptide maintains the binding affinity for neonatal Fc receptor (FcRn) in a pH-dependent manner. Once armed with the disclosure provided herein, the skilled artisan would appreciate that the crystal structure of the monomeric Fc-containing polypeptide provides the rationale for stabilization by carbohydrates as well as for molecular recognition for FcRn-mediated recycling. The data disclosed herein further demonstrate that the monomeric Fc-containing polypeptide also prolongs the in vivo half-life of an antibody Fab domain. The inventors have further discovered that a polypeptide comprising at least two recombinantly linked monomeric Fc-containing polypeptides each stabilized by one or more engineered N-linked glycosylation site(s) in the hydrophobic CH3-CH3 dimerization interface or in both the hydrophobic CH3-CH3 dimerization interface and the CH2-CH2 interface has higher affinity for FcRn and a longer half-life than the same polypeptide in the absence of the engineered N-linked glycosylation site(s). Without wishing to be bound by any particular theory, the increased affinity demonstrated by the polypeptide comprising at least two recombinantly linked monomeric Fc-containing polypeptide as described herein may be due to slowing of the dissociation of the polypeptide from FcRn in the endosome at acidic pH thereby preventing the polypeptide from entering a degradation pathway in the lysosome.

General Techniques and Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual,* 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, molecular biology, biochemistry, immunology, analytical chemistry, synthetic organic chemistry, and medicinal and pharmaceutical chemistry described herein are those well known and commonly used in the art. Throughout this specification and claims, the word "comprise," or variations such as "comprises" or "comprising," will be understood to imply the inclusion of a stated integer or group of integers but not the exclusion of any other integer or group of integers.

The terms "polypeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

The term "Fc-containing polypeptide" as used herein refers to a polypeptide (e.g., an antibody or an immunoadhesin) comprising the carboxyl terminal polypeptide sequences of an immunoglobulin heavy chain. The Fc-containing polypeptide may comprise native or variant Fc regions (i.e., sequences). The Fc region of an immunoglobulin generally comprises two constant domains, a CH2 domain and a CH3 domain, and optionally comprises a CH4 domain. An Fc-containing polypeptide may comprise part or all of a wild-type hinge sequence (generally at its amino terminus). An Fc-containing polypeptide may be obtained or derived from any suitable immunoglobulin, such as from at least one of the various IgG1, IgG2, IgG3, or IgG4 subtypes, or from IgA, IgE, IgD or IgM. The boundaries of the Fc region of an immunoglobulin heavy chain might vary, for example, the human IgG heavy chain Fc region is usually defined to stretch from an amino acid residue at position Glu216, or from Ala231, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991.

By "engineered N-linked glycosylation site" as used herein, is meant a glycosylation site that has been introduced into a protein sequence where there was no N-linked glycosylation site in the natural amino acid sequence. That is, an engineered N-linked glycosylation site encompasses where a canonical N-linked glycosylation sequence, i.e., N-X-S or T, wherein X is any amino acid except proline, is introduced into a protein where no such sequence was present. In one embodiment, an amino acid substitution replacing an amino acid at position one of the N-X-S or T, with N creates a glycosylation site where the second amino acid residue is not proline and further wherein the third amino acid residue is already a serine or a threonine residue. In another embodiment, the first amino acid is already an asparagine, the second amino acid is not proline, such that only the third amino acid needs to be substituted by serine or threonine. In yet another embodiment, the first amino acid residue needs to be replaced by an arginine, the second amino acid is not proline and need not, but can be, replaced by another non-proline amino acid, and the third amino acid residue is replaced by a serine or a threonine. In another embodiment, the third amino acid may be serine and is replaced by threonine, or vice versa. Any permutation of the above is encompassed by the present invention.

The term "recombinantly linked" as used herein refers to a linkage of multiple proteins or peptides (e.g., monomeric Fc-containing polypeptide) as one polypeptide chain. The linkage of multiple proteins or peptides (e.g., monomeric Fc-containing polypeptide) can be made directly via either carboxyl- or amino-terminus of the protein/peptide. The linkage of multiple proteins or peptides (e.g., monomeric Fc-containing polypeptide) can also be made indirectly through non-functional polypeptide spacer such as a stretch of glycine and serine. Multiple proteins can be recombinantly expressed from a single nucleic acid to provide fusion proteins comprising multiple polypeptides as one polypeptide chain. Alternatively, each polypeptide may be chemically linked, through carboxyl-amino (C—N) terminus chemical conjugation, to provide fusion proteins comprising multiple polypeptides. Both methods provide "recombinantly linked" proteins as used herein.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', $F(ab')_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody.

A "Fab fragment" is comprised of one light chain and the CH1 and variable regions of one heavy chain. The heavy chain of a Fab molecule cannot form a disulfide bond with another heavy chain molecule.

The residue designations in this application are based on the EU numbering scheme of Kabat (Kabat et al., 1991, *Sequences of Proteins of Immunological Interest*, National Institutes of Health, Bethesda, Md., ed. 5).

A "bivalent antibody" comprises two antigen binding sites per molecule (e.g., IgG). In some instances, the two binding sites have the same antigen specificities. However, bivalent antibodies may be bispecific.

A "monovalent antibody" or a "monomeric antibody" comprises one antigen binding site per molecule (e.g., IgG).

In some instances, a monovalent antibody or a monomeric antibody can have more than one antigen binding sites, but the binding sites are from different antigens.

A "multispecific antibody" is one that targets more than one antigen or epitope. A "bispecific," "dual-specific" or "bifunctional" antibody is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), *Clin. Exp. Immunol.* 79:315-321; and Kostelny et al. (1992), *J. Immunol.* 148:1547-1553. The two binding sites of a bispecific antibody will bind to two different epitopes, which may reside on the same or different protein targets.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Further, in contrast to polyclonal antibody preparations that typically include different antibodies directed against different determinants (epitopes), each monoclonal antibody is directed against a single determinant on the antigen.

The monoclonal antibodies herein may, in certain embodiments, specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Humanized antibodies may, moreover, comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

As used herein, the term "immunoadhesin" designates antibody-like or immunoglobulin-like molecules which combine the "binding domain" of a heterologous protein (an "adhesin", e.g. a receptor, ligand or enzyme) with the effector component of immunoglobulin constant domains. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG1, IgG2, IgG3, or IgG4 subtypes, IgA, IgE, IgD or IgM.

By "Fc fusion protein" as used herein is meant a protein wherein one or more polypeptides is operably linked to an Fc polypeptide (e.g., a monomeric Fc-containing polypeptide as described herein). An Fc fusion combines the Fc region of an immunoglobulin (e.g., a monomeric Fc-containing polypeptide as described herein) with a fusion partner, which in general may be any protein, polypeptide, or small molecule. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, for example without limitation, an extracellular receptor that is implicated in disease.

The "hinge region," "hinge sequence", and variations thereof, as used herein, includes the meaning known in the art, which is illustrated in, for example, Janeway et al., ImmunoBiology: the immune system in health and disease, (Elsevier Science Ltd., NY) (4th ed., 1999); Bloom et al., *Protein Science* (1997), 6:407-415; Humphreys et al., *J. Immunol. Methods* (1997), 209:193-202.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide" or "nucleic acid molecule," which may be used interchangeably herein, refers to a polymeric, possibly isolated, form of nucleosides or nucleotides of at least 10 bases in length. The term includes single and double stranded forms. The nucleotides can be deoxyribonucleotides, ribonucleotides, modified nucleotides or bases, and/or their analogs, or any substrate that can be incorporated into a polymer by DNA or RNA polymerase, or by a synthetic reaction.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)$NR_2$ ("amidate"), P(O)R, P(O)OR', CO or $CH_2$ ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

A reference to a nucleotide sequence as used herein encompasses its complement unless otherwise specified. Thus, a reference to a nucleic acid having a particular sequence should be understood to encompass its complementary strand, with its complementary sequence, unless otherwise defined by context.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

An "individual" or a "subject" is a mammal, more preferably, a human. Mammals also include, but are not limited to, farm animals, sport animals, pets, primates, horses, dogs, cats, mice and rats.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 21st Ed. Mack Publishing, 2005).

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, *Ann. Rev. Immunol.,* 9:457-92, 1991; Capel et al., *Immunomethods,* 4:25-34, 1994; and de Haas et al., *J. Lab. Clin. Med.,* 126:330-41, 1995. "FcR" also includes the neonatal receptor, FcRn, which is responsible for the transfer of maternal IgGs to the fetus (Guyer et al., *J. Immunol.,* 117:587, 1976; and Kim et al., *J. Immunol.,* 24:249, 1994).

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

Reference to "about" a value or parameter herein includes (and describes) embodiments that are directed to that value or parameter per se. For example, description referring to "about X" includes description of "X." Numeric ranges are inclusive of the numbers defining the range. "About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. Exemplary methods and materials are described herein, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

Monomeric Fc-Containing Polypeptides

In one aspect, this invention provides a monomeric Fc-containing polypeptide comprising an IgG CH2 and an IgG CH3 domain, wherein the CH3 domain comprises one or more engineered N-linked glycosylation site(s) in the CH3-CH3 dimerization interface, wherein the engineered N-linked glycosylation site comprises at least one amino acid modification to provide a consensus sequence of Asn-X-Ser or Asn-X-Thr, wherein X is any amino acid except Pro.

Any amino acid except Pro, as used herein, includes a naturally occurring amino acid residue such as Met, Ala, Val, Leu, Ile, Cys, Ser, Thr, Asn, Gln, Asp, Glu, Lys, Arg, Gly, Trp, Tyr, Phe, and His. In some aspects, X is any amino acid except proline or cysteine. In some aspects, X is selected from the group consisting of G, A, I, L, V, M, F, W, S, T, C, Y, N, Q, D, E, K, R, and H. In some aspects, X is selected from the group consisting of G, A, I, L, V, M, F, W, S, T, Y, N, Q, D, E, K, R, and H. In some aspects, X is G. In some aspects, X is A. In some aspects, X is I. In some aspects, X is L. In some aspects, X is V. In some aspects, X is M. In some aspects, X is F. In some aspects, X is W. In some aspects, X is S. In some aspects, X is T. In some aspects, X is C. In some aspects, X is Y. In some aspects, X is N. In some aspects, X is Q. In some aspects, X is D. In some aspects, X is E. In some aspects, X is K. In some aspects, X is R. In some aspects, X is H. The foregoing applies to all references of X in the specification, except where expressly otherwise indicated or technically prohibited.

The method used for determining where to incorporate N-linked glycosylation sites (Asn-X-Ser or Asn-X-Thr) in the hydrophobic CH3-CH3 dimerization interface (see FIG. 1) is described in Example 1 and includes the following: 1) identifying residues located on the CH3-CH3 dimerization interface based on the crystal structure (e.g., human gamma 1 Fc) and calculating the percent accessible surface (% ASA) of each residue in both Fc dimer and one chain of Fc dimer (theoretical Fc monomer since, to the best knowledge of the inventors, no crystal structure had been derived for monomeric Fc before the present invention); 2) avoiding mutagenesis of amino acid residues that play an important role in maintaining the structural framework of protein (e.g., proline, glycine, and cysteine residues); 3) incorporating the consensus sequence of Asn-X-Ser or Asn-X-Thr at the identified amino acid residues in the CH3-CH3 dimerization interface, wherein X is any amino acid except Pro; and 4) manually inspecting the amino acid residues mapped on the three-dimensional structure of one chain of Fc domain, and eliminating the positions where the engineered N-linked glycosylation site could have little impact to separate the CH3-CH3 interface (e.g., Leu256 and 276Asp).

Accordingly, in some embodiments, the amino acid modifications in the CH3-CH3 dimerization interface are selected from the group consisting of Q347N-X-Y349T, Q347N-X-Y349S, Y349N-X-L351T, Y349N-X-L351S, L351N-X-P353T, L351N-X-P353S, S354N-X-D356T, S354N-X-D356S, D356N-X-L358T, D356N-X-L358S, E357N-X-T359S, K360N-X-Q362T, K360N-X-Q362S, S364N-X-T366S, L368N-X-K370T, L368N-X-K370S, K370N-X-F372T, K370N-X-F372S, K392N-X-T394S, V397N-X-D399T, V397N-X-D399S, S400N-X-G402T, S400N-X-G402S, D401N-X-S403T, F405N-X-Y407T, F405N-X-Y407S, Y407N-X-K409T, Y407N-X-K409S, K409N-X-T411S, K439N-X-L441T, K439N-X-L441S, S444N-X-G446T, and S444N-X-G446S, wherein X is any amino acid except Pro.

In some embodiments, the amino acid modifications in the CH3-CH3 dimerization interface are selected from the group consisting of S364N-X-T366S, L368N-X-K370T, L368N-X-K370S, F405N-X-Y407T, F405N-X-Y407S, Y407N-X-K409T, and Y407N-X-K409S. In some embodiments, the amino acid modification in the CH3-CH3 dimerization interface is S364N-X-T366S, Y407N-X-K409T, or Y407N-X-K409S.

In some embodiments, the CH3 region is an IgG1, IgG2, IgG3, or IgG4 CH3 region. In some embodiments, the CH3 region comprises a human IgG CH3 region (e.g., human IgG1, IgG2, IgG3, or IgG4 CH3 and/or CH2 region). Examples of the monomeric Fc-containing polypeptide as described herein are provided in SEQ ID NOs: 17-52.

In another aspect, the invention also provides a monomeric Fc-containing polypeptide comprising an IgG CH2 and an IgG CH3 domain, wherein the CH3 domain comprises two engineered N-linked glycosylation sites in the CH3-CH3 dimerization interface, wherein the engineered N-linked glycosylation site comprises one or more amino acid modifications having a consensus sequence of Asn-X-Ser or Asn-X-Thr, and wherein X is any amino acid except Pro.

Accordingly, in some embodiments, the amino acid modifications in the CH3-CH3 dimerization interface are selected from the group consisting of a) S364N and Y407N-X-K409T; b) S364N-X-T366S and Y407N-X-K409T; c) S364N and Y407N-X-K409S; and d) S364N-X-T366S and Y407N-X-K409S. Exemplary monomeric Fc-containing polypeptides of the invention comprising two engineered N-linked glycosylation sites are provided in SEQ ID NOs: 53-58.

In another aspect, the invention further comprises one or more engineered N-linked glycosylation sites in the CH2-CH2 interface, wherein the engineered N-linked glycosylation site comprises one or more amino acid modifications having a consensus sequence of Asn-X-Ser or Asn-X-Thr, and wherein X is any amino acid except Pro. In some embodiments, the amino acid modification in the CH2 domain is selected from the group consisting of S239N-X-F241S, S239N-X-F241T, F241N-X-F243T, F241N-X-F243S, E258N, E258N-X-T260S, T260N-X-V262T, T260N-X-V262S, V262N-X-V264S, V262N-X-V264T, K288T, K288S, K288N-K290T, K288N-K290S, V305N, and V305-X-T307S. In other embodiments, the amino acid modification in the CH2 domain is selected from the group consisting of E258N, E258N-X-T260S, T260N-X-V262T, T260N-X-V262S, K288T, K288S, V305N, and V305-X-T307S. Examples of the monomeric Fc-containing polypeptide comprising engineered N-linked glycosylation sites in both the CH3-CH3 dimerization interface and the CH2-CH2 interface are provided in SEQ ID NOs: 59-66.

In another aspect, the invention provides a monomeric Fc-containing polypeptide comprising at least one engineered N-linked glycosylation site, wherein the engineered N-linked glycosylation site comprises at least one amino acid modification selected from the group consisting of E258N-X-T260S, T260N-X-V262T, T260N-X-V262S, V305N, V305N-X-T307S, Q347N-X-Y349T, Q347N-X-Y349S, S364N-X-T366S, T366N-X-L368T, T366N-X-L368S, L368N-X-K370T, L368N-X-K370S, D401N, D401N-X-S403T, F405N-X-Y407T, F405N-X-Y407S, Y407N-X-K409T, Y407N-X-K409S, and K409N-X-T411S, wherein X is any amino acid except Pro.

In another aspect, the invention provides a polypeptide comprising at least two recombinantly linked monomeric Fc-containing polypeptides as described herein, wherein each Fc-containing polypeptide has the same or different engineered N-linked glycosylation sites in the CH3-CH3 dimerization interface or both the CH3-CH3 dimerization interface and the CH2-CH2 interface.

Each of the monomeric Fc-containing polypeptide can be recombinantly linked to another monomeric Fc-containing polypeptide directly via carboxyl-amino (C—N) terminus linkage or indirectly via a linker or a spacer. In some embodiments, a linker or a spacer can be a short linking peptide. An example of a linking peptide is (GGGGS). (SEQ ID NO: 89), wherein n can be any of 1-20, 1-15, 1-10, or 1-5. For example, n can be any of 1, 2, 3, 4, 5, 6, 7, 8, 9, 10, 11, 12, 13, 14, 15, 16, 17, 18, 19, or 20. Other examples of linkers or spacers have been designed and used (Bird et al., *Science* 242:423-426 (1988)). Linkers or spacers are short, flexible polypeptides and preferably comprise of less than about 20 amino acid residues. Linkers or spacers can in turn be modified for additional functions, such as attachment of drugs or attachment to solid supports.

Accordingly, in some embodiments, the invention provides a polypeptide comprising at least two recombinantly linked monomeric Fc-containing polypeptides, wherein each Fc-containing polypeptide comprises the same engineered N-linked glycosylation sites in the CH3-CH3 dimerization interface, and wherein each Fc-containing polypeptide is linked recombinantly via a linker. In some embodiments, each Fc-containing polypeptide comprises the engineered N-linked glycosylation sites S364N and Y407N-X-K409T, wherein X is any amino acid except Pro (e.g., Leu and Ser). In other embodiments, each Fc-containing polypeptide comprises the engineered N-linked glycosylation sites S364N-X-T366S and Y407N-X-K409T. In some embodiments, the linker is GGGGS (SEQ ID NO: 89), GGGGSGGGGS (SEQ ID NO: 90), GGGGSGGGGSGGGGS (SEQ ID NO: 91), GGGGSGGGGSGGGGSGGGGS (SEQ ID NO: 92), or GGGGSGGGGSGGGGSGGGGSGGGGS (SEQ ID NO: 93). Examples of the polypeptide comprising at least two identical recombinantly linked monomeric Fc-containing polypeptides as described herein are provided in SEQ ID NOs: 79-88.

In other embodiments, the invention provides a polypeptide comprising at least two recombinantly linked monomeric Fc-containing polypeptides, wherein each Fc-containing polypeptide comprises different engineered N-linked glycosylation sites in the CH3-CH3 dimerization interface, and wherein each Fc-containing polypeptide is linked recombinantly via a linker. In some embodiments, the first Fc-containing polypeptide comprises the engineered N-linked glycosylation sites S364N and Y407N-X-K409T, and the second Fc-containing polypeptide comprises the engineered N-linked glycosylation sites S364N-X-T366S and Y407N-X-K409T wherein X is any amino acid except Pro (e.g., Leu and Ser). In some embodiments, the linker is GGGGS (SEQ ID NO: 89), GGGGSGGGGS (SEQ ID NO: 90), GGGGSGGGGSGGGGS (SEQ ID NO: 91), GGGGSGGGGSGGGGSGGGGS (SEQ ID NO: 92), or GGGGSGGGGSGGGGSGGGGSGGGGS (SEQ ID NO: 93).

In another embodiment, the invention provides a polypeptide comprising at least two recombinantly linked monomeric Fc-containing polypeptides, wherein each Fc-containing polypeptide comprises the same or different engineered N-linked glycosylation sites in the CH3-CH3 dimerization interface, and wherein each Fc-containing polypeptide is linked recombinantly directly via the C—N terminus. Accordingly, in some embodiments, each Fc-containing polypeptide comprises the engineered N-linked glycosylation sites S364N and Y407N-X-K409T (see, e.g., SEQ ID NOs: 77-78) or S364N-X-T366S and Y407N-X-K409T. In some embodiments, the first Fc-containing polypeptide comprises the engineered N-linked glycosylation sites S364N and Y407N-X-K409T, and the second Fc-containing polypeptide comprises the engineered N-linked glycosylation sites S364N-X-T366S and Y407N-X-K409T.

The polypeptide comprising two recombinantly linked monomeric Fc-containing polypeptides as described herein binds to FcRn with high affinity similar to that of wild type IgG that does not comprise an engineered N-linked glycosylation site. See Example 5. Such polypeptide as described herein also binds tightly to FcRn at acidic pH, dissociates from FcRn efficiently at neutral pH, and shows at least 2-fold longer serum half-life than the polypeptide comprising one monomeric Fc engineered. See, e.g., Examples 5-6. Accordingly, in some embodiments, the polypeptide comprising at least two recombinantly linked monomeric Fc-containing polypeptides as described herein has serum half-life at least about any of 2-fold, 3-fold, 4-fold, 5-fold, 6-fold, 7-fold, 8-fold, and 9-fold longer than the serum half-life exhibited by the polypeptide comprising one monomeric Fc-containing polypeptide comprising two engineered N-linked glycosylation site.

Any molecule comprising an Fc domain may comprise a monomeric Fc-containing polypeptide of the invention. For example, the monomeric Fc-containing polypeptide may be linked, conjugated, or fused to, for example, a Fab or a heterologous polypeptide sequence (e.g., Fc-fusion protein). Accordingly, in some embodiments, a Fab is fused to the monomeric Fc-containing polypeptide comprising one or more engineered N-linked glycosylation sites in the CH3-CH3 dimerization interface or in both the CH2-CH2 interface and the CH3-CH3 dimerization interface. See, e.g., Examples 5 and 6. In other embodiments, a Fab is fused the polypeptide comprising at least two recombinantly linked monomeric Fc-containing polypeptide as described herein. See, e.g., Examples 5 and 6.

In other embodiments, the monomeric Fc-containing polypeptide may be modified or derivatized, such as by making a fusion antibody or immunoadhesin that comprises all or a portion of the monomeric Fc-containing polypeptide linked to another polypeptide or molecular agent. Monomeric Fc-containing polypeptides as described herein may be modified or derivatized, for example, to extend in vivo half-lives further, by producing more stable fusion molecules and/or by treatment with biocompatible polymers such as polyethylene glycol (PEG), commonly referred to as "pegylation," or by any of a number of other engineering methods well known in the art.

The monomeric Fc-containing fusion protein may be derivatized with a chemical group, including but not limited to polyethylene glycol (PEG), a methyl or ethyl group, an ester, a carbohydrate group and the like, using well known techniques. These chemical groups (and others like them which have been used to stability therapeutic compounds in vivo) are useful to improve the biological characteristics of the monomeric Fc-containing polypeptide, e.g., to increase serum half-life and bioactivity.

The monomeric Fc-containing fusion protein may also be labeled using any of a multitude of methods known in the art. As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In another aspect of the invention, the monomeric Fc-containing polypeptides as described herein may be deimmunized to reduce immunogenicity upon administration to a subject using known techniques such as those described, e.g., in PCT Publication WO98/52976 and WO00/34317.

In another aspect of the invention, the monomeric Fc-containing polypeptide may comprise additional mutations and/or modifications to alter the characteristics (e.g., PK, immunogenicity, aggregation, or serum half-life) of the polypeptide. For example, the monomeric Fc-containing polypeptide as described herein may additionally comprise a leucine at position 428 and a serine at position 434. See, e.g., U.S. Pat. No. 8,088,376.

Nucleic Acids, Vectors and Cells

The present invention also encompasses nucleic acid molecules and sequences encoding the monomeric Fc-containing polypeptides as described herein. In some embodiments, different nucleic acid molecules encode one or more of or portions of the monomeric Fc-containing polypeptides as described herein. In other embodiments, the same nucleic acid molecule encodes the monomeric Fc-containing polypeptides as described herein.

Nucleic acid molecules of the invention include nucleic acids that hybridize under highly stringent conditions, such as those at least about 70%, 75%, 80%, 85%, 90%, 95%, 97%, 98% or 99% or more identical to a nucleic acid sequence of the invention.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In a further aspect, the present invention provides a vector comprising a nucleic acid sequence encoding one or more of or portions of the monomeric Fc-containing polypeptides as described herein.

In a further aspect, the present invention provides a vector suitable for expressing one or more of or portions of the monomeric Fc-containing polypeptide as described herein.

In another embodiment, a nucleic acid molecule of the invention is used as a probe or PCR primer for a specific amino acid sequence, e.g., a specific antibody sequence such as in CH2 and/or CH3 domain regions. For instance, the nucleic acid can be used as a probe in diagnostic methods or as a PCR primer to amplify regions of DNA that could be used, inter alia, to isolate additional nucleic acid molecules encoding useful sequences. In some embodiments, the nucleic acid molecules are oligonucleotides. In some embodiments, the oligonucleotides are from CH2 and/or CH3 domain regions of the heavy chain of an antibody of interest. In some embodiments, the oligonucleotides encode all or a part of one or more of the modified CH3 region of the monomeric Fc-containing polypeptide.

Recombinant expression vectors of the invention may, in some embodiments, carry regulatory sequences that control the expression of antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants is known in the art. See, e.g. U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr$^-$ host cells with methotrexate selection/amplification), the neo gene (for G418 selection), and the glutamate synthetase gene.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Methods of Producing Monomeric Fc-Containing Polypeptides

In one aspect, this invention provides methods of producing a monomeric Fc-containing polypeptide or a polypeptide comprising at least two recombinantly linked monomeric Fc-containing polypeptides as described herein.

In some embodiments, provided is a method of producing a monomeric Fc-containing polypeptide comprising the steps of: a) culturing a host cell comprising a nucleic acid molecule encoding a monomeric Fc-containing polypeptide comprising an IgG CH2 and an IgG CH3 domain, wherein the CH3 domain comprises one or more engineered N-linked glycosylation sites in the CH3-CH3 dimerization interface or both the CH3-CH3 dimerization interface and the CH2-CH2 interface, and wherein the cultured host cell expresses the monomeric Fc-containing polypeptide; and, optionally, b) recovering the monomeric Fc-containing polypeptide from the host cell culture. In some embodiments, the engineered N-linked glycosylation site comprises one or more (e.g., two) amino acid modifications having a consensus sequence of Asn-X-Ser or Asn-X-Thr, and wherein X is any amino acid except Pro.

In some embodiments, provided is a method of producing a polypeptide comprising at least two recombinantly linked monomeric Fc-containing polypeptides comprising the steps of: a) culturing a host cell comprising a nucleic acid molecule encoding a first monomeric Fc-containing polypeptide comprising an IgG CH2 and an IgG CH3 domain, wherein the CH3 domain comprises one or more engineered N-linked glycosylation sites in the CH3-CH3 dimerization interface or both the CH3-CH3 dimerization interface and the CH2-CH2 interface, and the same or a different nucleic acid molecule encoding a second monomeric Fc-containing polypeptide having the same or different engineered N-linked glycosylation site(s) as the first monomeric Fc-containing polypeptide, wherein the cultured host cell expresses the first and the second monomeric Fc-containing polypeptide; and b) recovering the polypeptide. In some embodiments, the engineered N-linked glycosylation site comprises one or more (e.g., two) amino acid modifications having a consensus sequence of Asn-X-Ser or Asn-X-Thr, and wherein X is any amino acid except Pro. In some embodiments, the first and the second monomeric Fc-containing polypeptide is linked recombinantly via C—N terminus linkage or via a linker using the linkers as disclosed herein.

In some embodiments, provided is a method of producing a polypeptide comprising at least two recombinantly linked monomeric Fc-containing polypeptides comprising the steps of: a) expressing a first monomeric Fc-containing polypeptide comprising an IgG CH2 and an IgG CH3 domain, wherein the CH3 domain comprises one or more engineered N-linked glycosylation sites in the CH3-CH3 dimerization interface or both the CH3-CH3 dimerization interface and the CH2-CH2 interface in a first host cell; b) expressing a second monomeric Fc-containing polypeptide having the same or different engineered N-linked glycosylation site(s)

as the first monomeric Fc-containing polypeptide in a second host cell; c) isolating the first monomeric Fc-containing polypeptide of step a) and the second monomeric Fc-containing polypeptide of step b); and d) incubating the two monomeric Fc-containing polypeptides of step c) under a condition suitable for the polypeptide formation (e.g., polypeptide comprising at least two recombinantly linked monomeric Fc-containing polypeptides). In some embodiments, the engineered N-linked glycosylation site comprises one or more (e.g., two) amino acid modifications having a consensus sequence of Asn-X-Ser or Asn-X-Thr, and wherein X is any amino acid except Pro. In some embodiments, the two monomeric Fc-containing polypeptides of step c) are incubated in the presence of linkers (e.g., (GGGGS)n (SEQ ID NO: 89), wherein n is 1-10) as disclosed herein In some embodiments, provided is a method of producing a polypeptide comprising at least two recombinantly linked monomeric Fc-containing polypeptides comprising the steps of: a) providing a first monomeric Fc-containing polypeptide comprising an IgG CH2 and an IgG CH3 domain, wherein the CH3 domain comprises one or more engineered N-linked glycosylation sites in the CH3-CH3 dimerization interface or both the CH3-CH3 dimerization interface and the CH2-CH2 interface; b) providing a second monomeric Fc-containing polypeptide comprising an IgG CH2 and an IgG CH3 domain, wherein the CH3 domain comprises one or more engineered N-linked glycosylation sites in the CH3-CH3 dimerization interface or both the CH3-CH3 dimerization interface and the CH2-CH2 interface; c) allowing the first monomeric Fc-containing polypeptide to link recombinantly with the second monomeric Fc-containing polypeptide. In some embodiments, the first monomeric Fc-containing polypeptide is the same as or different from the second monomeric Fc-containing polypeptide. In some embodiments, the engineered N-linked glycosylation site comprises one or more (e.g., two) amino acid modifications having a consensus sequence of Asn-X-Ser or Asn-X-Thr, and wherein X is any amino acid except Pro. In some embodiments, the first and the second monomeric Fc-containing polypeptide is linked recombinantly via C—N terminus linkage or via a linker using the linkers as disclosed herein.

In some embodiments, the methods described herein further comprise a purification step by chromatography.

Chromatography includes, but is not limited to, affinity chromatography, ion exchange chromatography, hydrophobic interaction chromatography, hydroxyapatite chromatography, gel filtration chromatography, reverse-phase chromatography, adsorption chromatography, liquid phase chromatography (e.g., HPLC (High-Performance (or Pressure) Liquid Chromatography) and FPLC (Fast Protein Liquid Chromatography)), size exclusion chromatography, and weak partitioning chromatography. Examples of columns for affinity chromatography include protein A (synthetic, recombinant, or native) columns and protein G (synthetic, recombinant, or native) columns.

The skilled artisan can readily determine, using well-known techniques, the relative amounts of molecules or antibodies to use according to the methods disclosed herein.

In the methods disclosed herein, incubations may be performed across a range of temperatures. Such temperatures will be recognized by those skilled in the art and will include, for example, incubation temperatures at which deleterious physical changes such as denaturation or decomposition do not occur in the mixed molecules or antibodies. In certain embodiments, the incubations are performed at 37° C.

Any of a number of host cells may be used in methods of the invention. Such cells are known in the art (some of which are described herein) or can be determined empirically with respect to suitability for use in methods of the invention using routine techniques known in the art. In certain embodiments, the host cell is prokaryotic. In some embodiments, a host cell is a gram-negative bacteria cell. In other embodiments, a host cell is *E. coli*. In some embodiments, the *E. coli* is of a strain deficient in endogenous protease activities. In some embodiments, the genotype of an *E. coli* host cell lacks degP and prc genes and harbors a mutant spr gene.

In some embodiments, methods of the invention further comprise expressing in a host cell a polynucleotide or recombinant vector encoding a molecule the expression of which in the host cell enhances yield of a monomeric Fc-containing polypeptide as described herein. For example, such molecule can be a chaperone protein. In one embodiment, said molecule is a prokaryotic polypeptide selected from the group consisting of DsbA, DsbC, DsbG and FkpA. In some embodiments of these methods, the polynucleotide encodes both DsbA and DsbC.

Non-Hybridoma Host Cells and Methods of Recombinantly Producing Protein

In one aspect, the present invention provides recombinant host cells allowing the recombinant expression of the monomeric Fc-containing polypeptide as described herein. Antibody fragments produced by such recombinant expression in such recombinant host cells are referred to herein as "recombinant antibody fragments". The present invention also provides progeny cells of such host cells, and antibodies produced by same. The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein. Such cell may comprise a vector according to the invention as described above.

In another aspect, the present invention provides a method for making the monomeric Fc-containing polypeptide as described above. According to one embodiment, said method comprises culturing a cell transfected or transformed with a vector as described above, and retrieving said monomeric Fc-containing polypeptide thereof. Nucleic acid molecules encoding the monomeric Fc-containing polypeptide and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455. Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies (e.g., monomeric antibody fragments) can be recovered from the culture medium using standard protein purification methods. Suitable plant host cells may include, e.g., *Nicotiana, Arabidopsis*, duckweed, corn, wheat, potato, etc. Suitable bacterial host cells may include, e.g., *E. coli* and *Streptomyces* species. Suitable yeast host cells may include, e.g., *Schizosaccharomyces pombe, Saccharomyces cerevisiae* and *Pichia pastoris.*

Expression of polypeptides of the invention or portions thereof from production cell lines can be enhanced using a number of known techniques. For example, the glutamine synthetase gene expression system (the GS system) is a common approach for enhancing expression under certain conditions. The GS system is discussed in whole or part in connection with EP patents 0 216 846, 0 256 055, 0 323 997 and 0 338 841.

Methods of Using Monomeric Fc-Containing Polypeptides

The present invention also provides various therapeutic applications for the monomeric Fc-containing polypeptides and the polypeptides comprising at least two recombinantly linked monomeric Fc-containing polypeptides as described herein. In one aspect, the monomeric Fc-containing polypeptides or the polypeptide comprising such Fc-containing polypeptides can be used for providing better penetration and access into solid tumors or other occluded antigens in comparison to full-size antibodies or for reducing aggregation and instability in comparison to full-size antibodies or monomeric Fc-containing polypeptides without the specific engineered N-linked glycosylation sites as described herein.

Pharmaceutical Compositions

In one aspect, the present invention provides a pharmaceutical composition comprising the monomeric Fc-containing polypeptide or a polypeptide comprising at least two recombinantly linked monomeric Fc-containing polypeptides in a pharmaceutically acceptable carrier. In certain embodiments, the polypeptides of the invention may be present in a neutral form (including zwitter ionic forms) or as a positively or negatively-charged species. In some embodiments, the polypeptides as described herein may be complexed with a counterion to form a "pharmaceutically acceptable salt," which refers to a complex comprising one or more polypeptides and one or more counterions, where the counterions are derived from pharmaceutically acceptable inorganic and organic acids and bases.

The monomeric Fc-containing polypeptide or the polypeptide comprising at least two recombinantly linked monomeric Fc-containing polypeptides as described herein may be administered alone or in combination with one or more other polypeptides of the invention or in combination with one or more other drugs (or as any combination thereof). The pharmaceutical compositions, methods and uses of the invention thus also encompass embodiments of combinations (co-administration) with other active agents, as detailed below.

As used herein, the terms "co-administration," "co-administered" and "in combination with," referring to the monomeric antibody fragments of the invention and one or more other therapeutic agents, is intended to mean, and does refer to and include the following: (i) simultaneous administration of such combination of a monomeric Fc-containing polypeptide or a polypeptide comprising at least two recombinantly linked monomeric Fc-containing polypeptides as described herein and therapeutic agent(s) to a patient in need of treatment, when such components are formulated together into a single dosage form which releases said components at substantially the same time to said patient; (ii) substantially simultaneous administration of such combination of a monomeric Fc-containing polypeptide or a polypeptide comprising at least two recombinantly linked monomeric Fc-containing polypeptides as described herein and therapeutic agent(s) to a patient in need of treatment, when such components are formulated apart from each other into separate dosage forms which are taken at substantially the same time by said patient, whereupon said components are released at substantially the same time to said patient; (iii) sequential administration of such combination of a monomeric Fc-containing polypeptide or a polypeptide comprising at least two recombinantly linked monomeric Fc-containing polypeptides as described herein and therapeutic agent(s) to a patient in need of treatment, when such components are formulated apart from each other into separate dosage forms which are taken at consecutive times by said patient with a significant time interval between each administration, whereupon said components are released at substantially different times to said patient; and (iv) sequential administration of such combination of a monomeric Fc-containing polypeptide or a polypeptide comprising at least two recombinantly linked monomeric Fc-containing polypeptides as described herein and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

Generally, the monomeric Fc-containing polypeptide or the polypeptide comprising at least two recombinantly linked monomeric Fc-containing polypeptides as described herein are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in Remington's Pharmaceutical Sciences, 21st Edition (Mack Publishing Company, 2005). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the monomeric Fc-containing polypeptides described herein.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include controlled, delayed, sustained, pulsed, targeted and programmed release formulations. For example, in one aspect, sterile injectable solutions can be prepared by incorporating the monomeric Fc-containing polypeptides, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition of the invention is a formulation as a sterile aqueous solution having a pH that ranges from about 5.0 to about 6.5 and comprising from about 1 mg/mL to about 200 mg/mL of a monomeric Fc-containing polypeptide described herein, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

Dosage regimens may be adjusted to provide the optimum desired response. For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of a monomeric Fc-containing polypeptide or a polypeptide comprising at least two recombinantly linked monomeric Fc-containing polypeptide as described herein is typically in the range of about 0.5 to about 1500 mg per patient, depending, of course, on the mode of administration. For example, an intravenous monthly dose may require about 1 to about 1000 mg/patient. The total monthly dose may be administered in single or divided doses and may, at the physician's discretion, fall outside of the typical range given herein.

An exemplary, non-limiting range for a therapeutically or prophylactically effective amount of a monomeric Fc-containing polypeptide or a polypeptide comprising at least two recombinantly linked monomeric Fc-containing polypeptide as described herein is about 1 to about 1000 mg/patient/month. In certain embodiments, the monomeric Fc-containing polypeptide or a polypeptide comprising thereof may be administered at about 1 to about 200 or about 1 to about 150 mg/patient/month.

EXAMPLES

The following examples describe generation and characterization of monomeric Fc-containing polypeptides comprising one or more engineered N-linked glycosylation sites in the CH3-CH3 dimerization interface or both the CH3-CH3 dimerization interface and the CH2-CH2 interface. Generation and characterization of polypeptides comprising at least two recombinantly linked monomeric Fc-containing polypeptides is also provided. The examples provided below are meant to illustrate the methods and materials of the present invention. Suitable modifications and adaptations of the described conditions and parameters normally encountered in the art that are obvious to those skilled in the art are within the spirit and scope of the present invention.

Figure 1A:
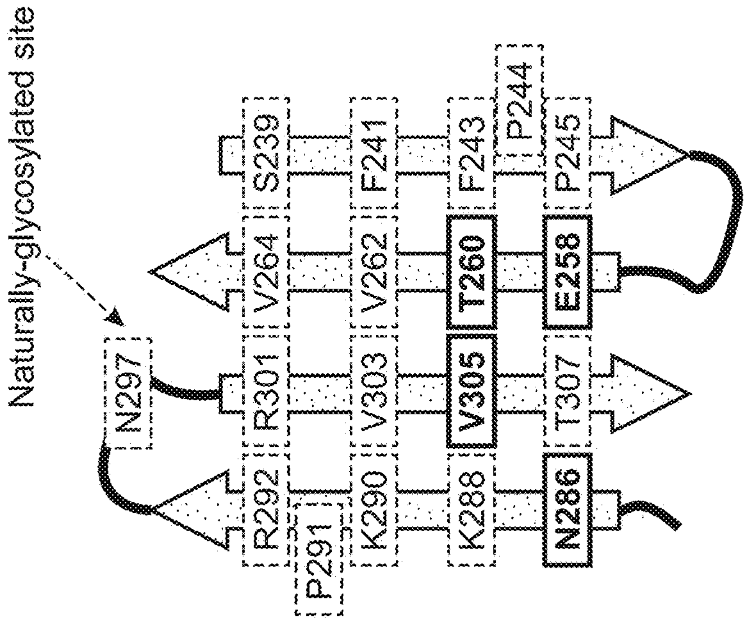

Example 1: Monomerizing an Otherwise Dimeric Fc by Incorporating N-Glycosylation Sites in the CH3-CH3 Interface A glycoengineering strategy was used to engineer a stable monomeric form of an Fc domain of an antibody. More specifically, bulky and hydrophilic carbohydrate moieties were introduced in the CH3-CH3 interface, which separated the dimer form of Fc into a monomeric form. Surprisingly, this glycoengineering also stabilized the exposed interface of CH3 domain. Four criteria were employed to determine where to incorporate N-glycosylation mutational sites (to provide the canonical N-linked glycosylation signal sequence of Asn-X-Ser/Thr). First, residues located on the interface of CH3-CH3 were identified, so as to avoid selecting the residues buried in the Ig domain core or the residues exposed to the solvent (FIG. 1). The crystal structure of human gamma1 Fc (PDB ID: 1HZH) was used to calculate the percent accessible surface (% ASA) of each residue in both Fc dimer (native form) and in one chain of an Fc dimer (i.e., a hypothetical Fc monomer) with the program MOE (Chemical Computing Group). The residues with a higher % ASA (dimer) should be the residues that are exposed to solvent. It was hypothesized that the residues with the higher % ASA (monomer) value are more likely to be either exposed to solvent or buried in the $C_H3$-$C_H3$ interface. Therefore, the degree of interface involvement was determined by subtracting the % ASA of monomer from that of Fc dimer as ΔASA=% ASA (monomer)−% ASA (dimer) and 22 interface residues were selected whose ΔASA were above a threshold value of 10%. See Table 1. Second, the mutagenesis of proline, glycine and cysteine residues was avoided because these residues generally play an important role in maintaining the structural framework of a protein. Third, the probability of glycosylation occupancy was considered. The residues Asn-X-Ser/Thr-Y were incorporated in the region where neither X (the amino acid positioned between Asn and Ser/Thr) nor Y (the amino acid positioned next to Ser/Thr) is a proline residue as proline at these positions strongly inhibits glycosylation efficiency. When residues at the third position (i.e., Ser/Thr) of the canonical N-linked glycosylation signal sequence of Asn-X-Ser/Thr must be mutated, threonine was chosen over serine because it has been shown that threonine at the third position provides higher glycan occupancy at the asparagine residue than serine at the third position. Finally, the residues were mapped on the three-dimensional structure of one chain of an Fc domain and were manually inspected, and the positions where the engineered carbohydrate could have little impact to separate the CH3-CH3 interface ($Leu^{256}$ and $Asp^{276}$) were eliminated. Thus, a total of nine positions were rationally selected for N-glycosylation. These selected residues are well conserved among all isotypes of human IgG (1, 2, 3 and 4) as well as mouse IgG (2, 2a, 2b and 3) isotypes (FIG. 2). Individual N-glycosylation mutants were constructed by using the Fc domain of human IgG1 and IgG4 without a hinge region ($Gly^{226}$ to $Lys^{497}$) as a template. The nucleic acids encoding these peptides were transiently expressed in HEK293 cells. To assess expression and efficiency of N-glycosylation, the medium supernatant was subjected to SDS-PAGE under reducing conditions as well as Western-blot analysis. Expression levels of all the mutants were similar to wild type Fc domain except that the mutant of position 366 was expressed poorly. It appeared that the N-glycosylated variants migrated with mobility corresponding to a molecular weight of approximately 25 kDa, whereas the non-glycosylated variants migrated at approximately 22 kDa. Five sites (364, 366, 368, 405 and 407) showed efficient N-glycosylation, while four sites (347, 390, 401, 409) showed approximately 50% or less incorporation of N-glycans. Since the expression and glycosylation profiles of IgG1 and IgG4 mutants were similar, IgG1 mutants were used for further studies.

TABLE 1

| % ASA | | | |
|---|---|---|---|
| Interface residues | % ASA (dimer) | % ASA (monomer) | #ΔASA |
| *Gln347 | 26.5 | 41.8 | 15.4 |
| Tyr349 | 5.1 | 41.4 | 36.3 |
| Leu351 | 3.8 | 41.9 | 38.0 |
| Ser354 | 13.6 | 60.2 | 46.6 |
| Asp356 | 47.9 | 74.4 | 26.5 |
| Glu357 | 2.8 | 26.9 | 24.1 |
| Lys360 | 42.7 | 62.9 | 20.2 |
| *Ser364 | 3.8 | 18.5 | 14.8 |
| *Thr366 | 0.7 | 21.2 | 20.5 |
| *Leu368 | 1.4 | 15.2 | 13.8 |
| Lys370 | 17.1 | 37.3 | 20.0 |
| *Asn390 | 39.9 | 55.6 | 15.7 |
| Lys392 | 42.8 | 77.6 | 34.9 |
| Thr394 | 2.5 | 42.7 | 40.2 |
| Val397 | 13.6 | 42.3 | 28.7 |
| *Asp401 | 14.0 | 32.4 | 18.5 |
| Ser400 | 56.7 | 89.2 | 32.5 |
| *Phe405 | 0 | 24.2 | 24.2 |
| *Tyr407 | 0 | 37.3 | 37.3 |
| *Lys409 | 1.5 | 50.5 | 48.9 |
| Lys439 | 27.9 | 41.3 | 13.4 |
| Ser434 | 56.8 | 68.8 | 12.0 |

*The positions selected for N-glycosylation engineering.

Example 2: Characterization of N-Glycosylation Variants

Four mutants (positions 364, 368, 405 and 407) with complete N-glycosylation were selected for further purification and characterization. These N-glycosylation mutants, denoted as CH23-N364 (Fc-S364N), CH23-N368 (Fc-L368N/K370T), CH23-N405 (Fc-F405N/Y407T) and CH23-N407 (Fc-Y407N/K409T), were purified as described elsewhere herein, resulting in >95% purity as judged by SDS-PAGE. The yields of purified protein were in the range of 20-30 mg per liter of media. In order to assess relative yields of glycosylated and non-glycosylated variants at each position, capillary gel electrophoresis (CGE) assay of purified protein without and with treatment of PNGase F was carried out. The data disclosed herein suggest that these four mutants contain up to 10% non-glycosylated variants, which is similar to wild type Fc (Table 2). Analytical size exclusion column (SEC) was used to estimate the apparent molecular weights of N-glycosylation variants. All of the four mutants showed lower apparent molecular weight (25~30 kDa) than wild type Fc (~48 kDa), suggesting that incorporated N-glycosylation successfully disrupted the CH3-CH3 interface of the Fc dimer. SEC-MALS (Size Exclusion Chromatography-Multi-Angle Light Scattering) was used to perform a more rigorous analysis of distribution of oligomeric species of the N-glycosylated mutants although these mutants appeared to be monomeric by SEC. The molecular mass determined by light scattering over the signal of the refractive index showed that CH23-N405 was completely monomeric, however CH23-N364, CH23-N405 and CH23-N407 were found to be mixtures of monomeric and dimeric forms. The thermal stability of these four N-glycosylated mutants was further characterized by Differential Scanning calorimetry (DSC). The thermograms for wild type Fc yielded two transitions with the melting temperatures of 72 and 83° C. These values were comparable with the value of 70.8° C. and 83.3° C. which have been assigned to the melting of the CH2 and CH3 domains. In contrast, the individual N-glycosylated mutants showed a single transition with lowered melting temperature (Table 2).

TABLE 2

| Summary of biophysical characterization | | | | |
|---|---|---|---|---|
| N-glycosylation mutants | % unglyco (%) | SEC-MALS | Tm (° C.) | Kd, FcRn (nM) |
| wild type Fc (w/o hinge) | 12 | dimer | 72/83 | 280 |
| CH23-N364 | 6 | monomer/dimer | 64 | 340 |
| CH23-N368 | 9 | monomer/dimer | 58 | 460 |
| CH23-N405 | 7 | monomer | 62 | 290 |
| CH23-N407 | 5 | monomer/dimer | 63 | 450 |
| CH23-N364/N368 | <0.5 | aggregation | 53/62 | 580 |
| CH23-N364/N407 | <0.5 | monomer | 64 | 220 |
| CH23-N258/N364/N407 | <0.5 | monomer | 62 | 230 |
| CH23-N260/N364/N407 | 8 | monomer | 55 | 260 |
| CH23-N286/N364/N407 | <0.5 | monomer | 64 | 520 |
| CH23-N305/N364/N407 | 10 | monomer | 57 | 320 |

Example 3: Combination of Multiple N-Glycosylation Sites

To further minimize the non-glycosylated portion for each variant, two N-glycosylation sites in CH3 domain were introduced through individual mutations at positions of 364, 368, 405 and 407, which resulted in 90% to 95% occupancy of glycosylation. FIG. 3 highlights the special alignment of $Ser^{364}$, $Leu^{368}$, $Phe^{405}$ and $Tyr^{407}$ in the interface of CH3 domain. Based on these observations, it was hypothesized that two carbohydrate moieties at two sites among 368, 405 and 407 would further destabilize the structure because these three residues are located in close proximity to each other. Therefore, three combinations of these N-linked sites, i.e., N364 and N368, N364 and N405 and N364 and N407, were selected for the incorporation of two N-glycosylation sites. These three double N-glycosylation mutants, namely CH23-N364/N368, CH23-N364/N405 and CH23-N364/N407, were expressed in HEK293 cells and were examined for expression and glycosylation by western-blot. Increases in size compared to the single N-glycosylation mutants were observed for CH23-N364/N368 and CH23-N364/N407, whereas CH23-N364/N405 was not secreted at a detectable level. Since CH23-N364/N405 was found to be expressed but not excreted by the cell, it is hypothesized that this double mutation might disable secretion of the protein or cause instability of the protein structure. Because treatment of PNGase F resulted in the molecular size that corresponds to the reduced form of the Fc domain, the increase in size of CH23-N364/N368 and CH23-N364/N407 was attributed to the presence of multiple N-linked glycans on each molecule. CH23-N364/N368 and CH23-N364/N407 proteins were purified and the oligomeric status, yield of nonglycosylated molecules, and thermal stability were investigated as described elsewhere herein. Non-glycosylated molecules of both CH23-N364/N368 and CH23-N364/N407 were decreased to an undetectable level (Table 2). CH23-N364/N407 produced was completely monomeric even though individual mutants of CH23-N364 and CH23-N407 formed detectable amounts of dimers. Of note, CH23-N364/N368 showed an aggregative tendency and a decrease in thermal stability based on SEC-MALS and DSC analyses. Nevertheless, the double mutation at positions 364 and 407 improved properties of monomeric Fc in terms of stability, glycosylation efficiency and monomeric tendency (Table 2). Glycosylation was also confirmed by analytical SEC-MALS with a UV detector at 280 nM (sensitive only to the protein component) and a RI detector (sensitive to both protein and carbohydrate components).

The CH2 domain naturally contains N-glycosylation at $Asn^{297}$ (FIG. 1). Since two engineered glycans in the CH3 domain were shown to be stabilized in the monomeric form, a glycosylation site in CH2 domain in addition to natural N-glycosylation at $Asn^{297}$ was further investigated. First, a potential engineered glycosylation site in the CH2 at positions 258, 260, 286 and 305 was identified (FIG. 1). These four residues are all conserved among all isotypes of human IgG (1, 2, 3 and 4) and mostly conserved among mouse IgG (2, 2a, 2b and 3) isotypes (FIG. 3). An individual engineered N-glycosylation site was introduced into CH23-N364/N407 and the triple N-glycosylation mutants were expressed in HEK293 cells. Thus, these mutants comprise a natural glycosylation site at N297 and three engineered glycosylation sites: one in the CH2 and two in the CH3 domain. All of the mutants were purified and examined for non-glycosylation yield, monomeric status and thermal stability as described previously and the results are shown in Table 1. CH23-N258/N364/N407 and CH23-N286/N364/N407 were found to be monomeric and completely glycosylated while CH23-N260/N364/N407 and CH23-N305/N364/N407 were monomeric but yielded approximately 5~10% non-glycosylated molecules.

Example 4: Crystal Structure of CH23-N364/N407

Figure 4:
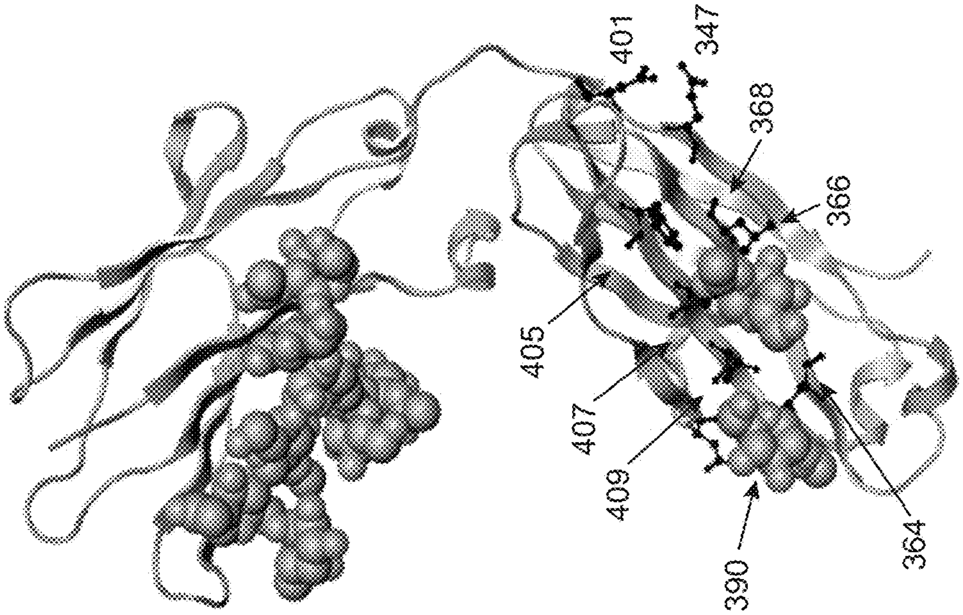
FIG. 4 depicts a graphical representation of the crystal structure obtained of an engineered monomeric Fc-containing polypeptide ("CH23-N364/407" having amino modifications in the CH3-CH3 dimerization interface at S364N (S364N-L365-T366) and Y407N-X-K409T (Y407N-S408-K409T).

Crystals of CH23-N364/N407 were grown that diffracted to 1.9 Å. The structure was solved by molecular replacement using the coordinate of one polypeptide chain of an Fc dimer (3DTS) as a search model. Data collection and refinement statistics for the data set and model are shown in Table 3. The experimental map of CH23-N364/N407 resulted in clear density for the entire backbone from Gly224 to Ser447, and >95% of the side chains were fitted to the electron density. The substitutions of S364N, Y407N, and K409T were clearly visible on the CH3 domain. The topology of carbohydrate chain connected to $Asn^{297}$ was determined from its electron density. Eight sugar residues (GlcNAc1-GlcNAc5, Man7, GlcNAc8 and Fuc) were identified. In contrast, only each sugar residue was identified onto the engineered $Asn^{364}$ and $Asn^{407}$ residues. The GlcNAc1 attached to $Asn^{364}$ side chain in accordance with its electron density was located. However, the GlcNAc1 attached to $Asn^{407}$ could not be placed due to poor electron density although the density map suggested that there are heavy atoms bigger than water molecules in close proximity of the $Asn^{407}$ side chain. Nonetheless, the asymmetric unit contents of the CH23-N364/N407 crystal showed only one monomer unit of regular Fc domain that exists as dimer of two identical glycosylated polypeptide chains (FIG. 4). These crystallographic data demonstrate that engineered glycosylation on the CH3-CH3 interface can stabilize the monomeric form of the Fc domain.

TABLE 3

| X-ray data collection and model refinement statistics | |
|---|---|
| Data collection | |
| Space group | $P3_12$ |
| Cell dimensions | |
| a, b, c (Å) | 64.22, 64.22, 146.94 |
| α, β, γ (°) | 90.0, 90.0, 120.0 |
| Resolution (Å) | 50.-1.9 (1.93-1.90) |
| No. reflections (total/unique) | 544.128/26,945 |
| Completeness (%) | 96.8 (67.3) |
| Redundancy | 4.7 (2.2) |
| Refinement | |
| Resolution (Å) | 1.9 |
| $R_{work}/R_{free}$ (%) | 25.0/25.9 |
| No. atoms | |
| Protein | 1852 |
| No. Of Carbohydrate atoms | 187 |
| Water | 74 |
| Average B-factors | |
| Protein | 48.55 |
| R.m.s. deviations | |
| Bond lengths (Å) | 0.007 |
| Bond angles (°) | 1.09 |

Example 5: Production and In Vitro Characterization of Fab-CH23 Variants

Figure 5A:
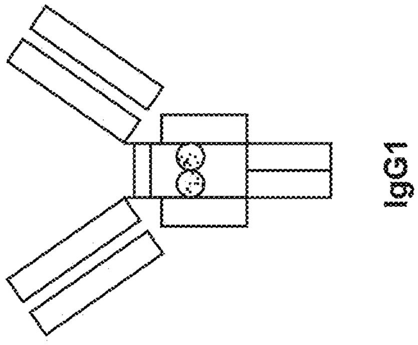
FIG. 5A depicts a drawing of an intact IgG1 antibody showing both Fab arms, hinge region, and two Fc domains each comprising a canonical $Asn^{297}$ (N-297) glycan on each CH2 wherein the glycans are packed within the internal space enclosed by the CH2 domains and the CH2 domains from two polypeptide chains make no direct interactions due to the carbohydrate moieties.
Figure 5B:
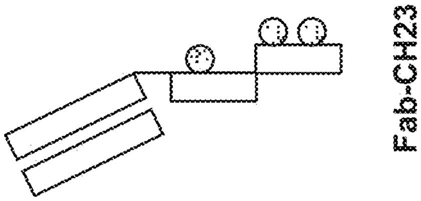
FIG. 5B depicts a drawing illustrating a monomeric Fc-containing polypeptide comprising a single Fab and comprising the canonical $Asn^{297}$ glycan in the CH2 domain and two engineered glycosylation sites in the CH3 domain.
Figure 5C:
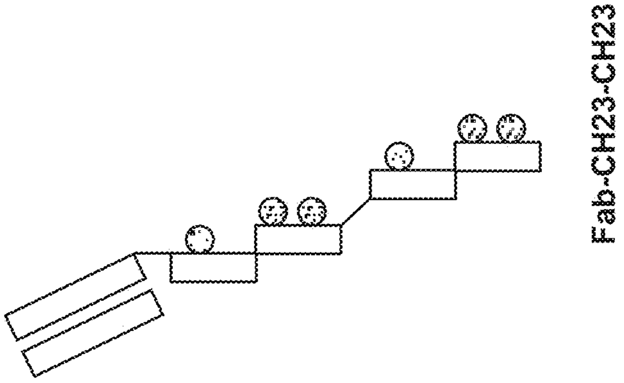
FIG. 5C depicts a drawing illustrating a monomeric Fc-containing polypeptide wherein the polypeptide comprises two recombinantly linked monomeric Fc-containing polypeptides wherein each Fc-domain comprises two engineered glycosylation sites in each CH3 domain in addition to comprising a canonical $Asn^{297}$ glycan in the CH2 domain.

In order to elucidate the FcRn involvement in serum lifetime of CH23, a Fab fragment derived from an anti-KLH antibody was fused to CH23 (referred to herein as "Fab-CH23" which is also referred to as Fab-CH23-N364/N407 (S364N-L355-T366 and Y407N-S408-K409T (e.g., SEQ ID NO: 71)). The same Fab fragment was also fused to the FcRn knock-out variant (Fab-CH23[H310A/H433A] (e.g., SEQ ID NO: 75)) and to the FcRn enhancement variant (Fab-CH23[M428L/N434S] (e.g., SEQ ID NO: 73)). A tandem CH23 construct (Fab-CH23-CH23 (e.g., SEQ ID NO: 85)) comprising two engineered Fc polypeptides was also constructed as well as regular IgG1 format control (that is, anti-KLH antibody) to test the hypothesis that avidity might improve the pharmacokinetic property of CH23 (FIG. 5). All the constructs were transfected into CHO cells, and proteins were purified by protein G column chromatography. As a control, Fab-CH23 produced in a HEK293 cell transient expression system (termed "Fab-CH23-HEK") was produced. FcRn binding of these constructs in both a 1-to-1 binding format ("Fc variant" bound to the surface of a BIAcore chip and soluble FcRn floated over the chip surface) and an avidity format (mouse FcRn protein bound to the BIAcore chip surface and each Fc variant floated over the chip) were investigated. The equilibrium binding data are summarized in Table 4. The 1-to-1 binding affinity of either Fab-CH23 or Fab-CH23-HEK (Table 4) was similar to that of CH23-N364/N407 (Table 1), suggesting that Fab fusion did not affect Fc binding to FcRn. As expected, higher binding affinity for FcRn was observed for Fab-CH23[M428L/N434S] while no FcRn binding was observed for Fab-CH23[H310A/H433A]. In the 1-to-1 binding assay, Fab-CH23-CH23 localized on the chip surface showed a similar binding affinity to that of Fab-CH23 for FcRn. Surprisingly, in the avidity assay (FcRn localized on the chip surface), however, Fab-CH23-CH23 showed approximately 40-fold higher affinity binding to FcRn than Fab-CH23.

Although the architecture of IgG Fc and tandem CH23-CH23 differ, Fab-CH23-CH23 was found to bind with high affinity to FcRn localized on the biosensor surface similar to the affinity of IgG comprising a single Fc domain. In order to assess that Fab-CH23-CH23 dissociated from FcRn at neutral pH, the percent of Fab-CH23-CH23 bound at pH 7.4 and at pH 6.0 during dissociation phase was measured. It was observed that the % bound of both Fab-CH23-23 and IgG were almost the same. These results demonstrate that Fab-CH23-CH23 not only binds tightly to FcRn at acidic pH, but that it also dissociates from FcRn efficiently at neutral pH similar to wild type IgG Fc.

TABLE 4

Summary of FcRn interaction of various Fab-CH23 fusions

| Variants | Kd (1-to-1) (nM) | Kd (avidity) (nM) | % bound (%) |
|---|---|---|---|
| Fab-CH23-HEK | 230 | 180 | 1.1 |
| Fab-CH23 | 250 | 180 | 5.6 |
| Fab-CH23[H310A/H433A] | — | — | — |
| Fab-CH23[M428L/N434S] | 68 | 35 | 20 |
| Fab-CH23-CH23 | 250 | 4.5 | 14 |
| IgG | 280 | 9.3 | 11 |

Example 6: Pharmacokinetics of Fab-CH23 Variants: In Mice

Figure 6:
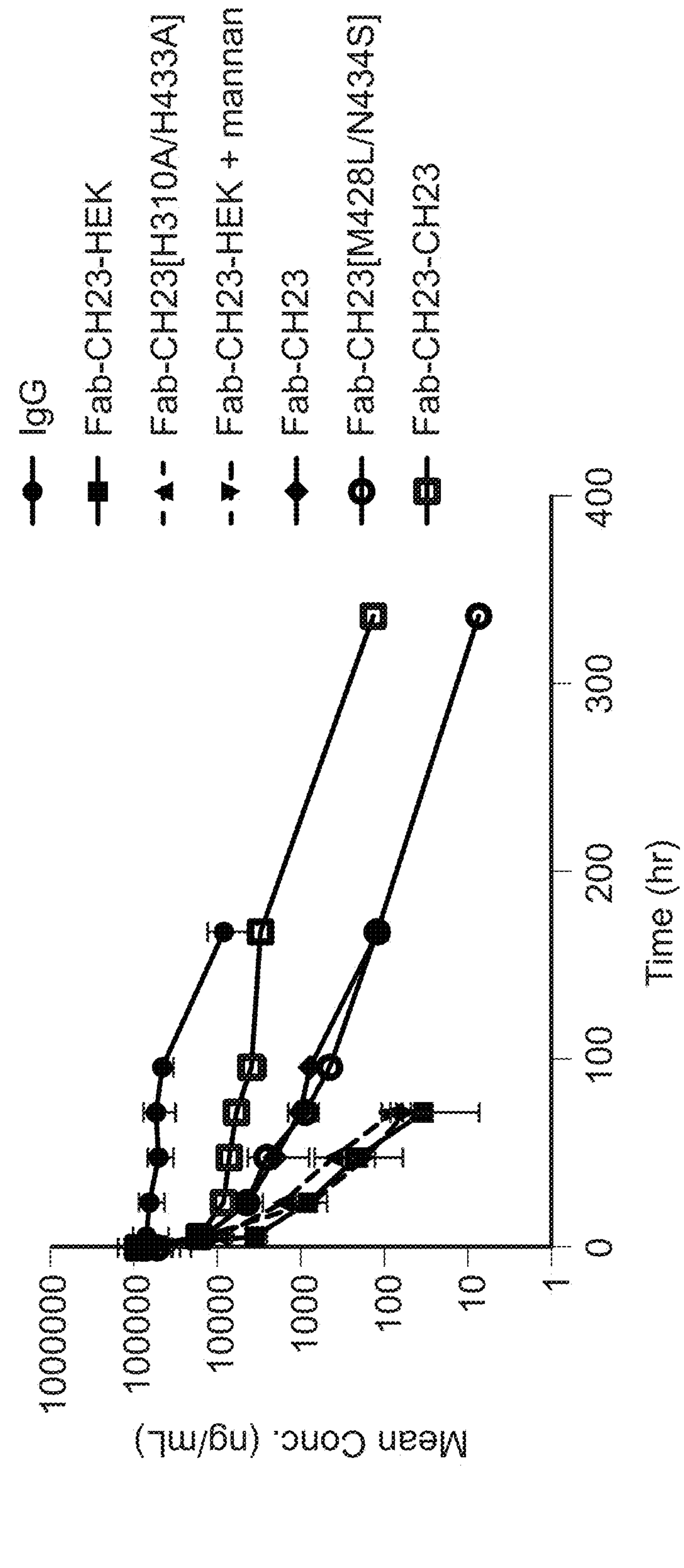
FIG. 6 depicts a graph demonstrating the pharmacokinetic characteristics of monomeric Fc-containing polypeptide variants fused to a Fab from KLH-derived antibody (referred to herein as "Fab-CH23" which is also referred to as Fab-CH23 [N364/N407]). Solid circles denote human IgG1; solid squares show PK of Fab-CH23-HEK (Fab-CH23 [N364/N407] produced from HEK293 transient expression system); solid triangles denote Fab-CH23 [H310A/H433A] (FcRn knock-out variant); up-side-down solid triangles indicate Fab-CH23-HEK+mannan (a natural inhibitor of mannose receptors); solid diamonds indicate Fab-CH23 [N364/N407] produced from stable CHO cell line; open circles indicate Fab-CH23 [M428L/N434L] (FcRn enhancement variant); and open squares indicate Fab-CH23-CH23 (a dimer or a tandem construct having two engineered CH23s [N364/N407]).

The mean plasma concentration profiles following a single IV dose of 5 mg/kg of the bivalent antibodies or monomeric Fc-containing polypeptides comprising the same Fab as the antibodies in Balb/c male mice were determined and the data are shown in FIG. 6, and the PK parameters are summarized in Table 5. The inter-subject variability was relatively high for Fab-CH23 and a significant decrease in plasma concentration was observed after 96 hours of dosing, suggesting possible immunogenicity (e.g, clearance by mouse anti-human antibodies, AHA, against the constructs). Clearance (CL) for Fab-CH23 was low and comparable to CL of typical IgGs at 0.3 mL/hr/kg, and the $T_{1/2}$ was 173 hr (~7.2 d). The CL rates for Fab-CH23-HEK and Fab-CH23 [H310A/H433A], at 18 and 14 mL/hr/kg, respectively, were much higher than that for the wild type IgG at 0.3 mL/hr. Consequently, the $T_{1/2}$ was much shorter for these two variants at 12 and 11 hours, respectively, compared with wild type IgG (173 hours). When Fab-CH23-HEK was co-administered via intraperitoneal route with 10 mg of mannan (a natural inhibitor of mannose receptors), the CL increased 2-fold compared with Fab-CH23 without mannan, which indicates that mannose receptor-mediated clearance is a major clearance mechanism of Fab-CH23-HEK. Fab-CH23 and Fab-CH23[M428L/N434S] had improved PK over Fab-CH23-HEK and Fab-CH23[H310A/H433A] with CL of ~9 mL/hr/kg and $T_{1/2}$ of 32 and 42 hr, respectively. The tandem Fab-CH23-CH23 had the slowest CL (3 mL/hrtkg) and longest $T_{1/2}$ (97 hr) among all the monomeric Fab fusions. Similar to wild type IgG, plasma concentrations of Fab-CH23-CH23 also dropped dramatically 96 hr post-dosing indicating that potential immunogenicity may also be responsible for the clearance of Fab-CH23-CH23.

TABLE 5

Pharmacokinetic parameters of various Fab-CH23 fusions

| Variants | AUCinf (μg × hr/mL) | $AUC_{Extrap}$ (%) | Co (μg/mL) | $T_{1/2}$ (hr) | CL (mL/hr/kg) | $V_{dss}$ (mL/kg) |
|---|---|---|---|---|---|---|
| Fab-CH23-HEK | 323 | 1 | 92 | 12 | 18 | 78 |
| Fab-CH23-HEK +m | 508 | 0 | 91 | 14 | 10 | 42 |
| Fab-CH23 | 579 | 1 | 70 | 32 | 9.0 | 177 |
| Fab-CH23[H310A/H433A] | 364 | 0 | 72 | 11 | 14 | 93 |
| Fab-CH23[M428L/N434S] | 548 | 1 | 58 | 42 | 9.2 | 213 |
| Fab-CH23-CH23 | 1288 | 20 | 95 | 97 | 3.0 | 323 |
| IgG | 5955 | 62 | 140 | 173 | 0.3 | 78 |

Example 7: Experimental Procedures

Plasmid Construction and Protein Expression

The expression plasmid for wild type Fc fragment was constructed as N-terminal hexa-histidine tag followed by the human gamma1 constant region starting with $Gly^{236}$. All plasmid construction and mutagenesis were carried out with In-Fusion dry-down PCR cloning kit (Clontech, Mountain View, Calif.). The mutational constructs were generated by PCR with the primers that generate desired amino acid replacements. The resulting PCR product was treated with In-Fusion cloning enhancer following by insertion into an expression vector that had been treated with XbaI and EcoRI (New England Biolab, Ipswich, Mass.). The expression vector of Fab-monoFc variants was constructed by PCR amplification of a construct encoding the Fab fragment of an anti-KLH antibody and monoFc. For protein production of N-glycosylated Fc variants, HEK293F cells were transiently transfected with the expression plasmids by using 293fectin reagent and grown in FreeStyle293 media according to the manufacturer's protocol (Invitrogen). The conditioned medium was collected by centrifugation at 2,000×g for 10 min after 6 days post transfection. For IgG and Fab-monoFc variants, CHO cells were transfected with the expression plasmids by Lipofectamine 2000 (Invitrogen, Grand Island, N.Y.). Stable clones were selected with 50 ug/mL G418 and 50 nM methotrexate for 2 to 3 weeks. The conditioned medium was collected by centrifugation and the supernatant was filtered by 0.2 um filters for subsequent purification. The expression was confirmed by SDS-PAGE under reducing conditions followed by blotting with anti-His G HRP-conjugate (Invitrogen, Grand Island, N.Y.) or anti-human Fc antibody (Sigma-Aldrich, St. Louis, Mo.).

Protein Purification

For purification of wild type Fc domain and engineered N-glycosylated Fc variants, conditioned media was loaded onto a HiTrap chelating column (GE healthcare, Piscataway, N.J.) pre-equilibrated with phosphate buffer saline (PBS) (1 mM $KH_2PO_4$, 10 mM $Na_2HPO_4$, 137 mM NaCl, and 2.7 mM KCl, pH 7.2). Nonspecific binding proteins were washed away with buffer A (1 mM $KH_2PO_4$, 10 mM $Na_2HPO_4$, 137 mM NaCl, and 2.7 mM KCl, 10 mM imidazole, pH 7.6), and protein was eluted with a linear gradient from buffer A to buffer B (1 mM $KH_2PO_4$, 10 mM $Na_2HPO_4$, 137 mM NaCl, and 2.7 mM KCl, 250 mM imidazole, pH 7.6). The pooled fraction was loaded onto HiTrap Protein A column (GE healthcare, Piscataway, N.J.) pre-equilibrated with PBS buffer and eluted with the protein A elution buffer (50 mM citric acid, pH 3.3). The resulting protein solution was neutralized by 1 M tris-HCl solution (pH 8.0), exchanged buffer to PBS, concentrated and stored at −80° C. The purity was confirmed by SDS-PAGE (4-20% linear gradient gel, Invitrogen, Grand Island, N.Y.). For Fab-monoFc variants, the conditioned media was loaded onto HiTrap Protein G column (GE healthcare, Piscataway, N.J.) pre-equilibrated with PBS buffer and eluted with the protein G elution buffer (100 mM citric acid, pH 2.5). The pooled fraction was neutralized by 1 M tris-HCl solution (pH 8.0), concentrated to 10 mL and loaded onto Superdex200 column (Hiload 26/60 prep grade, GE healthcare, Piscataway, N.J.), pre-equilibrated with PBS buffer. The purity was confirmed by SDS-PAGE and the monomeric status of N-glycosylated protein was evaluated by Superdex 200 10/300 GL (GE Healthcare, Piscataway, N.J.) using a 10×300 mm column. The purified protein solution was sterilized by 0.22 um filter and stored at −80° C. Protein quantitation was achieved by measuring the absorbance at 280 nm and calculating the concentration using the molar absorption coefficient according to Pace et al., *Protein Sci.* 4, 2411-2423 (1995).

Biophysical Characterization

Size Exclusion Chromatography-Multi-Angles Light Scattering (SEC-MALS):—Average molar mass and the oligomerization state of wild type Fc domain and engineered N-glycosylated Fc variants were determined using SEC-MALS. Protein samples were prepared at concentrations ranging from 4.5-7.0 mg/ml in PBS buffer. Each sample (200 μg) was injected onto an analytical Superdex 200 10/300 GL column (GE Healthcare, Piscataway, N.J.) connected to an Agilent 1100 HPLC system (Foster City, Calif.). Protein peaks resolved on the sizing column were analyzed using Wyatt's MiniDawn three-angle light scattering detector and Optilab-REX refractometer (Santa Barbara, Calif.) connected in line to the HPLC system. The chromatography and light scattering analysis were performed at 25° C. The MiniDawn light scattering system was calibrated according to manufacturer's instruction with toluene and normalized using bovine serum albumin (Thermo Scientific, Rockford, Ill.). Data acquisition and analysis were done using Wyatt's Astra software with a $\Delta n/\Delta c$ value of 0.185 ml/g for protein. Glycan mass contribution was determined by applying the protein conjugation template in Astra software using an approximated $\Delta n/\Delta c$ value of 0.14 ml/g for the sugar moiety.

Differential Scanning calorimetry (DSC):—Thermal stabilities of wild type Fc domain and engineered N-glycosylated Fc variants were analyzed using MicroCal's capillary DSC system, VP-DSC (Northampton, Mass.). The protein and buffer solutions were centrifuged and degassed prior to loading onto the instrument. The protein sample at a concentration of 0.02 mM in PBS buffer was placed in the sample cell. Both cells were heated from 10° C. to 100° C. at a scan rate of 100° C. per hour. The heat capacity difference between the sample cell and reference cell was recorded and analyzed using Origin7.0 software from MicroCal. A baseline thermogram was generated with PBS buffer in both the sample and reference cells. The data was used to subtract any system heat not associated with protein denaturation.

Capillary gel electrophoresis—The relative percentage of glycosylated and non-glycosylated species in each protein sample was measured under reducing condition using Caliper LabChip GXII (Hopkinton, Mass.). Deglycosylated control was prepared by incubating the protein with Glycannase F (ProZyme, Hayward, Calif.) for three hours at 37° C. in PBS buffer. Samples for the Caliper assay were prepared according to manufacturer's instruction. Briefly, 2 μl of protein sample (4.5-7.0 mg/mL) was mixed with 7 μl of SDS sample buffer and incubated at 100° C. for 5 min on a 96-well plate. The sample volume was adjusted to a final of 40 μl with de-ionized water. Protein loading, separation, staining and destaining were performed on a quartz chip photo-etched with microchannels according to the LabChip Protein Express program. An electropherogram was generated for each sample and analyzed using LabChip GX v.3.0 software.

FcRn Binding Assays

The FcRn binding assays were carried out using a surface plasmon resonance (SPR) biosensor, Biacore 3000 (Biacore, Uppsala, Sweden). The sensor chip CM5, surfactant P20, N-ethyl-N-(3-dimethylaminopropyl)carbodiimide (EDC), N-hydroxysuccinimide (NHS), and 1 M ethanolamine (pH 8.5) were purchased from GE Healthcare (Piscataway, N.J.). The SPR experiments were conducted at 25° C. in PBS buffer (pH 6.0) with 0.005% P20. A Mouse FcRn protein was purchased from ARVYS Proteins, Inc. (Stamford, Conn.). All the experiments were repeated three times.

1-to-1 binding Assay—Immobilization of engineered N-glycosylated Fc variants or Fab-mono engineered N-glycosylated Fc variants on a CM5 sensor chip was conducted by the amine coupling method. Briefly, 20 μM protein solution was diluted 20 times in 10 mM acetate (pH 4.5) and injected onto a biosensor surface which had been preactivated with a 20 uL injection of 1:1 mixture of 200 mM EDC and 50 mM NHS, followed by the injection of 1 M ethanolamine-HCl (pH 8.5). For reference surface, one flow cell was activated by the EDC-NHS mixture and deactivated by ethanol amine without protein. The equilibrium binding was measured by injecting 150 uL of soluble mouse FcRn protein at flow rate of 5 uL/min. The sensor surfaces were regenerated by running PBS buffer (pH 7.2) for 1 min. We observed that all the binding curves of each concentration reached the plateau at the end of injection (30 min). Steady-state RUs were recorded at the end of the injection (28 min), and the equilibrium dissociation constant (Kd) was calculated using the BIAevaluation software (GE Healthcare, Piscataway, N.J.).

Avidity Assay: —In order to assess the avidity of analyte (molecule in mobile phase), the SPR-based "avidity assay format" was performed as previously described. See, e.g., Zalevsky et al., *Nature Biotech.* 28, 157-159; Yeung et al., *J. Immunol.* 182, 7663-7671 (2009); and Suzuki et al., *J. Immunol.* 184, 1968-1976 (2010). That is, mouse FcRn protein was immobilized on a CM5 sensor chip by the amine coupling method as described above. The equilibrium binding was measured by injecting 30 μL, of Fab-monoFc variants over the FcRn surface at flow rate of 2 μL/min. The sensor surfaces were regenerated by running 100 mM tris-HCl, pH 8.0 for 1 min. Steady-state RUs were recorded at the end of the injection (14 min), and the equilibrium binding constant (Kd) was calculated using the BIAevaluation software (GE Healthcare, Piscataway, N.J.).

pH-Switch Assay: In order to evaluate the efficiency of dissociation of Fab-monoFc variants from FcRn at neutral pH, the "pH-switch assay" modified from the method that was previously reported was employed. See, e.g., Wang et al., *Drug Metab. Dispos.* 39, 1469-1477 (2011). In this assay, mouse FcRn protein was immobilized on a CM5 sensor chip by the amine coupling method. The binding was measured by injecting 100 uM of Fab-monoFc variants in running buffer (PBS, pH 6.0) followed by injection of either running buffer (PBS, pH 6.0) or neutral buffer (PBS, pH 7.2) alone over the FcRn surface at flow rate of 50 μL/min.

Crystallization and Structure Determination

Protein was concentrated to 30 mg/ml in tris buffer (25 mM tris-HCl, 150 mM NaCl, pH 7.5) for crystallization trials of monoFc (Fc-CH23-N364/N407). Crystallization was performed using the hanging-drop vapor diffusion method at 18° C., with the drops containing 0.2 μL, of protein solution and 0.2 μL, of reservoir solution equilibrated against the reservoir solution. Large trigonal crystals were obtained using 2.2 M ammonium sulfate and 200 mM sodium fluoride as a precipitant. Crystals were cryo-protected in the presence of 20% glycerol in the mother liquor and immediately flash-cooled in liquid nitrogen. X-ray diffraction data were collected from a single crystal up to 1.9 Å resolution on the SER-CAT beamline 22-ID, Advanced Photon Source (APS), Argonne, Ill. The data were indexed, integrated, and scaled with HKL2000 (the statistics are given in Table 2). The crystals belonged to the space group $P3_12$, with cell dimensions of a=b=64.22 Å and c=146.94 Å. The structure was solved by molecular replacement with PHASER using the crystal structure of a mutated, ADCC-enhanced human Fc domain (PDB ID: 2QL1) (Oganesyan et al., *Mol. Immunol.* 45, 1872-1882 (2008)) as a search model. After the monoFc monomer was located, the initial model was subjected to minimization with BUSTER and was further rebuilt using COOT (A Molecular Graphics Program). Several rounds of refinement alternating with rebuilding produced the final refined model corresponding to an $R_{cryst}$ of 0.25 and $R_{free}$ of 0.259 (the refinement statistics are given in Table 6).

TABLE 6

Summary of SEC-MALS data

| N-glycosylated Fc variants | | Theoretical MW (Da) | Protein Mass (Da) | Glycan Mass (Da) |
|---|---|---|---|---|
| wild type Fc | Monomer | 25,010 | None | None |
| | Dimer | 50,020 | 51,860 | 5,958 |
| Fc-N364 | Monomer | 25,037 | 28,390 | 5,062 |
| | Dimer | 50,074 | 47,490 | 3,161 |
| Fc-N368 | Monomer | 24,984 | 29,370 | 5,539 |
| | Dimer | 49,964 | 42,110 | 2,939 |
| Fc-N405 | Monomer | 24,915 | 27,090 | 4,389 |
| | Dimer | 49,830 | None | None |
| Fc-N407* | Monomer | 24,934 | 32,640 | 5,421 |
| | Dimer | 49,868 | 33,580 | 5,584 |
| Fc-N364/N407 | Monomer | 24,963 | 29,270 | 6,392 |
| | Dimer | 49,926 | None | None |

*Two broad peaks were observed with average molecular mass between monomer and dimer

#Analytical SEC-MALS with embedded reflective index and UV detectors was used in the determination of molar mass of monomer and dimer as well as protein and glycan Pharmacokinetics Study in Mice Animal studies—Male Balb/c mice (~8 week old males) were purchased from Charles River (Wilmington, Mass.). All studies were performed in accordance with the National Institutes of Health guide for the care and use of animal resources. Six mice per group received a single dose of Fab-monoFc variants via intravenous route. The administered dose of 5 mg/kg was based on the most recent scheduled body weights. The test samples were prepared in PBS and the dosing volume was 4 mL/kg. At 0, 10 min, 6, 24 hr, 2, 3, 4, 7, 14 and 21 days post dose, blood samples of 10 μL were collected from the tail vein via capillary tubes and immediately diluted in 90 μl of Rexxip A buffer (Gyros AB, Uppsala, Sweden). The sample was centrifuged at 3000×g for 10 minutes at 4° C. and supernatant was transferred to another tube and frozen at −80° C. for future analysis.

Sample Analysis—Test samples were quantitated using biotinylated goat anti-human IgG (Bethyl Laboratories) captured onto streptavidin coated beads (affinity capture column of the Gyrolab CD microstructure). The reference standards and quality controls were prepared in Rexxip A buffer, and the study samples were diluted into the assay range of quantitation. After being captured onto the affinity capture column, bound Fab-monoFc variants or bivalent wild type IgG were detected with Alexa647 labeled goat anti-human IgG (Molecular Probes). The fluorescent signal on the column allowed for detection of the bound variants. Response Units were read by the Gyrolab instrument at a 1% photomultiplier tube setting. Sample concentrations were determined by interpolation from a standard curve that was fit using a 5-parameter logistic curve fit with $1/y^2$ response weighting in Watson (Version 7.4). The assay range of quantitation for Fab-monoFc variants was 10.0 μg/mL to 41.0 ng/mL in 100% Balb/c mouse plasma. The assay range of quantitation for the bivalent IgG variant was 4.0 μg/mL to 16.3 ng/ml in 100% Balb/c mouse plasma.

Pharmacokinetic analysis—Plasma pharmacokinetic parameters for Fab-engineered N-glycosylation monoFc variants were calculated using non-compartmental methods with the aid of Watson (Version 7.4). Data in the terminal log-linear phase were analyzed by linear regression to estimate the terminal rate constant (k) and half-life ($T_{1/2}$=0.693/k). At least the last three time points were used to calculate k. Total $AUC_{inf}$ was determined as the sum of $AUC_{0\text{-}last}$ and $AUC_{extrap}$, where $AUC_{0\text{-}last}$ was calculated from 0 to the last time point ($T_{last}$) with the last measurable concentration ($C_{last}$) using the linear trapezoidal rule and $AUC_{extrap}$ was the extrapolated portion of the area from $T_{last}$ to infinite using $C_{last}$/k. Total body clearance (CL) based on plasma concentrations was calculated as dose/$AUC_{inf}$, and the volume of distribution at steady-state ($V_{dss}$) was calculated as CL×AUMC/AUC, where AUMC was the area under the first moment curve. The inter-subject variability was relatively higher for IgG than for other constructs.

SEQ LIST Table

In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 1 | hIgG1<br>From residue<br>344- | REPQVYT LPPSRDELTK NQVSLTCLVK GFYPSDIAVE WESNGQPENN<br>YKTTPPVLDS DGSFFLYSKL TVDKSRWQQG NVFSCSVMHE ALHNHYTQKS<br>LSLSPGK |
| 2 | hIgG2<br>From residue<br>344- | REPQVYT LPPSREEMTK NQVSLTCLVK GFYPSDISVE WESNGQPENN<br>YKTTPPMLDS DGSFFLYSKL TVDKSRWQQG NVFSCSVMHE ALHNHYTQKS<br>LSLSPGK |
| 3 | hIgG3<br>From residue<br>344- | REPQVYT LPPSQEEMTK NQVSLTCLVK GFYPSDIAVE WESNGQPENN<br>YKTTPPVLDS DGSFFLYSRL TVDKSRWQEG NVFSCSVMHE ALHNHYTQKS<br>LSLSLGK |
| 4 | hIgG4<br>From residue<br>344- | REPQVYT LPPSQEEMTK NQVSLTCLVK GFYPSDIAVE WESNGQPENN<br>YKTTPPVLDS DGSFFLYSRL TVDKSRWQEG NVFSCSVMHE ALHNHYTQKS<br>LSLSLGK |
| 5 | mIgG1<br>From residue<br>344- | KAPQVYT IPPPKEQMAK DKVSLTCMIT DFFPEDITVE WQWNGQPAEN<br>YKNTQPIMNT NGSYFVYSKL NVQKSNWEAG NTFTCSVLHE GLHNHHTEKS<br>LSHSPGK |
| 6 | mIG2A<br>From residue<br>344- | RAPQVYV LPPPEEEMTK KQVTLTCMVT DFMPEDIYVE WTNNGKTELN<br>YKNTEPVLDS DGSYFMYSKL RVEKKNWVER NSYSCSVVHE GLHNHHTTKS<br>FSRTPGK |
| 7 | mIG2B<br>From residue<br>344- | RAPQVYI LPPPAEQLSR KDVSLTCLVV GFNPGDISVE WTSNGHTEEN<br>YKDTAPVLDS DGSYFIYSKL NMKTSKWEKT DSFSCNVRHE GLKNYYLKKT<br>ISRSPGK |
| 8 | mIgG3<br>From residue<br>344- | QTPQVYT IPPPREQMSK KKVSLTCLVT NFFSEAISVE WERNGELEQD<br>YKNTPPILDS DGTYFLYSKL TVDTDSWLQG EIFTCSVVHE ALHNHHTQKN<br>LSRSPGK |
| 9 | hIgG1<br>From residue<br>396- | GGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQP |
| 10 | hIgG2<br>From residue<br>396- | AGPSV FLFPPKPKDT LMISRTPEVT CVVVDVSHED PEVQFNWYVD<br>GVEVHNAKTK PREEQFNSTF RVVSVLTVVH QDWLNGKEYK CKVSNKGLPA<br>PIEKTISKTK GQP |
| 11 | hIgG3<br>From residue<br>396- | GGPSV FLFPPKPKDT LMISRTPEVT CVVVDVSHED PEVQFKWYVD<br>GVEVHNAKTK PREEQYNSTF RVVSVLTVLH QDWLNGKEYK CKVSNKALPA<br>PIEKTISKTK GQP |
| 12 | hIgG4<br>From residue<br>396- | GGPSV FLFPPKPKDT LMISRTPEVT CVVVDVSQED PEVQFNWYVD<br>GVEVHNAKTK PREEQFNSTY RVVSVLTVLH QDWLNGKEYK CKVSNKGLPS<br>SIEKTISKAK GQP |
| 13 | mIgG1<br>From residue<br>396- | EVSSV FIFPPKPKDV LTITLTPKVT CVVVDISKDD PEVQFSWFVD<br>DVEVHTAQTQ PREEQFNSTF RSVSELPIMH QDWLNGKEFK CRVNSAAFPA<br>PIEKTISKTK GRP |
| 14 | mIG2A<br>From residue<br>396- | GGPSV FIFPPKIKDV LMISLSPIVT CVVVDVSEDD PDVQISWFVN<br>NVEVHTAQTQ THREDYNSTL RVVSALPIQH QDWMSGKEFK CKVNNKDLPA<br>PIERT ISKPKGSV |
| 15 | mIG2B<br>From residue<br>396- | GGPSV FIFPPNIKDV LMISLTPKVT CVVVDVSEDD PDVQISWFVN<br>NVEVHTAQTQ THREDYNSTI RVVSTLPIQH QDWMSGKEFK CKVNNKDLPS<br>PIERTISKIK GLV |
| 16 | mIgG3<br>From residue<br>396- | GGPSV FIFPPKPKDA LMISLTPKVT CVVVDVSEDD PDVHVSWFVD<br>NKEVHTAWTQ PREAQYNSTF RVVSALPIQH QDWMRGKEFK CKVNNKALPA<br>PIERTISKPK GRA |
| 17 | CH23 variants:<br>Protein<br>IgG1-CH23-N347 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPNVT TLPPSREEMT<br>KNQVSLTCLV KGFYPSDIAV EWESNGQPEN NYKTTPPVLD SDGSFFLYSK<br>LTVDKSRWQQ GNVFSCSVMH EALHNHYTQK SLSLSPGK |

-continued

| SEQ LIST Table |
|---|
| In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker. |

| SEQ ID NO: | DETAILS | |
|---|---|---|
| 18 | CH23 variants:<br>DNA<br>IgG1-CH23-N347 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC A**AAC**GTG**ACC** ACCCTGCCCC CATCCCGGGA GGAGATGACC<br>AAGAACCAGG TCAGCCTGAC CTGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTATAGCAAG<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 19 | CH23 variants:<br>Protein<br>IgG1-CH23-N364 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQV**NLT**CLV KGFYPSDIAV EWESNGQPEN NYKTTPPVLD SDGSFFLYSK<br>LTVDKSRWQQ GNVFSCSVMH EALHNHYTQK SLSLSPGK |
| 20 | CH23 variants:<br>DNA<br>IgG1-CH23-N364 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TC**AAC**CTG**AC** **C**TGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTATAGCAAG<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 21 | CH23 variants:<br>Protein<br>IgG1-CH23-N366 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQVSL**NCT**V KGFYPSDIAV EWESNGQPEN NYKTTPPVLD SDGSFFLYSK<br>LTVDKSRWQQ GNVFSCSVMH EALHNHYTQK SLSLSPGK |
| 22 | CH23 variants:<br>DNA<br>IgG1-CH23-N366 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TCAGCCTG**AA** **C**TGC**ACC**GTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTATAGCAAG<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 23 | CH23 variants:<br>Protein<br>IgG1-CH23-N368 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQVSLTC**N**V **T**GFYPSDIAV EWESNGQPEN NYKTTPPVLD SDGSFFLYSK<br>LTVDKSRWQQ GNVFSCSVMH EALHNHYTQK SLSLSPGK |

-continued

SEQ LIST Table
In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 24 | CH23 variants:<br>DNA<br>IgG1-CH23-N368 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TCAGCCTGAC CTGC**AAC**GTC **ACC**GGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTATAGCAAG<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 25 | CH23 variants:<br>Protein<br>IgG1-CH23-N390 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQVSLTCLV KGFYPSDIAV EWESNGQPE**N** NY**T**TTPPVLD SDGSFFLYSK<br>LTVDKSRWQQ GNVFSCSVMH EALHNHYTQK SLSLSPGK |
| 26 | CH23 variants:<br>DNA<br>IgG1-CH23-N390 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TCAGCCTGAC CTGCCTGGTC AAAGGCTTCT ATCCCAGCGA<br>CATCGCCGTG GAGTGGGAGA GCAATGGGCA GCCGGAGAAC **AAC**TAC**ACC**A<br>CCACGCCTCC CGTGCTGGAC TCCGACGGCT CCTTCTTCCT CTATAGCAAG<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 27 | CH23 variants:<br>Protein<br>IgG1-CH23-N401 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQVSLTCLV KGFYPSDIAV EWESNGQPEN NYKTTPPVLD S**NGT**FFLYSK<br>LTVDKSRWQQ GNVFSCSVMH EALHNHYTQK SLSLSPGK |
| 28 | CH23 variants:<br>DNA<br>IgG1-CH23-N401 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TCAGCCTGAC CTGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCC**AAC**GGC**A** **CC**TTCTTCCT CTATAGCAAG<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 29 | CH23 variants:<br>Protein<br>IgG1-CH23-N405 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQVSLTCLV KGFYPSDIAV EWESNGQPEN NYKTTPPVLD SDGSF**NLT**SK<br>LTVDKSRWQQ GNVFSCSVMH EALHNHYTQK SLSLSPGK |

-continued

SEQ LIST Table

In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 30 | CH23 variants:<br>DNA<br>IgG1-CH23-N405 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TCAGCCTGAC CTGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTC**AAC**CT C**ACC**AGCAAG<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 31 | CH23 variants:<br>Protein<br>IgG1-CH23-N407 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQVSLTCLV KGFYPSDIAV EWESNGQPEN NYKTTPPVLD SDGSFFL**N**S**T**<br>LTVDKSRWQQ GNVFSCSVMH EALHNHYTQK SLSLSPGK |
| 32 | CH23 variants:<br>DNA<br>IgG1-CH23-N407 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TCAGCCTGAC CTGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT C**AAC**AGC**ACC**<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 33 | CH23 variants:<br>Protein<br>IgG1-CH23-N409 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQVSLTCLV KGFYPSDIAV EWESNGQPEN NYKTTPPVLD SDGSFFLYS**N**<br>L**T**VDKSRWQQ GNVFSCSVMH EALHNHYTQK SLSLSPGK |
| 34 | CH23 variants:<br>DNA<br>IgG1-CH23-N409 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TCAGCCTGAC CTGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTATAGC**AAC**<br>CTC**ACC**GTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 35 | CH23 variants:<br>Protein<br>IgG4-CH23-N347 | MKAVVLAVAL VFLTGSQARH HHHHHGGGPS VFLFPPKPKD TLMISRTPEV<br>TCVVVDVSQE DPEVQFNWYV DGVEVHNAKT KPREEQFNST YRVVSVLTVL<br>HQDWLNGKEY KCKVSNKGLP SSIEKTISKA KGQPREP**NVT** TLPPSQEEMT<br>KNQVSLTCLV KGFYPSDIAV EWESNGQPEN NYKTTPPVLD SDGSFFLYSR<br>LTVDKSRWQE GNVFSCSVMH EALHNHYTQK SLSLSLGK |

-continued

SEQ LIST Table

In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 36 | CH23 variants:<br>DNA<br>IgG4-CH23-N347 | ATGAAAGCTG TGGTGCTGGC CGTGGCTCTG GTCTTCCTGA CAGGGAGCCA<br>GGCTCGGCAT CATCATCACC ATCACGGCGG GGGACCATCA GTCTTCCTGT<br>TCCCCCCAAA ACCCAAGGAC ACTCTCATGA TCTCCCGGAC CCCTGAGGTC<br>ACGTGCGTGG TGGTGGACGT GAGCCAGGAA GACCCCGAGG TCCAGTTCAA<br>CTGGTACGTG GATGGCGTGG AGGTGCATAA TGCCAAGACA AAGCCGCGGG<br>AGGAGCAGTT CAACAGCACG TACCGTGTGG TCAGCGTCCT CACCGTCCTG<br>CACCAGGACT GGCTGAACGG CAAGGAGTAC AAGTGCAAGG TCTCCAACAA<br>AGGCCTCCCG TCCTCCATCG AGAAAACCAT CTCCAAAGCC AAAGGTCAGC<br>CCCGAGAGCC A**AAC**GTG**ACC** ACCCTGCCCC CATCCCAGGA GGAGATGACC<br>AAGAACCAGG TCAGCCTGAC CTGCCTGGTC AAAGGCTTCT ACCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTACAGCAGG<br>CTAACCGTGG ACAAGAGCAG GTGGCAGGAG GGGAATGTCT TCTCATGCTC<br>CGTGATGCAT GAGGCTCTGC ACAACCACTA CACACAGAAG AGCCTCTCCC<br>TGTCTCTGGG TAAATGA |
| 37 | CH23 variants:<br>Protein<br>IgG4-CH23-N364 | MKAVVLAVAL VFLTGSQARH HHHHHGGGPS VFLFPPKPKD TLMISRTPEV<br>TCVVVDVSQE DPEVQFNWYV DGVEVHNAKT KPREEQFNST YRVVSVLTVL<br>HQDWLNGKEY KCKVSNKGLP SSIEKTISKA KGQPREPQVY TLPPSQEEMT<br>KNQV**NLT**CLV KGFYPSDIAV EWESNGQPEN NYKTTPPVLD SDGSFFLYSR<br>LTVDKSRWQE GNVFSCSVMH EALHNHYTQK SLSLSLGK |
| 38 | CH23 variants:<br>DNA<br>IgG4-CH23-N364 | ATGAAAGCTG TGGTGCTGGC CGTGGCTCTG GTCTTCCTGA CAGGGAGCCA<br>GGCTCGGCAT CATCATCACC ATCACGGCGG GGGACCATCA GTCTTCCTGT<br>TCCCCCCAAA ACCCAAGGAC ACTCTCATGA TCTCCCGGAC CCCTGAGGTC<br>ACGTGCGTGG TGGTGGACGT GAGCCAGGAA GACCCCGAGG TCCAGTTCAA<br>CTGGTACGTG GATGGCGTGG AGGTGCATAA TGCCAAGACA AAGCCGCGGG<br>AGGAGCAGTT CAACAGCACG TACCGTGTGG TCAGCGTCCT CACCGTCCTG<br>CACCAGGACT GGCTGAACGG CAAGGAGTAC AAGTGCAAGG TCTCCAACAA<br>AGGCCTCCCG TCCTCCATCG AGAAAACCAT CTCCAAAGCC AAAGGTCAGC<br>CCCGAGAGCC ACAGGTGTAC ACCCTGCCCC CATCCCAGGA GGAGATGACC<br>AAGAACCAGG TC**AAC**CTG**AC** **C**TGCCTGGTC AAAGGCTTCT ACCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTACAGCAGG<br>CTAACCGTGG ACAAGAGCAG GTGGCAGGAG GGGAATGTCT TCTCATGCTC<br>CGTGATGCAT GAGGCTCTGC ACAACCACTA CACACAGAAG AGCCTCTCCC<br>TGTCTCTGGG TAAATGA |
| 39 | CH23 variants:<br>Protein<br>IgG4-CH23-N366 | MKAVVLAVAL VFLTGSQARH HHHHHGGGPS VFLFPPKPKD TLMISRTPEV<br>TCVVVDVSQE DPEVQFNWYV DGVEVHNAKT KPREEQFNST YRVVSVLTVL<br>HQDWLNGKEY KCKVSNKGLP SSIEKTISKA KGQPREPQVY TLPPSQEEMT<br>KNQVSL**NCT**V KGFYPSDIAV EWESNGQPEN NYKTTPPVLD SDGSFFLYSR<br>LTVDKSRWQE GNVFSCSVMH EALHNHYTQK SLSLSLGK |
| 40 | CH23 variants:<br>DNA<br>IgG4-CH23-N366 | ATGAAAGCTG TGGTGCTGGC CGTGGCTCTG GTCTTCCTGA CAGGGAGCCA<br>GGCTCGGCAT CATCATCACC ATCACGGCGG GGGACCATCA GTCTTCCTGT<br>TCCCCCCAAA ACCCAAGGAC ACTCTCATGA TCTCCCGGAC CCCTGAGGTC<br>ACGTGCGTGG TGGTGGACGT GAGCCAGGAA GACCCCGAGG TCCAGTTCAA<br>CTGGTACGTG GATGGCGTGG AGGTGCATAA TGCCAAGACA AAGCCGCGGG<br>AGGAGCAGTT CAACAGCACG TACCGTGTGG TCAGCGTCCT CACCGTCCTG<br>CACCAGGACT GGCTGAACGG CAAGGAGTAC AAGTGCAAGG TCTCCAACAA<br>AGGCCTCCCG TCCTCCATCG AGAAAACCAT CTCCAAAGCC AAAGGTCAGC<br>CCCGAGAGCC ACAGGTGTAC ACCCTGCCCC CATCCCAGGA GGAGATGACC<br>AAGAACCAGG TCAGCCTG**AA** **C**TGC**ACC**GTC AAAGGCTTCT ACCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTACAGCAGG<br>CTAACCGTGG ACAAGAGCAG GTGGCAGGAG GGGAATGTCT TCTCATGCTC<br>CGTGATGCAT GAGGCTCTGC ACAACCACTA CACACAGAAG AGCCTCTCCC<br>TGTCTCTGGG TAAATGA |
| 41 | CH23 variants:<br>Protein<br>IgG4-CH23-N368 | MKAVVLAVAL VFLTGSQARH HHHHHGGGPS VFLFPPKPKD TLMISRTPEV<br>TCVVVDVSQE DPEVQFNWYV DGVEVHNAKT KPREEQFNST YRVVSVLTVL<br>HQDWLNGKEY KCKVSNKGLP SSIEKTISKA KGQPREPQVY TLPPSQEEMT<br>KNQVSLTC**N**V **T**GFYPSDIAV EWESNGQPEN NYKTTPPVLD SDGSFFLYSR<br>LTVDKSRWQE GNVFSCSVMH EALHNHYTQK SLSLSLGK |

-continued

| SEQ LIST Table<br>In SEQ ID Nos: 1-8, bold residues denote the positions rationally selected for N-glycosylation according to the present invention.<br>In SEQ ID Nos 17-88, the bold residues denote amino acid/nucleic acid variations, the first underlined region is the signal/leader sequence, and where present, the second underlined region denotes the linker. | | |
|---|---|---|
| SEQ ID NO: | DETAILS | |
| 42 | CH23 variants:<br>DNA<br>IgG4-CH23-N368 | ATGAAAGCTG TGGTGCTGGC CGTGGCTCTG GTCTTCCTGA CAGGGAGCCA<br>GGCTCGGCAT CATCATCACC ATCACGGCGG GGGACCATCA GTCTTCCTGT<br>TCCCCCCAAA ACCCAAGGAC ACTCTCATGA TCTCCCGGAC CCCTGAGGTC<br>ACGTGCGTGG TGGTGGACGT GAGCCAGGAA GACCCCGAGG TCCAGTTCAA<br>CTGGTACGTG GATGGCGTGG AGGTGCATAA TGCCAAGACA AAGCCGCGGG<br>AGGAGCAGTT CAACAGCACG TACCGTGTGG TCAGCGTCCT CACCGTCCTG<br>CACCAGGACT GGCTGAACGG CAAGGAGTAC AAGTGCAAGG TCTCCAACAA<br>AGGCCTCCCG TCCTCCATCG AGAAAACCAT CTCCAAAGCC AAAGGTCAGC<br>CCCGAGAGCC ACAGGTGTAC ACCCTGCCCC CATCCCAGGA GGAGATGACC<br>AAGAACCAGG TCAGCCTGAC CTGC**AAC**GTC **ACC**GGCTTCT ACCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTACAGCAGG<br>CTAACCGTGG ACAAGAGCAG GTGGCAGGAG GGGAATGTCT TCTCATGCTC<br>CGTGATGCAT GAGGCTCTGC ACAACCACTA CACACAGAAG AGCCTCTCCC<br>TGTCTCTGGG TAAATGA |
| 43 | CH23 variants:<br>Protein<br>IgG4-CH23-N390 | MKAVVLAVAL VFLTGSQARH HHHHHGGGPS VFLFPPKPKD TLMISRTPEV<br>TCVVVDVSQE DPEVQFNWYV DGVEVHNAKT KPREEQFNST YRVVSVLTVL<br>HQDWLNGKEY KCKVSNKGLP SSIEKTISKA KGQPREPQVY TLPPSQEEMT<br>KNQVSLTCLV KGFYPSDIAV EWESNGQPEN **N**Y**T**TTPPVLD SDGSFFLYSR<br>LTVDKSRWQE GNVFSCSVMH EALHNHYTQK SLSLSLGK |
| 44 | CH23 variants:<br>DNA<br>IgG4-CH23-N390 | ATGAAAGCTG TGGTGCTGGC CGTGGCTCTG GTCTTCCTGA CAGGGAGCCA<br>GGCTCGGCAT CATCATCACC ATCACGGCGG GGGACCATCA GTCTTCCTGT<br>TCCCCCCAAA ACCCAAGGAC ACTCTCATGA TCTCCCGGAC CCCTGAGGTC<br>ACGTGCGTGG TGGTGGACGT GAGCCAGGAA GACCCCGAGG TCCAGTTCAA<br>CTGGTACGTG GATGGCGTGG AGGTGCATAA TGCCAAGACA AAGCCGCGGG<br>AGGAGCAGTT CAACAGCACG TACCGTGTGG TCAGCGTCCT CACCGTCCTG<br>CACCAGGACT GGCTGAACGG CAAGGAGTAC AAGTGCAAGG TCTCCAACAA<br>AGGCCTCCCG TCCTCCATCG AGAAAACCAT CTCCAAAGCC AAAGGTCAGC<br>CCCGAGAGCC ACAGGTGTAC ACCCTGCCCC CATCCCAGGA GGAGATGACC<br>AAGAACCAGG TCAGCCTGAC CTGCCTGGTC AAAGGCTTCT ACCCCAGCGA<br>CATCGCCGTG GAGTGGGAGA GCAATGGGCA GCCGGAGAAC **AAC**TAC**ACC**A<br>CCACGCCTCC CGTGCTGGAC TCCGACGGCT CCTTCTTCCT CTACAGCAGG<br>CTAACCGTGG ACAAGAGCAG GTGGCAGGAG GGGAATGTCT TCTCATGCTC<br>CGTGATGCAT GAGGCTCTGC ACAACCACTA CACACAGAAG AGCCTCTCCC<br>TGTCTCTGGG TAAATGA |
| 45 | CH23 variants:<br>Protein<br>IgG4-CH23-N401 | MKAVVLAVAL VFLTGSQARH HHHHHGGGPS VFLFPPKPKD TLMISRTPEV<br>TCVVVDVSQE DPEVQFNWYV DGVEVHNAKT KPREEQFNST YRVVSVLTVL<br>HQDWLNGKEY KCKVSNKGLP SSIEKTISKA KGQPREPQVY TLPPSQEEMT<br>KNQVSLTCLV KGFYPSDIAV EWESNGQPEN NYKTTPPVLD S**N**G**T**FFLYSR<br>LTVDKSRWQE GNVFSCSVMH EALHNHYTQK SLSLSLGK |
| 46 | CH23 variants:<br>DNA<br>IgG4-CH23-N401 | ATGAAAGCTG TGGTGCTGGC CGTGGCTCTG GTCTTCCTGA CAGGGAGCCA<br>GGCTCGGCAT CATCATCACC ATCACGGCGG GGGACCATCA GTCTTCCTGT<br>TCCCCCCAAA ACCCAAGGAC ACTCTCATGA TCTCCCGGAC CCCTGAGGTC<br>ACGTGCGTGG TGGTGGACGT GAGCCAGGAA GACCCCGAGG TCCAGTTCAA<br>CTGGTACGTG GATGGCGTGG AGGTGCATAA TGCCAAGACA AAGCCGCGGG<br>AGGAGCAGTT CAACAGCACG TACCGTGTGG TCAGCGTCCT CACCGTCCTG<br>CACCAGGACT GGCTGAACGG CAAGGAGTAC AAGTGCAAGG TCTCCAACAA<br>AGGCCTCCCG TCCTCCATCG AGAAAACCAT CTCCAAAGCC AAAGGTCAGC<br>CCCGAGAGCC ACAGGTGTAC ACCCTGCCCC CATCCCAGGA GGAGATGACC<br>AAGAACCAGG TCAGCCTGAC CTGCCTGGTC AAAGGCTTCT ACCCCAGCGA<br>CATCGCCGTG GAGTGGGAGA GCAATGGGCA GCCGGAGAAC AACTACAAGA<br>CCACGCCTCC CGTGCTGGAC TCC**AAC**GGC**A** **CC**TTCTTCCT CTACAGCAGG<br>CTAACCGTGG ACAAGAGCAG GTGGCAGGAG GGGAATGTCT TCTCATGCTC<br>CGTGATGCAT GAGGCTCTGC ACAACCACTA CACACAGAAG AGCCTCTCCC<br>TGTCTCTGGG TAAATGA |
| 47 | CH23 variants:<br>Protein<br>IgG4-CH23-N405 | MKAVVLAVAL VFLTGSQARH HHHHHGGGPS VFLFPPKPKD TLMISRTPEV<br>TCVVVDVSQE DPEVQFNWYV DGVEVHNAKT KPREEQFNST YRVVSVLTVL<br>HQDWLNGKEY KCKVSNKGLP SSIEKTISKA KGQPREPQVY TLPPSQEEMT<br>KNQVSLTCLV KGFYPSDIAV EWESNGQPEN NYKTTPPVLD SDGSF**N**L**T**SR<br>LTVDKSRWQE GNVFSCSVMH EALHNHYTQK SLSLSLGK |

-continued

SEQ LIST Table
In SEQ ID Nos: 1-8, bold residues denote the positions rationally selected for N-glycosylation according to the present invention.
In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 48 | CH23 variants:<br>DNA<br>IgG4-CH23-N405 | ATGAAAGCTG TGGTGCTGGC CGTGGCTCTG GTCTTCCTGA CAGGGAGCCA<br>GGCTCGGCAT CATCATCACC ATCACGGCGG GGGACCATCA GTCTTCCTGT<br>TCCCCCCAAA ACCCAAGGAC ACTCTCATGA TCTCCCGGAC CCCTGAGGTC<br>ACGTGCGTGG TGGTGGACGT GAGCCAGGAA GACCCCGAGG TCCAGTTCAA<br>CTGGTACGTG GATGGCGTGG AGGTGCATAA TGCCAAGACA AAGCCGCGGG<br>AGGAGCAGTT CAACAGCACG TACCGTGTGG TCAGCGTCCT CACCGTCCTG<br>CACCAGGACT GGCTGAACGG CAAGGAGTAC AAGTGCAAGG TCTCCAACAA<br>AGGCCTCCCG TCCTCCATCG AGAAAACCAT CTCCAAAGCC AAAGGTCAGC<br>CCCGAGAGCC ACAGGTGTAC ACCCTGCCCC CATCCCAGGA GGAGATGACC<br>AAGAACCAGG TCAGCCTGAC CTGCCTGGTC AAAGGCTTCT ACCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTC**AAC**CT C**ACC**AGCAGG<br>CTAACCGTGG ACAAGAGCAG GTGGCAGGAG GGGAATGTCT TCTCATGCTC<br>CGTGATGCAT GAGGCTCTGC ACAACCACTA CACACAGAAG AGCCTCTCCC<br>TGTCTCTGGG TAAATGA |
| 49 | CH23 variants:<br>Protein<br>IgG4-CH23-N407 | MKAVVLAVAL VFLTGSQARH HHHHHGGGPS VFLFPPKPKD TLMISRTPEV<br>TCVVVDVSQE DPEVQFNWYV DGVEVHNAKT KPREEQFNST YRVVSVLTVL<br>HQDWLNGKEY KCKVSNKGLP SSIEKTISKA KGQPREPQVY TLPPSQEEMT<br>KNQVSLTCLV KGFYPSDIAV EWESNGQPEN NYKTTPPVLD SDGSFFL**N**S**T**<br>LTVDKSRWQE GNVFSCSVMH EALHNHYTQK SLSLSLGK |
| 50 | CH23 variants:<br>DNA<br>IgG4-CH23-N407 | ATGAAAGCTG TGGTGCTGGC CGTGGCTCTG GTCTTCCTGA CAGGGAGCCA<br>GGCTCGGCAT CATCATCACC ATCACGGCGG GGGACCATCA GTCTTCCTGT<br>TCCCCCCAAA ACCCAAGGAC ACTCTCATGA TCTCCCGGAC CCCTGAGGTC<br>ACGTGCGTGG TGGTGGACGT GAGCCAGGAA GACCCCGAGG TCCAGTTCAA<br>CTGGTACGTG GATGGCGTGG AGGTGCATAA TGCCAAGACA AAGCCGCGGG<br>AGGAGCAGTT CAACAGCACG TACCGTGTGG TCAGCGTCCT CACCGTCCTG<br>CACCAGGACT GGCTGAACGG CAAGGAGTAC AAGTGCAAGG TCTCCAACAA<br>AGGCCTCCCG TCCTCCATCG AGAAAACCAT CTCCAAAGCC AAAGGTCAGC<br>CCCGAGAGCC ACAGGTGTAC ACCCTGCCCC CATCCCAGGA GGAGATGACC<br>AAGAACCAGG TCAGCCTGAC CTGCCTGGTC AAAGGCTTCT ACCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT C**AAC**AGC**ACC**<br>CTAACCGTGG ACAAGAGCAG GTGGCAGGAG GGGAATGTCT TCTCATGCTC<br>CGTGATGCAT GAGGCTCTGC ACAACCACTA CACACAGAAG AGCCTCTCCC<br>TGTCTCTGGG TAAATGA |
| 51 | CH23 variants:<br>Protein<br>IgG4-CH23-N409 | MKAVVLAVAL VFLTGSQARH HHHHHGGGPS VFLFPPKPKD TLMISRTPEV<br>TCVVVDVSQE DPEVQFNWYV DGVEVHNAKT KPREEQFNST YRVVSVLTVL<br>HQDWLNGKEY KCKVSNKGLP SSIEKTISKA KGQPREPQVY TLPPSQEEMT<br>KNQVSLTCLV KGFYPSDIAV EWESNGQPEN NYKTTPPVLD SDGSFFLYS**N**<br>L**T**VDKSRWQE GNVFSCSVMH EALHNHYTQK SLSLSLGK |
| 52 | CH23 variants:<br>DNA<br>IgG4-CH23-N409 | ATGAAAGCTG TGGTGCTGGC CGTGGCTCTG GTCTTCCTGA CAGGGAGCCA<br>GGCTCGGCAT CATCATCACC ATCACGGCGG GGGACCATCA GTCTTCCTGT<br>TCCCCCCAAA ACCCAAGGAC ACTCTCATGA TCTCCCGGAC CCCTGAGGTC<br>ACGTGCGTGG TGGTGGACGT GAGCCAGGAA GACCCCGAGG TCCAGTTCAA<br>CTGGTACGTG GATGGCGTGG AGGTGCATAA TGCCAAGACA AAGCCGCGGG<br>AGGAGCAGTT CAACAGCACG TACCGTGTGG TCAGCGTCCT CACCGTCCTG<br>CACCAGGACT GGCTGAACGG CAAGGAGTAC AAGTGCAAGG TCTCCAACAA<br>AGGCCTCCCG TCCTCCATCG AGAAAACCAT CTCCAAAGCC AAAGGTCAGC<br>CCCGAGAGCC ACAGGTGTAC ACCCTGCCCC CATCCCAGGA GGAGATGACC<br>AAGAACCAGG TCAGCCTGAC CTGCCTGGTC AAAGGCTTCT ACCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTACAGC**AAC**<br>CTA**ACC**GTGG ACAAGAGCAG GTGGCAGGAG GGGAATGTCT TCTCATGCTC<br>CGTGATGCAT GAGGCTCTGC ACAACCACTA CACACAGAAG AGCCTCTCCC<br>TGTCTCTGGG TAAATGA |
| 53 | CH23 variants:<br>Protein<br>IgG1-CH23-<br>N364/N368 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQV**N**LTC**N**V **T**GFYPSDIAV EWESNGQPEN NYKTTPPVLD SDGSFFLYSK<br>LTVDKSRWQQ GNVFSCSVMH EALHNHYTQK SLSLSPGK |

-continued

SEQ LIST Table
In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 54 | CH23 variants:<br>DNA<br>IgG1-CH23-<br>N364/N368 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TC**AAC**CTGAC CTGC**AAC**GTC **ACC**GGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT CTATAGCAAG<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 55 | CH23 variants:<br>Protein<br>IgG1-CH23-<br>N364/N405 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQV**N**LTCLV KGFYPSDIAV EWESNGQPEN NYKTTPPVLD SDGSF**N**L**T**SK<br>LTVDKSRWQQ GNVFSCSVMH EALHNHYTQK SLSLSPGK |
| 56 | CH23 variants:<br>DNA<br>IgG1-CH23-<br>N364/N405 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TC**AAC**CTGAC CTGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTC**AAC**CT C**ACC**AGCAAG<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 57 | CH23 variants:<br>Protein<br>IgG1-CH23-<br>N364/N407 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQV**N**LTCLV KGFYPSDIAV EWESNGQPEN NYKTTPPVLD SDGSFFL**N**S**T**<br>LTVDKSRWQQ GNVFSCSVMH EALHNHYTQK SLSLSPGK |
| 58 | CH23 variants:<br>DNA<br>IgG1-CH23-<br>N364/N407 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TC**AAC**CTGAC CTGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT C**AAC**AGC**ACC**<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 59 | CH23 variants:<br>Protein<br>IgG1-CH23-<br>N258/N364/N407 | MKAVVLAVAL VFLTGSQARH HHHHHGGGPS VFLFPPKPKD TLMISRTP**N**V<br>TCVVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQV**NLT**CLV KGFYPSDIAV EWESNGQPEN NYKTTPPVLD SDGSFFL**N**S**T**<br>LTVDKSRWQQ GNVFSCSVMH EALHNHYTQK SLSLSPGK |

-continued

SEQ LIST Table
In SEQ ID Nos: 1-8, bold residues denote the positions rationally selected for N-glycosylation according to the present invention.
In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 60 | CH23 variants:<br>DNA<br>IgG1-CH23-<br>N258/N364/N407 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCT**AAC**GTC<br>ACATGCGTGG TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TC**AAC**CTGAC CTGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT C**AAC**AGC**ACC**<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 61 | CH23 variants:<br>IgG1-CH23-<br>N260/N364/N407 | MKAVVLAVAL VFLTGSQARH HHHHHGGGPS VFLFPPKPKD TLMISRTPEV<br>NCTVVDVSHE DPEVKFNWYV DGVEVHNAKT KPREEQYNST YRVVSVLTVL<br>HQDWLNGKEY KCKVSNKALP APIEKTISKA KGQPREPQVY TLPPSREEMT<br>KNQV**NLT**CLV KGFYPSDIAV EWESNGQPEN NYKTTPPVLD SDGSFFL**NST**<br>LTVDKSRWQQ GNVFSCSVMH EALHNHYTQK SLSLSPGK |
| 62 | CH23 variants:<br>DNA<br>IgG1-CH23-<br>N260/N364/N407 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>**AAC**TGC**ACC**G TGGTGGACGT GAGCCACGAA GACCCTGAGG TCAAGTTCAA<br>CTGGTACGTG GACGGCGTGG AGGTGCATAA TGCCAAGACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TC**AAC**CTGAC CTGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT C**AAC**AGC**ACC**<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 63 | CH23 variants:<br>Protein<br>IgG1-CH23-<br>N286/N364/N407 | MKAVVLAVAL VFLTGSQARH HHHHHGGGPS VFLFPPKPKD TLMISRTPEV<br>TCVVVDVSHE DPEVKFNWYV DGVEVHNA**T**T KPREEQYNST YRVVSVLTVL<br>HQDWLNGKEY KCKVSNKALP APIEKTISKA KGQPREPQVY TLPPSREEMT<br>KNQV**NLT**CLV KGFYPSDIAV EWESNGQPEN NYKTTPPVLD SDGSFFL**NST**<br>LTVDKSRWQQ GNVFSCSVMH EALHNHYTQK SLSLSPGK |
| 64 | CH23 variants:<br>DNA<br>IgG1-CH23-<br>N286/N364/N407 | ATGAAAGCTG TGGTGCTGGC CGTGGCTCTG GTCTTCCTGA CAGGGAGCCA<br>GGCTCGGCAT CATCATCACC ATCACGGCGG GGGACCGTCA GTCTTCCTCT<br>TCCCCCCAAA ACCCAAGGAC ACCCTCATGA TCTCCCGGAC CCCTGAGGTC<br>ACATGCGTGG TGGTGGACGT GAGCCACGAA GACCCTGAGG TCAAGTTCAA<br>CTGGTACGTG GACGGCGTGG AGGTGCATAA TGCC**ACC**ACA AAGCCGCGGG<br>AGGAGCAGTA CAACAGCACG TACCGTGTGG TCAGCGTCCT CACCGTCCTG<br>CACCAGGACT GGCTGAATGG CAAGGAGTAC AAGTGCAAGG TCTCCAACAA<br>AGCCCTCCCA GCCCCCATCG AGAAAACCAT CTCCAAAGCC AAAGGGCAGC<br>CCCGAGAACC ACAGGTGTAC ACCCTGCCCC CATCCCGGGA GGAGATGACC<br>AAGAACCAGG TC**AAC**CTGAC CTGCCTGGTC AAAGGCTTCT ATCCCAGCGA<br>CATCGCCGTG GAGTGGGAGA GCAATGGGCA GCCGGAGAAC AACTACAAGA<br>CCACGCCTCC CGTGCTGGAC TCCGACGGCT CCTTCTTCCT C**AAC**AGC**ACC**<br>CTCACCGTGG ACAAGAGCAG GTGGCAGCAG GGGAACGTCT TCTCATGCTC<br>CGTGATGCAT GAGGCTCTGC ACAACCACTA CACGCAGAAG AGCCTCTCCC<br>TGTCCCCGGG TAAATGA |
| 65 | CH23 variants:<br>Protein<br>IgG1-CH23-<br>N305/N364/N407 | MKAVVLAVAL VFLTGSQARH HHHHHGGGPS VFLFPPKPKD TLMISRTPEV<br>TCVVVDVSHE DPEVKFNWYV DGVEVHNAKT KPREEQYNST YRVVS**N**LTVL<br>HQDWLNGKEY KCKVSNKALP APIEKTISKA KGQPREPQVY TLPPSREEMT<br>KNQV**NLT**CLV KGFYPSDIAV EWESNGQPEN NYKTTPPVLD SDGSFFL**NST**<br>LTVDKSRWQQ GNVFSCSVMH EALHNHYTQK SLSLSPGK |

-continued

SEQ LIST Table
In SEQ ID Nos: 1-8, bold residues denote the positions rationally selected for N-glycosylation according to the present invention.
In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 66 | CH23 variants: DNA IgG1-CH23- N305/N364/N407 | ATGAAAGCTG TGGTGCTGGC CGTGGCTCTG GTCTTCCTGA CAGGGAGCCA GGCTCGGCAT CATCATCACC ATCACGGCGG GGGACCGTCA GTCTTCCTCT TCCCCCCAAA ACCCAAGGAC ACCCTCATGA TCTCCCGGAC CCCTGAGGTC ACATGCGTGG TGGTGGACGT GAGCCACGAA GACCCTGAGG TCAAGTTCAA CTGGTACGTG GACGGCGTGG AGGTGCATAA TGCCAAGACA AAGCCGCGGG AGGAGCAGTA CAACAGCACG TACCGTGTGG TCAGC**AAC**CT CACCGTCCTG CACCAGGACT GGCTGAATGG CAAGGAGTAC AAGTGCAAGG TCTCCAACAA AGCCCTCCCA GCCCCCATCG AGAAAACCAT CTCCAAAGCC AAAGGGCAGC CCCGAGAACC ACAGGTGTAC ACCCTGCCCC CATCCCGGGA GGAGATGACC AAGAACCAGG TC**AAC**CTGAC CTGCCTGGTC AAAGGCTTCT ATCCCAGCGA CATCGCCGTG GAGTGGGAGA GCAATGGGCA GCCGGAGAAC AACTACAAGA CCACGCCTCC CGTGCTGGAC TCCGACGGCT CCTTCTTCCT C**AAC**AGC**ACC** CTCACCGTGG ACAAGAGCAG GTGGCAGCAG GGGAACGTCT TCTCATGCTC CGTGATGCAT GAGGCTCTGC ACAACCACTA CACGCAGAAG AGCCTCTCCC TGTCCCCGGG TAAATGA |
| 67 | Fab-CH23 variants: Protein KLH-gamma1 | MGWSCIILFL VATATGAHSE VQLVESGGGL VQPGGSLRLS CAASGFTFSN YDMYWVRQTT GKGLEWVSAI GTAGDTYYPG SVKGRFTISR ENAKNSLYLQ MNSLRAGDTA VYYCAREKSS TSAFDYWGQG TLVTVSSAST KGPSVFPLAP CSRSTSESTA ALGCLVKDYF PEPVTVSWNS GALTSGVHTF PAVLQSSGLY SLSSVVTVPS SNFGTQTYTC NVDHKPSNTK VDKTVERKCC VECPPCPAPP VAGPSVFLFP PKPKDTLMIS RTPEVTCVVV DVSHEDPEVQ FNWYVDGVEV HNAKTKPREE QFNSTFRVVS VLTVVHQDWL NGKEYKCKVS NKGLPAPIEK TISKTKGQPR EPQVYTLPPS REEMTKNQVS LTCLVKGFYP SDIAVEWESN GQPENNYKTT PPMLDSDGSF FLYSKLTVDK SRWQQGNVFS CSVMHEALHN HYTQKSLSLS PGK |
| 68 | Fab-CH23 variants: DNA KLH-gamma1 | ATGGGATGGA GCTGTATCAT CCTCTTCTTG GTAGCAACAG CTACAGGCGC GCACTCCGAG GTGCAGCTGG TGGAGTCTGG GGGAGGCTTG GTACAGCCTG GGGGGTCCCT GAGACTCTCC TGTGCAGCCT CTGGATTCAC CTTCAGTAAC TACGACATGT ACTGGGTCCG CCAAACTACA GGAAAAGGTC TGGAGTGGGT CTCAGCTATT GGTACTGCTG GTGACACATA CTATCCAGGC TCCGTGAAGG GCCGATTCAC CATCTCCAGA GAAAATGCCA AGAACTCCTT GTATCTTCAA ATGAACAGCC TGAGAGCCGG GGACACGGCT GTGTATTACT GTGCAAGAGA GAAGTCTAGC ACCTCGGCCT TTGACTACTG GGGCCAGGGA ACCCTGGTCA CAGTCTCCTC AGCGTCGACC AAGGGCCCAT CGGTCTTCCC CCTGGCACCC TCCTCCAAGA GCACCTCTGG GGGCACAGCG GCCCTGGGCT GCCTGGTCAA GGACTACTTC CCCGAACCGG TGACGGTGTC GTGGAACTCA GGCGCCCTGA CCAGCGGCGT GCACACCTTC CCGGCTGTCC TACAGTCCTC AGGACTCTAC TCCCTCAGCA GCGTGGTGAC CGTGCCCTCC AGCAGCTTGG GCACCCAGAC CTACATCTGC AACGTGAATC ACAAGCCCAG CAACACCAAG GTGGACAAGA AAGTTGAGCC CAAATCTTGT GACAAAACTC ACACATGCCC ACCGTGCCCA GCACCTGAAC TCCTGGGGGG ACCGTCAGTC TTCCTCTTCC CCCCAAAACC CAAGGACACC CTCATGATCT CCCGGACCCC TGAGGTCACA TGCGTGGTGG TGGACGTGAG CCACGAAGAC CCTGAGGTCA AGTTCAACTG GTACGTGGAC GGCGTGGAGG TGCATAATGC CAAGACAAAG CCGCGGGAGG AGCAGTACAA CAGCACGTAC CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC GAGAACCACA GGTGTACACC CTGCCCCCAT CCCGGGAGGA GATGACCAAG AACCAGGTCA GCCTGACCTG CCTGGTCAAA GGCTTCTATC CCAGCGACAT CGCCGTGGAG TGGGAGAGCA ATGGGCAGCC GGAGAACAAC TACAAGACCA CGCCTCCCGT GCTGGACTCC GACGGCTCCT TCTTCCTCTA TAGCAAGCTC ACCGTGGACA AGAGCAGGTG GCAGCAGGGG AACGTCTTCT CATGCTCCGT GATGCATGAG GCTCTGCACA ACCACTACAC GCAGAAGAGC CTCTCCCTGT CCCCGGGTAA ATGA |
| 69 | Fab-CH23 variants: Protein KLH-kappa | MGWSCIILFL VATATGAHSD_IQMTQSPSSL SVSVGDRVTI TCQAGQDIRN YLNWYQQKPG KAPKLLIYDA SNLETGVPSR FSGSGSGTAF TFTISSLQPE DIATYYCQQY DNLTFGQGTK LEIKRTVAAP SVFIFPPSDE QLKSGTASVV CLLNNFYPRE AKVQWKVDNA LQSGNSQESV TEQDSKDSTY SLSSTLTLSK ADYEKHKVYA CEVTHQGLSS PVTKSFNRGE C |

-continued

SEQ LIST Table
In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 70 | Fab-CH23 variants: DNA KLH-kappa | ATGGGATGGA GCTGTATCAT CCTCTTCTTG GTAGCAACAG CTACAGGCGC<br>GCACTCCGAC ATCCAGATGA CCCAGTCTCC ATCCTCCCTG TCTGTATCTG<br>TGGGAGACAG AGTCACCATC ACTTGCCAGG CGGGTCAGGA CATTCGCAAC<br>TATTTAAATT GGTATCAGCA GAAACCAGGG AAAGCCCCTA AACTCCTGAT<br>CTACGATGCA TCCAATTTGG AAACAGGGGT CCCATCAAGG TTCAGTGGAA<br>GTGGATCTGG GACAGCTTTT ACTTTCACCA TCAGCAGCCT GCAGCCTGAA<br>GATATTGCAA CATATTACTG TCAACAGTAT GATAATCTCA CTTTTGGCCA<br>GGGGACCAAA CTGGAAATCA AACGTGAGTA GAATAACTCT AGAGGAATAG<br>GGAAGCTAGG AAGAAACTCA AAACATCAAG ATTTTAAATA CGCTTCTTGG<br>TCTCCTTGCT ATAATTATCT GGGATAAGCA TGCTGTTTTC TGTCTGTCCC<br>TAACATGCCC TGTGATTATC CGCAAACAAC ACACCCAAGG GCAGAACTTT<br>GTTACTTAAA CACCATCCTG TTTGCTTCTT TCCTCAGGAA CTGTGGCTGC<br>ACCATCTGTC TTCATCTTCC CGCCATCTGA TGAGCAGTTG AAATCTGGAA<br>CTGCCTCTGT TGTGTGCCTG CTGAATAACT TCTATCCCAG AGAGGCCAAA<br>GTACAGTGGA AGGTGGATAA CGCCCTCCAA TCGGGTAACT CCCAGGAGAG<br>TGTCACAGAG CAGGACAGCA AGGACAGCAC CTACAGCCTC AGCAGCACCC<br>TGACGCTGAG CAAAGCAGAC TACGAGAAAC ACAAAGTCTA CGCCTGCGAA<br>GTCACCCATC AGGGCCTGAG CTCGCCCGTC ACAAAGAGCT TCAACAGGGG<br>AGAGTGTTAG |
| 71 | Fab-CH23 variants: Protein Fab-CH23 | <u>MGWSCIILFL VATATGAHS</u>E VQLVESGGGL VQPGGSLRLS CAASGFTFSN<br>YDMYWVRQTT GKGLEWVSAI GTAGDTYYPG SVKGRFTISR ENAKNSLYLQ<br>MNSLRAGDTA VYYCAREKSS TSAFDYWGQG TLVTVSSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKKVEPKSC DKTHTGGGGS<br>GGGGSGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVNLTCLVK GFYPSDIAVE<br>WESNGQPENN YKTTPPVLDS DGSFFLNSTL TVDKSRWQQG NVFSCSVMHE<br>ALHNHYTQKS LSLSPGK |
| 72 | Fab-CH23 variants: DNA Fab-CH23 | ATGGGATGGA GCTGTATCAT CCTCTTCTTG GTAGCAACAG CTACAGGCGC<br>GCACTCCGAG GTGCAGCTGG TGGAGTCTGG GGGAGGCTTG GTACAGCCTG<br>GGGGGTCCCT GAGACTCTCC TGTGCAGCCT CTGGATTCAC CTTCAGTAAC<br>TACGACATGT ACTGGGTCCG CCAAACTACA GGAAAAGGTC TGGAGTGGGT<br>CTCAGCTATT GGTACTGCTG GTGACACATA CTATCCAGGC TCCGTGAAGG<br>GCCGATTCAC CATCTCCAGA GAAAATGCCA AGAACTCCTT GTATCTTCAA<br>ATGAACAGCC TGAGAGCCGG GGACACGGCT GTGTATTACT GTGCAAGAGA<br>GAAGTCTAGC ACCTCGGCCT TTGACTACTG GGGCCAGGGA ACCCTGGTCA<br>CCGTCTCCTC AGCCTCCACC AAGGGCCCGA GCGTGTTTCC GCTGGCACCG<br>AGCAGCAAAA GCACCAGCGG TGGCACAGCA GCACTGGGTT GTCTGGTGAA<br>AGATTATTTT CCGGAACCGG TTACAGTTAG CTGGAATAGC GGTGCCCTGA<br>CCAGCGGTGT TCATACCTTT CCGGCAGTTC TGCAGAGCAG CGGTCTGTAT<br>AGCCTGTCTA GCGTTGTTAC CGTTCCGAGC AGCAGCCTGG GCACCCAGAC<br>CTATATTTGC AATGTGAATC ATAAACCGAG CAATACCAAA GTGGATAAAA<br>AAGTGGAGCC TAAGAGCTGT GACAAAACTC ACACAGGTGG AGGCGGGTCC<br>GGTGGAGGCG GGTCCGGGGG ACCGTCAGTC TTCCTCTTCC CCCCAAAACC<br>CAAGGACACC CTCATGATCT CCCGGACCCC TGAGGTCACA TGCGTGGTGG<br>TGGACGTGAG CCACGAAGAC CCTGAGGTCA AGTTCAACTG GTACGTGGAC<br>GGCGTGGAGG TGCATAATGC CAAGACAAAG CCGCGGGAGG AGCAGTACAA<br>CAGCACGTAC CGTGTGGTCA GCGTCCTCAC CGTCCTGCAC CAGGACTGGC<br>TGAATGGCAA GGAGTACAAG TGCAAGGTCT CCAACAAAGC CCTCCCAGCC<br>CCCATCGAGA AAACCATCTC CAAAGCCAAA GGGCAGCCCC GAGAACCACA<br>GGTGTACACC CTGCCCCCAT CCCGGGAGGA GATGACCAAG AACCAGGTCA<br>ACCTGACCTG CCTGGTCAAA GGCTTCTATC CCAGCGACAT CGCCGTGGAG<br>TGGGAGAGCA ATGGGCAGCC GGAGAACAAC TACAAGACCA CGCCTCCCGT<br>GCTGGACTCC GACGGCTCCT TCTTCCTCAA CAGCACCCTC ACCGTGGACA<br>AGAGCAGGTG GCAGCAGGGG AACGTCTTCT CATGCTCCGT GATGCATGAG<br>GCTCTGCACA ACCACTACAC GCAGAAGAGC CTCTCCCTGT CCCCGGGTAA<br>ATGA |

-continued

| SEQ LIST Table<br>In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker. | | |
|---|---|---|
| SEQ ID NO: | DETAILS | |
| 73 | Fab-CH23 variants: Protein Fab-CH23[M428L/N434S] | MGWSCIILFL VATATGAHSE VQLVESGGGL VQPGGSLRLS CAASGFTFSN YDMYWVRQTT GKGLEWVSAI GTAGDTYYPG SVKGRFTISR ENAKNSLYLQ MNSLRAGDTA VYYCAREKSS TSAFDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTGGGGS GGGGSGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVNLTCLVK GFYPSDIAVE WESNGQPENN YKTTPPVLDS DGSFFLNSTL TVDKSRWQQG NVFSCSVLHE ALHSHYTQKS LSLSPGK |
| 74 | Fab-CH23 variants: DNA Fab-CH23[M428L/N434S] | ATGGGATGGA GCTGTATCAT CCTCTTCTTG GTAGCAACAG CTACAGGCGC GCACTCCGAG GTGCAGCTGG TGGAGTCTGG GGGAGGCTTG GTACAGCCTG GGGGGTCCCT GAGACTCTCC TGTGCAGCCT CTGGATTCAC CTTCAGTAAC TACGACATGT ACTGGGTCCG CCAAACTACA GGAAAAGGTC TGGAGTGGGT CTCAGCTATT GGTACTGCTG GTGACACATA CTATCCAGGC TCCGTGAAGG GCCGATTCAC CATCTCCAGA GAAAATGCCA AGAACTCCTT GTATCTTCAA ATGAACAGCC TGAGAGCCGG GGACACGGCT GTGTATTACT GTGCAAGAGA GAAGTCTAGC ACCTCGGCCT TTGACTACTG GGGCCAGGGA ACCCTGGTCA CCGTCTCCTC AGCCTCCACC AAGGGCCCGA GCGTGTTTCC GCTGGCACCG AGCAGCAAAA GCACCAGCGG TGGCACAGCA GCACTGGGTT GTCTGGTGAA AGATTATTTT CCGGAACCGG TTACAGTTAG CTGGAATAGC GGTGCCCTGA CCAGCGGTGT TCATACCTTT CCGGCAGTTC TGCAGAGCAG CGGTCTGTAT AGCCTGTCTA GCGTTGTTAC CGTTCCGAGC AGCAGCCTGG GCACCCAGAC CTATATTTGC AATGTGAATC ATAAACCGAG CAATACCAAA GTGGATAAAA AAGTGGAGCC TAAGAGCTGT GACAAAACTC ACACAGGTGG AGGCGGGTCC GGTGGAGGCG GGTCCGGGGG ACCGTCAGTC TTCCTCTTCC CCCCAAAACC CAAGGACACC CTCATGATCT CCCGGACCCC TGAGGTCACA TGCGTGGTGG TGGACGTGAG CCACGAAGAC CCTGAGGTCA AGTTCAACTG GTACGTGGAC GGCGTGGAGG TGCATAATGC CAAGACAAAG CCGCGGGAGG AGCAGTACAA CAGCACGTAC CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC GAGAACCACA GGTGTACACC CTGCCCCCAT CCCGGGAGGA GATGACCAAG AACCAGGTCA ACCTGACCTG CCTGGTCAAA GGCTTCTATC CCAGCGACAT CGCCGTGGAG TGGGAGAGCA ATGGGCAGCC GGAGAACAAC TACAAGACCA CGCCTCCCGT GCTGGACTCC GACGGCTCCT TCTTCCTCAA CAGCACCCTC ACCGTGGACA AGAGCAGGTG GCAGCAGGGG AACGTCTTCT CATGCTCCGT GCTGCATGAG GCTCTGCACA GCCACTACAC GCAGAAGAGC CTCTCCCTGT CCCCGGGTAA ATGA |
| 75 | Fab-CH23 variants: Protein Fab-CH23[H310A/H433A] | MGWSCIILFL VATATGAHSE VQLVESGGGL VQPGGSLRLS CAASGFTFSN YDMYWVRQTT GKGLEWVSAI GTAGDTYYPG SVKGRFTISR ENAKNSLYLQ MNSLRAGDTA VYYCAREKSS TSAFDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTGGGGS GGGGSGGPSV FLFPPKPKDT LMISRTPEVT CVVVDVSHED PEVKFNWYVD GVEVHNAKTK PREEQYNSTY RVVSVLTVLA QDWLNGKEYK CKVSNKALPA PIEKTISKAK GQPREPQVYT LPPSREEMTK NQVNLTCLVK GFYPSDIAVE WESNGQPENN YKTTPPVLDS DGSFFLNSTL TVDKSRWQQG NVFSCSVMHE ALANHYTQKS LSLSPGK |
| 76 | Fab-CH23 variants: DNA Fab-CH23[H310A/H433A] | ATGGGATGGA GCTGTATCAT CCTCTTCTTG GTAGCAACAG CTACAGGCGC GCACTCCGAG GTGCAGCTGG TGGAGTCTGG GGGAGGCTTG GTACAGCCTG GGGGGTCCCT GAGACTCTCC TGTGCAGCCT CTGGATTCAC CTTCAGTAAC TACGACATGT ACTGGGTCCG CCAAACTACA GGAAAAGGTC TGGAGTGGGT CTCAGCTATT GGTACTGCTG GTGACACATA CTATCCAGGC TCCGTGAAGG GCCGATTCAC CATCTCCAGA GAAAATGCCA AGAACTCCTT GTATCTTCAA ATGAACAGCC TGAGAGCCGG GGACACGGCT GTGTATTACT GTGCAAGAGA GAAGTCTAGC ACCTCGGCCT TTGACTACTG GGGCCAGGGA ACCCTGGTCA CCGTCTCCTC AGCCTCCACC AAGGGCCCGA GCGTGTTTCC GCTGGCACCG AGCAGCAAAA GCACCAGCGG TGGCACAGCA GCACTGGGTT GTCTGGTGAA AGATTATTTT CCGGAACCGG TTACAGTTAG CTGGAATAGC GGTGCCCTGA CCAGCGGTGT TCATACCTTT CCGGCAGTTC TGCAGAGCAG CGGTCTGTAT AGCCTGTCTA GCGTTGTTAC CGTTCCGAGC AGCAGCCTGG GCACCCAGAC CTATATTTGC AATGTGAATC ATAAACCGAG CAATACCAAA GTGGATAAAA AAGTGGAGCC TAAGAGCTGT GACAAAACTC ACACAGGTGG AGGCGGGTCC |

-continued

| SEQ LIST Table<br>In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker. | | |
|---|---|---|
| SEQ ID NO: | DETAILS | |
| | | GGTGGAGGCG GGTCCGGGGG ACCGTCAGTC TTCCTCTTCC CCCCAAAACC<br>CAAGGACACC CTCATGATCT CCCGGACCCC TGAGGTCACA TGCGTGGTGG<br>TGGACGTGAG CCACGAAGAC CCTGAGGTCA AGTTCAACTG GTACGTGGAC<br>GGCGTGGAGG TGCATAATGC CAAGACAAAG CCGCGGGAGG AGCAGTACAA<br>CAGCACGTAC CGTGTGGTCA GCGTCCTCAC CGTCCTGGCC CAGGACTGGC<br>TGAATGGCAA GGAGTACAAG TGCAAGGTCT CCAACAAAGC CCTCCCAGCC<br>CCCATCGAGA AAACCATCTC CAAAGCCAAA GGGCAGCCCC GAGAACCACA<br>GGTGTACACC CTGCCCCCAT CCCGGGAGGA GATGACCAAG AACCAGGTCA<br>ACCTGACCTG CCTGGTCAAA GGCTTCTATC CCAGCGACAT CGCCGTGGAG<br>TGGGAGAGCA ATGGGCAGCC GGAGAACAAC TACAAGACCA CGCCTCCCGT<br>GCTGGACTCC GACGGCTCCT TCTTCCTCAA CAGCACCCTC ACCGTGGACA<br>AGAGCAGGTG GCAGCAGGGG AACGTCTTCT CATGCTCCGT GATGCATGAG<br>GCTCTGGCCA ACCACTACAC GCAGAAGAGC CTCTCCCTGT CCCCGGGTAA<br>ATGA |
| 77 | Fab-CH23 variants: Protein Fab-CH23-0XGS-CH23 | MGWSCIILFL VATATGAHSE VQLVESGGGL VQPGGSLRLS CAASGFTFSN<br>YDMYWVRQTT GKGLEWVSAI GTAGDTYYPG SVKGRFTISR ENAKNSLYLQ<br>MNSLRAGDTA VYYCAREKSS TSAFDYWGQG TLVTVSSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKKVEPKSC DKTHTGGGGS<br>GGGGSGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVNLTCLVK GFYPSDIAVE<br>WESNGQPENN YKTTPPVLDS DGSFFLNSTL TVDKSRWQQG NVFSCSVMHE<br>ALHNHYTQKS LSLSPGGPSV FLFPPKPKDT LMISRTPEVT CVVVDVSHED<br>PEVKFNWYVD GVEVHNAKTK PREEQYNSTY RVVSVLTVLH QDWLNGKEYK<br>CKVSNKALPA PIEKTISKAK GQPREPQVYT LPPSREEMTK NQVNLTCLVK<br>GFYPSDIAVE WESNGQPENN YKTTPPVLDS DGSFFLNSTL TVDKSRWQQG<br>NVFSCSVMHE ALHNHYTQKS LSLSPGK |
| 78 | Fab-CH23 variants: DNA Fab-CH23-0XGS-CH23 | ATGGGATGGA GCTGTATCAT CCTCTTCTTG GTAGCAACAG CTACAGGCGC<br>GCACTCCGAG GTGCAGCTGG TGGAGTCTGG GGGAGGCTTG GTACAGCCTG<br>GGGGGTCCCT GAGACTCTCC TGTGCAGCCT CTGGATTCAC CTTCAGTAAC<br>TACGACATGT ACTGGGTCCG CCAAACTACA GGAAAAGGTC TGGAGTGGGT<br>CTCAGCTATT GGTACTGCTG GTGACACATA CTATCCAGGC TCCGTGAAGG<br>GCCGATTCAC CATCTCCAGA GAAAATGCCA AGAACTCCTT GTATCTTCAA<br>ATGAACAGCC TGAGAGCCGG GGACACGGCT GTGTATTACT GTGCAAGAGA<br>GAAGTCTAGC ACCTCGGCCT TTGACTACTG GGGCCAGGGA ACCCTGGTCA<br>CCGTCTCCTC AGCCTCCACC AAGGGCCCGA GCGTGTTTCC GCTGGCACCG<br>AGCAGCAAAA GCACCAGCGG TGGCACAGCA GCACTGGGTT GTCTGGTGAA<br>AGATTATTTT CCGGAACCGG TTACAGTTAG CTGGAATAGC GGTGCCCTGA<br>CCAGCGGTGT TCATACCTTT CCGGCAGTTC TGCAGAGCAG CGGTCTGTAT<br>AGCCTGTCTA GCGTTGTTAC CGTTCCGAGC AGCAGCCTGG GCACCCAGAC<br>CTATATTTGC AATGTGAATC ATAAACCGAG CAATACCAAA GTGGATAAAA<br>AAGTGGAGCC TAAGAGCTGT GACAAAACTC ACACAGGTGG AGGCGGGTCC<br>GGTGGAGGCG GGTCCGGGGG ACCGTCAGTC TTCCTCTTCC CCCCAAAACC<br>CAAGGACACC CTCATGATCT CCCGGACCCC TGAGGTCACA TGCGTGGTGG<br>TGGACGTGAG CCACGAAGAC CCTGAGGTCA AGTTCAACTG GTACGTGGAC<br>GGCGTGGAGG TGCATAATGC CAAGACAAAG CCGCGGGAGG AGCAGTACAA<br>CAGCACGTAC CGTGTGGTCA GCGTCCTCAC CGTCCTGCAC CAGGACTGGC<br>TGAATGGCAA GGAGTACAAG TGCAAGGTCT CCAACAAAGC CCTCCCAGCC<br>CCCATCGAGA AAACCATCTC CAAAGCCAAA GGGCAGCCCC GAGAACCACA<br>GGTGTACACC CTGCCCCCAT CCCGGGAGGA GATGACCAAG AACCAGGTCA<br>ACCTGACCTG CCTGGTCAAA GGCTTCTATC CCAGCGACAT CGCCGTGGAG<br>TGGGAGAGCA ATGGGCAGCC GGAGAACAAC TACAAGACCA CGCCTCCCGT<br>GCTGGACTCC GACGGCTCCT TCTTCCTCAA CAGCACCCTC ACCGTGGACA<br>AGAGCAGGTG GCAGCAGGGG AACGTCTTCT CATGCTCCGT GATGCATGAG<br>GCTCTGCACA ACCACTACAC GCAGAAGAGC CTCTCCCTGT CCCCGGGTGG<br>GGGACCGTCA GTCTTCCTCT TCCCCCCAAA ACCCAAGGAC ACCCTCATGA<br>TCTCCCGGAC CCCTGAGGTC ACATGCGTGG TGGTGGACGT GAGCCACGAA<br>GACCCTGAGG TCAAGTTCAA CTGGTACGTG GACGGCGTGG AGGTGCATAA<br>TGCCAAGACA AAGCCGCGGG AGGAGCAGTA CAACAGCACG TACCGTGTGG<br>TCAGCGTCCT CACCGTCCTG CACCAGGACT GGCTGAATGG CAAGGAGTAC<br>AAGTGCAAGG TCTCCAACAA AGCCCTCCCA GCCCCCATCG AGAAAACCAT<br>CTCCAAAGCC AAAGGGCAGC CCCGAGAACC ACAGGTGTAC ACCCTGCCCC<br>CATCCCGGGA GGAGATGACC AAGAACCAGG TCAACCTGAC CTGCCTGGTC<br>AAAGGCTTCT ATCCCAGCGA CATCGCCGTG GAGTGGGAGA GCAATGGGCA |

-continued

SEQ LIST Table
In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| | | GCCGGAGAAC AACTACAAGA CCACGCCTCC CGTGCTGGAC TCCGACGGCT<br>CCTTCTTCCT CAACAGCACC CTCACCGTGG ACAAGAGCAG GTGGCAGCAG<br>GGGAACGTCT TCTCATGCTC CGTGATGCAT GAGGCTCTGC ACAACCACTA<br>CACGCAGAAG AGCCTCTCCC TGTCCCCGGG TAAATGA |
| 79 | Fab-CH23 variants: Protein Fab-CH23-1XGS-CH23 | MGWSCIILFL VATATGAHSE VQLVESGGGL VQPGGSLRLS CAASGFTFSN<br>YDMYWVRQTT GKGLEWVSAI GTAGDTYYPG SVKGRFTISR ENAKNSLYLQ<br>MNSLRAGDTA VYYCAREKSS TSAFDYWGQG TLVTVSSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKKVEPKSC DKTHTGGGGS<br>GGGGSGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVNLTCLVK GFYPSDIAVE<br>WESNGQPENN YKTTPPVLDS DGSFFLNSTL TVDKSRWQQG NVFSCSVMHE<br>ALHNHYTQKS LSLSPGGGGS GGPSVFLFPP KPKDTLMISR TPEVTCVVVD<br>VSHEDPEVKF NWYVDGVEVH NAKTKPREEQ YNSTYRVVSV LTVLHQDWLN<br>GKEYKCKVSN KALPAPIEKT ISKAKGQPRE PQVYTLPPSR EEMTKNQVNL<br>TCLVKGFYPS DIAVEWESNG QPENNYKTTP PVLDSDGSFF LNSTLTVDKS<br>RWQQGNVFSC SVMHEALHNH YTQKSLSLSP GK |
| 80 | Fab-CH23 variants: DNA Fab-CH23-1XGS-CH23 | ATGGGATGGA GCTGTATCAT CCTCTTCTTG GTAGCAACAG CTACAGGCGC<br>GCACTCCGAG GTGCAGCTGG TGGAGTCTGG GGGAGGCTTG GTACAGCCTG<br>GGGGGTCCCT GAGACTCTCC TGTGCAGCCT CTGGATTCAC CTTCAGTAAC<br>TACGACATGT ACTGGGTCCG CCAAACTACA GGAAAAGGTC TGGAGTGGGT<br>CTCAGCTATT GGTACTGCTG GTGACACATA CTATCCAGGC TCCGTGAAGG<br>GCCGATTCAC CATCTCCAGA GAAAATGCCA AGAACTCCTT GTATCTTCAA<br>ATGAACAGCC TGAGAGCCGG GGACACGGCT GTGTATTACT GTGCAAGAGA<br>GAAGTCTAGC ACCTCGGCCT TTGACTACTG GGGCCAGGGA ACCCTGGTCA<br>CCGTCTCCTC AGCCTCCACC AAGGGCCCGA GCGTGTTTCC GCTGGCACCG<br>AGCAGCAAAA GCACCAGCGG TGGCACAGCA GCACTGGGTT GTCTGGTGAA<br>AGATTATTTT CCGGAACCGG TTACAGTTAG CTGGAATAGC GGTGCCCTGA<br>CCAGCGGTGT TCATACCTTT CCGGCAGTTC TGCAGAGCAG CGGTCTGTAT<br>AGCCTGTCTA GCGTTGTTAC CGTTCCGAGC AGCAGCCTGG GCACCCAGAC<br>CTATATTTGC AATGTGAATC ATAAACCGAG CAATACCAAA GTGGATAAAA<br>AAGTGGAGCC TAAGAGCTGT GACAAAACTC ACACAGGTGG AGGCGGGTCC<br>GGTGGAGGCG GGTCCGGGGG ACCGTCAGTC TTCCTCTTCC CCCCAAAACC<br>CAAGGACACC CTCATGATCT CCCGGACCCC TGAGGTCACA TGCGTGGTGG<br>TGGACGTGAG CCACGAAGAC CCTGAGGTCA AGTTCAACTG GTACGTGGAC<br>GGCGTGGAGG TGCATAATGC CAAGACAAAG CCGCGGGAGG AGCAGTACAA<br>CAGCACGTAC CGTGTGGTCA GCGTCCTCAC CGTCCTGCAC CAGGACTGGC<br>TGAATGGCAA GGAGTACAAG TGCAAGGTCT CCAACAAAGC CCTCCCAGCC<br>CCCATCGAGA AAACCATCTC CAAAGCCAAA GGGCAGCCCC GAGAACCACA<br>GGTGTACACC CTGCCCCCAT CCCGGGAGGA GATGACCAAG AACCAGGTCA<br>ACCTGACCTG CCTGGTCAAA GGCTTCTATC CCAGCGACAT CGCCGTGGAG<br>TGGGAGAGCA ATGGGCAGCC GGAGAACAAC TACAAGACCA CGCCTCCCGT<br>GCTGGACTCC GACGGCTCCT TCTTCCTCAA CAGCACCCTC ACCGTGGACA<br>AGAGCAGGTG GCAGCAGGGG AACGTCTTCT CATGCTCCGT GATGCATGAG<br>GCTCTGCACA ACCACTACAC GCAGAAGAGC CTCTCCCTGT CCCCGGGTGG<br>TGGCGGCTCC GGGGGACCGT CAGTCTTCCT CTTCCCCCCA AAACCCAAGG<br>ACACCCTCAT GATCTCCCGG ACCCCTGAGG TCACATGCGT GGTGGTGGAC<br>GTGAGCCACG AAGACCCTGA GGTCAAGTTC AACTGGTACG TGGACGGCGT<br>GGAGGTGCAT AATGCCAAGA CAAAGCCGCG GGAGGAGCAG TACAACAGCA<br>CGTACCGTGT GGTCAGCGTC CTCACCGTCC TGCACCAGGA CTGGCTGAAT<br>GGCAAGGAGT ACAAGTGCAA GGTCTCCAAC AAAGCCCTCC CAGCCCCCAT<br>CGAGAAAACC ATCTCCAAAG CCAAAGGGCA GCCCCGAGAA CCACAGGTGT<br>ACACCCTGCC CCCATCCCGG GAGGAGATGA CCAAGAACCA GGTCAACCTG<br>ACCTGCCTGG TCAAAGGCTT CTATCCCAGC GACATCGCCG TGGAGTGGGA<br>GAGCAATGGG CAGCCGGAGA ACAACTACAA GACCACGCCT CCCGTGCTGG<br>ACTCCGACGG CTCCTTCTTC CTCAACAGCA CCCTCACCGT GGACAAGAGC<br>AGGTGGCAGC AGGGGAACGT CTTCTCATGC TCCGTGATGC ATGAGGCTCT<br>GCACAACCAC TACACGCAGA AGAGCCTCTC CCTGTCCCCG GGTAAATGA |
| 81 | Fab-CH23 variants: Protein Fab-CH23-2XGS-CH23 | MGWSCIILFL VATATGAHSE VQLVESGGGL VQPGGSLRLS CAASGFTFSN<br>YDMYWVRQTT GKGLEWVSAI GTAGDTYYPG SVKGRFTISR ENAKNSLYLQ<br>MNSLRAGDTA VYYCAREKSS TSAFDYWGQG TLVTVSSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKKVEPKSC DKTHTGGGGS |

-continued

SEQ LIST Table
In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| | | GGGGSGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVNLTCLVK GFYPSDIAVE WESNGQPENN YKTTPPVLDS DGSFFLNSTL TVDKSRWQQG NVFSCSVMHE ALHNHYTQKS LSLSPGGGGS GGGGSGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVNLTCLVK GFYPSDIAVE WESNGQPENN YKTTPPVLDS DGSFFLNSTL TVDKSRWQQG NVFSCSVMHE ALHNHYTQKS LSLSPGK |
| 82 | Fab-CH23 variants: DNA Fab-CH23-2XGS-CH23 | ATGGGATGGA GCTGTATCAT CCTCTTCTTG GTAGCAACAG CTACAGGCGC GCACTCCGAG GTGCAGCTGG TGGAGTCTGG GGGAGGCTTG GTACAGCCTG GGGGGTCCCT GAGACTCTCC TGTGCAGCCT CTGGATTCAC CTTCAGTAAC TACGACATGT ACTGGGTCCG CCAAACTACA GGAAAAGGTC TGGAGTGGGT CTCAGCTATT GGTACTGCTG GTGACACATA CTATCCAGGC TCCGTGAAGG GCCGATTCAC CATCTCCAGA GAAAATGCCA AGAACTCCTT GTATCTTCAA ATGAACAGCC TGAGAGCCGG GGACACGGCT GTGTATTACT GTGCAAGAGA GAAGTCTAGC ACCTCGGCCT TTGACTACTG GGGCCAGGGA ACCCTGGTCA CCGTCTCCTC AGCCTCCACC AAGGGCCCGA GCGTGTTTCC GCTGGCACCG AGCAGCAAAA GCACCAGCGG TGGCACAGCA GCACTGGGTT GTCTGGTGAA AGATTATTTT CCGGAACCGG TTACAGTTAG CTGGAATAGC GGTGCCCTGA CCAGCGGTGT TCATACCTTT CCGGCAGTTC TGCAGAGCAG CGGTCTGTAT AGCCTGTCTA GCGTTGTTAC CGTTCCGAGC AGCAGCCTGG GCACCCAGAC CTATATTTGC AATGTGAATC ATAAACCGAG CAATACCAAA GTGGATAAAA AAGTGGAGCC TAAGAGCTGT GACAAAACTC ACACAGGTGG AGGCGGGTCC GGTGGAGGCG GGTCCGGGGG ACCGTCAGTC TTCCTCTTCC CCCCAAAACC CAAGGACACC CTCATGATCT CCCGGACCCC TGAGGTCACA TGCGTGGTGG TGGACGTGAG CCACGAAGAC CCTGAGGTCA AGTTCAACTG GTACGTGGAC GGCGTGGAGG TGCATAATGC CAAGACAAAG CCGCGGGAGG AGCAGTACAA CAGCACGTAC CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC GAGAACCACA GGTGTACACC CTGCCCCCAT CCCGGGAGGA GATGACCAAG AACCAGGTCA ACCTGACCTG CCTGGTCAAA GGCTTCTATC CCAGCGACAT CGCCGTGGAG TGGGAGAGCA ATGGGCAGCC GGAGAACAAC TACAAGACCA CGCCTCCCGT GCTGGACTCC GACGGCTCCT TCTTCCTCAA CAGCACCCTC ACCGTGGACA AGAGCAGGTG GCAGCAGGGG AACGTCTTCT CATGCTCCGT GATGCATGAG GCTCTGCACA ACCACTACAC GCAGAAGAGC CTCTCCCTGT CCCCGGGTGG TGGCGGCTCC GGCGGTGGAG GGTCTGGGGG ACCGTCAGTC TTCCTCTTCC CCCCAAAACC CAAGGACACC CTCATGATCT CCCGGACCCC TGAGGTCACA TGCGTGGTGG TGGACGTGAG CCACGAAGAC CCTGAGGTCA AGTTCAACTG GTACGTGGAC GGCGTGGAGG TGCATAATGC CAAGACAAAG CCGCGGGAGG AGCAGTACAA CAGCACGTAC CGTGTGGTCA GCGTCCTCAC CGTCCTGCAC CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC GAGAACCACA GGTGTACACC CTGCCCCCAT CCCGGGAGGA GATGACCAAG AACCAGGTCA ACCTGACCTG CCTGGTCAAA GGCTTCTATC CCAGCGACAT CGCCGTGGAG TGGGAGAGCA ATGGGCAGCC GGAGAACAAC TACAAGACCA CGCCTCCCGT GCTGGACTCC GACGGCTCCT TCTTCCTCAA CAGCACCCTC ACCGTGGACA AGAGCAGGTG GCAGCAGGGG AACGTCTTCT CATGCTCCGT GATGCATGAG GCTCTGCACA ACCACTACAC GCAGAAGAGC CTCTCCCTGT CCCCGGGTAA ATGA |
| 83 | Fab-CH23 variants: Protein Fab-CH23-3XGS-CH23 | MGWSCIILFL VATATGAHSE VQLVESGGGL VQPGGSLRLS CAASGFTFSN YDMYWVRQTT GKGLEWVSAI GTAGDTYYPG SVKGRFTISR ENAKNSLYLQ MNSLRAGDTA VYYCAREKSS TSAFDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTGGGGS GGGGSGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVNLTCLVK GFYPSDIAVE WESNGQPENN YKTTPPVLDS DGSFFLNSTL TVDKSRWQQG NVFSCSVMHE ALHNHYTQKS LSLSPGGGGS GGGGSGGGGS GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR EEMTKNQVNL TCLVKGFYPS DIAVEWESNG QPENNYKTTP PVLDSDGSFF LNSTLTVDKS RWQQGNVFSC SVMHEALHNH YTQKSLSLSP GK |

-continued

SEQ LIST Table

In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 84 | Fab-CH23 variants: DNA Fab-CH23-3XGS-CH23 | ATGGGATGGA GCTGTATCAT CCTCTTCTTG GTAGCAACAG CTACAGGCGC<br>GCACTCCGAG GTGCAGCTGG TGGAGTCTGG GGGAGGCTTG GTACAGCCTG<br>GGGGGTCCCT GAGACTCTCC TGTGCAGCCT CTGGATTCAC CTTCAGTAAC<br>TACGACATGT ACTGGGTCCG CCAAACTACA GGAAAAGGTC TGGAGTGGGT<br>CTCAGCTATT GGTACTGCTG GTGACACATA CTATCCAGGC TCCGTGAAGG<br>GCCGATTCAC CATCTCCAGA GAAAATGCCA AGAACTCCTT GTATCTTCAA<br>ATGAACAGCC TGAGAGCCGG GGACACGGCT GTGTATTACT GTGCAAGAGA<br>GAAGTCTAGC ACCTCGGCCT TTGACTACTG GGGCCAGGGA ACCCTGGTCA<br>CCGTCTCCTC AGCCTCCACC AAGGGCCCGA GCGTGTTTCC GCTGGCACCG<br>AGCAGCAAAA GCACCAGCGG TGGCACAGCA GCACTGGGTT GTCTGGTGAA<br>AGATTATTTT CCGGAACCGG TTACAGTTAG CTGGAATAGC GGTGCCCTGA<br>CCAGCGGTGT TCATACCTTT CCGGCAGTTC TGCAGAGCAG CGGTCTGTAT<br>AGCCTGTCTA GCGTTGTTAC CGTTCCGAGC AGCAGCCTGG GCACCCAGAC<br>CTATATTTGC AATGTGAATC ATAAACCGAG CAATACCAAA GTGGATAAAA<br>AAGTGGAGCC TAAGAGCTGT GACAAAACTC ACACAGGTGG AGGCGGGTCC<br>GGTGGAGGCG GGTCCGGGGG ACCGTCAGTC TTCCTCTTCC CCCCAAAACC<br>CAAGGACACC CTCATGATCT CCCGGACCCC TGAGGTCACA TGCGTGGTGG<br>TGGACGTGAG CCACGAAGAC CCTGAGGTCA AGTTCAACTG GTACGTGGAC<br>GGCGTGGAGG TGCATAATGC CAAGACAAAG CCGCGGGAGG AGCAGTACAA<br>CAGCACGTAC CGTGTGGTCA GCGTCCTCAC CGTCCTGCAC CAGGACTGGC<br>TGAATGGCAA GGAGTACAAG TGCAAGGTCT CCAACAAAGC CCTCCCAGCC<br>CCCATCGAGA AAACCATCTC CAAAGCCAAA GGGCAGCCCC GAGAACCACA<br>GGTGTACACC CTGCCCCCAT CCCGGGAGGA GATGACCAAG AACCAGGTCA<br>ACCTGACCTG CCTGGTCAAA GGCTTCTATC CCAGCGACAT CGCCGTGGAG<br>TGGGAGAGCA ATGGGCAGCC GGAGAACAAC TACAAGACCA CGCCTCCCGT<br>GCTGGACTCC GACGGCTCCT TCTTCCTCAA CAGCACCCTC ACCGTGGACA<br>AGAGCAGGTG GCAGCAGGGG AACGTCTTCT CATGCTCCGT GATGCATGAG<br>GCTCTGCACA ACCACTACAC GCAGAAGAGC CTCTCCCTGT CCCCGGGTGG<br>TGGCGGCTCC GGAGGTGGCG GAAGCGGCGG TGGAGGGTCT GGGGGACCGT<br>CAGTCTTCCT CTTCCCCCCA AAACCCAAGG ACACCCTCAT GATCTCCCGG<br>ACCCCTGAGG TCACATGCGT GGTGGTGGAC GTGAGCCACG AAGACCCTGA<br>GGTCAAGTTC AACTGGTACG TGGACGGCGT GGAGGTGCAT AATGCCAAGA<br>CAAAGCCGCG GGAGGAGCAG TACAACAGCA CGTACCGTGT GGTCAGCGTC<br>CTCACCGTCC TGCACCAGGA CTGGCTGAAT GGCAAGGAGT ACAAGTGCAA<br>GGTCTCCAAC AAAGCCCTCC CAGCCCCCAT CGAGAAAACC ATCTCCAAAG<br>CCAAAGGGCA GCCCCGAGAA CCACAGGTGT ACACCCTGCC CCCATCCCGG<br>GAGGAGATGA CCAAGAACCA GGTCAACCTG ACCTGCCTGG TCAAAGGCTT<br>CTATCCCAGC GACATCGCCG TGGAGTGGGA GAGCAATGGG CAGCCGGAGA<br>ACAACTACAA GACCACGCCT CCCGTGCTGG ACTCCGACGG CTCCTTCTTC<br>CTCAACAGCA CCCTCACCGT GGACAAGAGC AGGTGGCAGC AGGGGAACGT<br>CTTCTCATGC TCCGTGATGC ATGAGGCTCT GCACAACCAC TACACGCAGA<br>AGAGCCTCTC CCTGTCCCCG GGTAAATGA |
| 85 | Fab-CH23 variants: Protein Fab-CH23-4XGS-CH23 | MGWSCIILFL VATATGAHSE VQLVESGGGL VQPGGSLRLS CAASGFTFSN<br>YDMYWVRQTT GKGLEWVSAI GTAGDTYYPG SVKGRFTISR ENAKNSLYLQ<br>MNSLRAGDTA VYYCAREKSS TSAFDYWGQG TLVTVSSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKKVEPKSC DKTHTGGGGS<br>GGGGSGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVNLTCLVK GFYPSDIAVE<br>WESNGQPENN YKTTPPVLDS DGSFFLNSTL TVDKSRWQQG NVFSCSVMHE<br>ALHNHYTQKS LSLSPGGGGS GGGGSGGGGS GGGGSGGPSV FLFPPKPKDT<br>LMISRTPEVT CVVVDVSHED PEVKFNWYVD GVEVHNAKTK PREEQYNSTY<br>RVVSVLTVLH QDWLNGKEYK CKVSNKALPA PIEKTISKAK GQPREPQVYT<br>LPPSREEMTK NQVNLTCLVK GFYPSDIAVE WESNGQPENN YKTTPPVLDS<br>DGSFFLNSTL TVDKSRWQQG NVFSCSVMHE ALHNHYTQKS LSLSPGK |

-continued

SEQ LIST Table
In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
|---|---|---|
| 86 | Fab-CH23 variants: DNA Fab-CH23-4XGS-CH23 | ATGGGATGGA GCTGTATCAT CCTCTTCTTG GTAGCAACAG CTACAGGCGC<br>GCACTCCGAG GTGCAGCTGG TGGAGTCTGG GGGAGGCTTG GTACAGCCTG<br>GGGGGTCCCT GAGACTCTCC TGTGCAGCCT CTGGATTCAC CTTCAGTAAC<br>TACGACATGT ACTGGGTCCG CCAAACTACA GGAAAAGGTC TGGAGTGGGT<br>CTCAGCTATT GGTACTGCTG GTGACACATA CTATCCAGGC TCCGTGAAGG<br>GCCGATTCAC CATCTCCAGA GAAAATGCCA AGAACTCCTT GTATCTTCAA<br>ATGAACAGCC TGAGAGCCGG GGACACGGCT GTGTATTACT GTGCAAGAGA<br>GAAGTCTAGC ACCTCGGCCT TTGACTACTG GGGCCAGGGA ACCCTGGTCA<br>CCGTCTCCTC AGCCTCCACC AAGGGCCCGA GCGTGTTTCC GCTGGCACCG<br>AGCAGCAAAA GCACCAGCGG TGGCACAGCA GCACTGGGTT GTCTGGTGAA<br>AGATTATTTT CCGGAACCGG TTACAGTTAG CTGGAATAGC GGTGCCCTGA<br>CCAGCGGTGT TCATACCTTT CCGGCAGTTC TGCAGAGCAG CGGTCTGTAT<br>AGCCTGTCTA GCGTTGTTAC CGTTCCGAGC AGCAGCCTGG GCACCCAGAC<br>CTATATTTGC AATGTGAATC ATAAACCGAG CAATACCAAA GTGGATAAAA<br>AAGTGGAGCC TAAGAGCTGT GACAAAACTC ACACAGGTGG AGGCGGGTCC<br>GGTGGAGGCG GGTCCGGGGG ACCGTCAGTC TTCCTCTTCC CCCCAAAACC<br>CAAGGACACC CTCATGATCT CCCGGACCCC TGAGGTCACA TGCGTGGTGG<br>TGGACGTGAG CCACGAAGAC CCTGAGGTCA AGTTCAACTG GTACGTGGAC<br>GGCGTGGAGG TGCATAATGC CAAGACAAAG CCGCGGGAGG AGCAGTACAA<br>CAGCACGTAC CGTGTGGTCA GCGTCCTCAC CGTCCTGCAC CAGGACTGGC<br>TGAATGGCAA GGAGTACAAG TGCAAGGTCT CCAACAAAGC CCTCCCAGCC<br>CCCATCGAGA AAACCATCTC CAAAGCCAAA GGGCAGCCCC GAGAACCACA<br>GGTGTACACC CTGCCCCCAT CCCGGGAGGA GATGACCAAG AACCAGGTCA<br>ACCTGACCTG CCTGGTCAAA GGCTTCTATC CCAGCGACAT CGCCGTGGAG<br>TGGGAGAGCA ATGGGCAGCC GGAGAACAAC TACAAGACCA CGCCTCCCGT<br>GCTGGACTCC GACGGCTCCT TCTTCCTCAA CAGCACCCTC ACCGTGGACA<br>AGAGCAGGTG GCAGCAGGGG AACGTCTTCT CATGCTCCGT GATGCATGAG<br>GCTCTGCACA ACCACTACAC GCAGAAGAGC CTCTCCCTGT CCCCGGGTGG<br>TGGCGGCTCC GGAGGTGGCG GAAGCGGCGG TGGAGGGTCT GGTGGAGGAG<br>GGTCAGGGGG ACCGTCAGTC TTCCTCTTCC CCCCAAAACC CAAGGACACC<br>CTCATGATCT CCCGGACCCC TGAGGTCACA TGCGTGGTGG TGGACGTGAG<br>CCACGAAGAC CCTGAGGTCA AGTTCAACTG GTACGTGGAC GGCGTGGAGG<br>TGCATAATGC CAAGACAAAG CCGCGGGAGG AGCAGTACAA CAGCACGTAC<br>CGTGTGGTCA GCGTCCTCAC CGTCCTGCAC CAGGACTGGC TGAATGGCAA<br>GGAGTACAAG TGCAAGGTCT CCAACAAAGC CCTCCCAGCC CCCATCGAGA<br>AAACCATCTC CAAAGCCAAA GGGCAGCCCC GAGAACCACA GGTGTACACC<br>CTGCCCCCAT CCCGGGAGGA GATGACCAAG AACCAGGTCA ACCTGACCTG<br>CCTGGTCAAA GGCTTCTATC CCAGCGACAT CGCCGTGGAG TGGGAGAGCA<br>ATGGGCAGCC GGAGAACAAC TACAAGACCA CGCCTCCCGT GCTGGACTCC<br>GACGGCTCCT TCTTCCTCAA CAGCACCCTC ACCGTGGACA AGAGCAGGTG<br>GCAGCAGGGG AACGTCTTCT CATGCTCCGT GATGCATGAG GCTCTGCACA<br>ACCACTACAC GCAGAAGAGC CTCTCCCTGT CCCCGGGTAA ATGA |
| 87 | Fab-CH23 variants: Protein Fab-CH23-5XGS-CH23 | MGWSCIILFL VATATGAHSE VQLVESGGGL VQPGGSLRLS CAASGFTFSN<br>YDMYWVRQTT GKGLEWVSAI GTAGDTYYPG SVKGRFTISR ENAKNSLYLQ<br>MNSLRAGDTA VYYCAREKSS TSAFDYWGQG TLVTVSSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKKVEPKSC DKTHTGGGGS<br>GGGGSGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVNLTCLVK GFYPSDIAVE<br>WESNGQPENN YKTTPPVLDS DGSFFLNSTL TVDKSRWQQG NVFSCSVMHE<br>ALHNHYTQKS LSLSPGGGGS GGGGSGGGGS GGGGSGGGGS GGPSVFLFPP<br>KPKDTLMISR TPEVTCVVVD VSHEDPEVKF NWYVDGVEVH NAKTKPREEQ<br>YNSTYRVVSV LTVLHQDWLN GKEYKCKVSN KALPAPIEKT ISKAKGQPRE<br>PQVYTLPPSR EEMTKNQVNL TCLVKGFYPS DIAVEWESNG QPENNYKTTP<br>PVLDSDGSFF LNSTLTVDKS RWQQGNVFSC SVMHEALHNH YTQKSLSLSP<br>GK |
| 88 | Fab-CH23 variants: DNA Fab-CH23-5XGS-CH23 | ATGGGATGGA GCTGTATCAT CCTCTTCTTG GTAGCAACAG CTACAGGCGC<br>GCACTCCGAG GTGCAGCTGG TGGAGTCTGG GGGAGGCTTG GTACAGCCTG<br>GGGGGTCCCT GAGACTCTCC TGTGCAGCCT CTGGATTCAC CTTCAGTAAC<br>TACGACATGT ACTGGGTCCG CCAAACTACA GGAAAAGGTC TGGAGTGGGT<br>CTCAGCTATT GGTACTGCTG GTGACACATA CTATCCAGGC TCCGTGAAGG<br>GCCGATTCAC CATCTCCAGA GAAAATGCCA AGAACTCCTT GTATCTTCAA<br>ATGAACAGCC TGAGAGCCGG GGACACGGCT GTGTATTACT GTGCAAGAGA<br>GAAGTCTAGC ACCTCGGCCT TTGACTACTG GGGCCAGGGA ACCCTGGTCA |

-continued

SEQ LIST Table

In SEQ ID Nos: 1-8, bold residues denote the positions rationally selected for N-glycosylation according to the present invention. In SEQ ID Nos 17-88, the bold residues denote amino acid/nucleic acid variations, the first underlined region is the signal/leader sequence, and where present, the second underlined region denotes the linker.

| SEQ ID NO: | DETAILS | |
| --- | --- | --- |
| | | CCGTCTCCTC AGCCTCCACC AAGGGCCCGA GCGTGTTTCC GCTGGCACCG<br>AGCAGCAAAA GCACCAGCGG TGGCACAGCA GCACTGGGTT GTCTGGTGAA<br>AGATTATTTT CCGGAACCGG TTACAGTTAG CTGGAATAGC GGTGCCCTGA<br>CCAGCGGTGT TCATACCTTT CCGGCAGTTC TGCAGAGCAG CGGTCTGTAT<br>AGCCTGTCTA GCGTTGTTAC CGTTCCGAGC AGCAGCCTGG GCACCCAGAC<br>CTATATTTGC AATGTGAATC ATAAACCGAG CAATACCAAA GTGGATAAAA<br>AAGTGGAGCC TAAGAGCTGT GACAAAACTC ACACAGGTGG AGGCGGGTCC<br>GGTGGAGGCG GGTCCGGGGG ACCGTCAGTC TTCCTCTTCC CCCCAAAACC<br>CAAGGACACC CTCATGATCT CCCGGACCCC TGAGGTCACA TGCGTGGTGG<br>TGGACGTGAG CCACGAAGAC CCTGAGGTCA AGTTCAACTG GTACGTGGAC<br>GGCGTGGAGG TGCATAATGC CAAGACAAAG CCGCGGGAGG AGCAGTACAA<br>CAGCACGTAC CGTGTGGTCA GCGTCCTCAC CGTCCTGCAC CAGGACTGGC<br>TGAATGGCAA GGAGTACAAG TGCAAGGTCT CCAACAAAGC CCTCCCAGCC<br>CCCATCGAGA AAACCATCTC CAAAGCCAAA GGGCAGCCCC GAGAACCACA<br>GGTGTACACC CTGCCCCCAT CCCGGGAGGA GATGACCAAG AACCAGGTCA<br>ACCTGACCTG CCTGGTCAAA GGCTTCTATC CCAGCGACAT CGCCGTGGAG<br>TGGGAGAGCA ATGGGCAGCC GGAGAACAAC TACAAGACCA CGCCTCCCGT<br>GCTGGACTCC GACGGCTCCT TCTTCCTCAA CAGCACCCTC ACCGTGGACA<br>AGAGCAGGTG GCAGCAGGGG AACGTCTTCT CATGCTCCGT GATGCATGAG<br>GCTCTGCACA ACCACTACAC GCAGAAGAGC CTCTCCCTGT CCCCGGGTGG<br>TGGCGGCTCC GGAGGCGGAG GCTCCGGAGG TGGCGGAAGC GGCGGTGGAG<br>GGTCTGGTGG AGGAGGGTCA GGGGGACCGT CAGTCTTCCT CTTCCCCCCA<br>AAACCCAAGG ACACCCTCAT GATCTCCCGG ACCCCTGAGG TCACATGCGT<br>GGTGGTGGAC GTGAGCCACG AAGACCCTGA GGTCAAGTTC AACTGGTACG<br>TGGACGGCGT GGAGGTGCAT AATGCCAAGA CAAAGCCGCG GGAGGAGCAG<br>TACAACAGCA CGTACCGTGT GGTCAGCGTC CTCACCGTCC TGCACCAGGA<br>CTGGCTGAAT GGCAAGGAGT ACAAGTGCAA GGTCTCCAAC AAAGCCCTCC<br>CAGCCCCCAT CGAGAAAACC ATCTCCAAAG CCAAAGGGCA GCCCCGAGAA<br>CCACAGGTGT ACACCCTGCC CCCATCCCGG GAGGAGATGA CCAAGAACCA<br>GGTCAACCTG ACCTGCCTGG TCAAAGGCTT CTATCCCAGC GACATCGCCG<br>TGGAGTGGGA GAGCAATGGG CAGCCGGAGA ACAACTACAA GACCACGCCT<br>CCCGTGCTGG ACTCCGACGG CTCCTTCTTC CTCAACAGCA CCCTCACCGT<br>GGACAAGAGC AGGTGGCAGC AGGGGAACGT CTTCTCATGC TCCGTGATGC<br>ATGAGGCTCT GCACAACCAC TACACGCAGA AGAGCCTCTC CCTGTCCCCG<br>GGTAAATGA |
| 89 | $G_4S$ Linker Peptide | GGGGS |
| 90 | $(G_4S)_2$ Linker Peptide | GGGGSGGGGS |
| 91 | $(G_4S)_3$ Linker Peptide | GGGGSGGGGS GGGGS |
| 92 | $(G_4S)_4$ Linker Peptide | GGGGSGGGGS GGGGSGGGGS |
| 93 | $(G_4S)_5$ Linker Peptide | GGGGSGGGGS GGGGSGGGGS GGGGS |

Although the disclosed teachings have been described with reference to various applications, methods, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A polypeptide comprising an IgG CH2 and an IgG CH3 domain, (i) wherein the CH3 domain comprises one or more engineered N-linked glycosylation sites in a CH3-CH3 dimerization interface, (ii) wherein the engineered N-linked glycosylation sites are selected from the group consisting of Q347N-X-Y349T, Q347N-X-Y349S, Y349N-X-L351T, Y349N-X-L351S, L351N-X-P353T, L351N-X-P353S, S354N-X-D356T, S354N-X-D356S, D356N-X-L358T, D356N-X-L358S, E357N-X-T359S, K360N-X-Q362T, K360N-X-Q362S, S364N-X-T366S, L368N-X-K370T, L368N-X-K370S, K370N-X-F372T, K370N-X-F372S, K392N-X-T394S, V397N-X-D399T, V397N-X-D399S, S400N-X-G402T, S400N-

X-G402S, D401N-X-S403T, F405N-X-Y407T, F405N-X-Y407S, Y407N-X-K409T, Y407N-X-K409S, K409N-X-T411S, K439N-X-L441T, K439N-X-L441S, S444N-X-G446T, and S444N-X-G446S, wherein X is any amino acid except Pro, and (iii) wherein said polypeptide forms a soluble monomer.

2. A fusion protein comprising at least two recombinantly linked polypeptides of claim 1, wherein each polypeptide has the same or different engineered N-linked glycosylation sites in the CH3-CH3 dimerization interface.

3. The polypeptide of claim 1, wherein the amino acid modifications in the CH3-CH3 dimerization interface are selected from the group consisting of S364N-X-T366S, L368N-X-K370T, L368N-X-K370S, F405N-X-Y407T, F405N-X-Y407S, Y407N-X-K409T, and Y407N-X-K409S.

4. A polypeptide comprising an IgG CH2 and an IgG CH3 domain, (i) wherein the CH3 domain comprises two engineered N-linked glycosylation sites in a CH3-CH3 dimerization interface, (ii) wherein the engineered N-linked glycosylation sites are selected from the group consisting of a) S364N and Y407N-X-K409T; b) S364N-X-T366S and Y407N-X-K409T; c) S364N and Y407N-X-K409S; and d) S364N-X-T366S and Y407N-X-K409S, wherein X is any amino acid except Pro; and (iii) wherein said polypeptide forms a soluble monomer.

5. A fusion protein comprising at least two recombinantly linked polypeptides of claim 4, wherein each polypeptide has the same or different engineered N-linked glycosylation sites in the CH3-CH3 dimerization interface.

6. The polypeptide of claim 1, wherein the CH2 domain comprises one or more engineered N-linked glycosylation sites in a CH2-CH2 dimerization interface, and wherein the N-linked glycosylation sites are selected from the group consisting of S239N-X-F241S, S239N-X-F241T, F241N-X-243T, F241N-X-243S, E258N, E258N-X-T260S, T260N-X-V262T, T260N-X-V262S, V262N-X-V264S, V262N-X-V264T, K288T, K288S, K288N-K290T, K288N-K290S, V305N, and V305-X-T307S.

7. A fusion protein comprising at least two recombinantly linked polypeptides, wherein each polypeptide comprises at least one engineered N-linked glycosylation site, wherein the engineered N-linked glycosylation site comprises at least one amino acid modification selected from the group consisting of E258N-X-T260S, T260N-X-V262T, T260N-X-V262S, V305N, V305N-X-T307S, Q347N-X-Y349T, Q347N-X-Y349S, S364N-X-T366S, T366N-X-L368T, T366N-X-L368S, L368N-X-K370T, L368N-X-K370S, D401N, D401N-X-S403T, F405N-X-Y407T, F405N-X-Y407S, Y407N-X-K409T, Y407N-X-K409S, and K409N-X-T411S, wherein X is any amino acid except Pro, and wherein each polypeptide has the same or different engineered N-linked glycosylation site.

8. The polypeptide of claim 1, further comprising a Fab.

9. The fusion protein of claim 2, further comprising a Fab.

10. The fusion protein of claim 2, wherein each polypeptide is linked recombinantly via C-N terminus linkage or via a linker.

11. The polypeptide of claim 10, wherein the linker comprises the amino acid sequence (GGGGS)n (SEQ ID NO:89), wherein n=1-10.

12. The fusion protein of claim 2, wherein the polypeptide comprises two recombinantly linked polypeptides, wherein each polypeptide has the same engineered N-linked glycosylation sites in each CH3-CH3 dimerization interface, and further wherein the engineered N-linked glycosylation sites are S364N-X-T366 and Y407N-X-K409T.

13. An isolated polynucleotide comprising a nucleotide sequence encoding the polypeptide of claim 1.

14. A host cell comprising the polynucleotide of claim 13.

15. A method for producing a polypeptide comprising the step of culturing the host cell of claim 14 and, optionally, recovering the polypeptide.

16. The polypeptide of claim 1, wherein the amino acid modifications are F405N-X-Y407T.

17. The polypeptide of claim 1, wherein the amino acid modifications are L368N-X-K370T.

18. The polypeptide of claim 1, wherein a amino acid modifications are S364N-X-T366S.

19. The polypeptide of claim 1, wherein the amino acid modifications are Y407N-X-K409T.

20. The polypeptide of claim 4, wherein the amino acid modifications are S364N and Y407N-X-K409S.

21. The fusion protein of claim 5, wherein the polypeptide comprises two recombinantly linked polypeptides, wherein each polypeptide comprises amino acid modifications of S364N and Y407N-X-K409T.

* * * * *

SEQUENCE LISTING

<160> NUMBER OF SEQ ID NOS: 93

<210> SEQ ID NO 1
<211> LENGTH: 104
<212> TYPE: PRT
<213> ORGANISM: Homo Sapiens

<400> SEQUENCE: 1

```
Arg Glu Pro Gln Val Tyr Thr Leu Pro Pro Ser Arg Asp Glu Leu Thr
1               5                   10                  15

Lys Asn Gln Val Ser Leu Thr Cys Leu Val Lys Gly Phe Tyr Pro Ser
            20                  25                  30

Asp Ile Ala Val Glu Trp Glu Ser Asn Gly Gln Pro Glu Asn Asn Tyr
        35                  40                  45

Lys Thr Thr Pro Pro Val Leu Asp Ser Asp Gly Ser Phe Phe Leu Tyr
    50                  55                  60

Ser Lys Leu Thr Val Asp Lys Ser Arg Trp Gln Gln Gly Asn Val Phe
65                  70                  75                  80

Ser Cys Ser Val Met His Glu Ala Leu His Asn His Tyr Thr Gln Lys
                85                  90                  95

Ser Leu Ser Leu Ser Pro Gly Lys
            100
```

<210> SEQ ID NO 2
<211> LENGTH: 104
<212> TYPE: PRT
<213> ORGANISM: Homo Sapiens

<400> SEQUENCE: 2

```
Arg Glu Pro Gln Val Tyr Thr Leu Pro Pro Ser Arg Glu Glu Met Thr
1               5                   10                  15

Lys Asn Gln Val Ser Leu Thr Cys Leu Val Lys Gly Phe Tyr Pro Ser
            20                  25                  30

Asp Ile Ser Val Glu Trp Glu Ser Asn Gly Gln Pro Glu Asn Asn Tyr
        35                  40                  45

Lys Thr Thr Pro Pro Met Leu Asp Ser Asp Gly Ser Phe Phe Leu Tyr
    50                  55                  60

Ser Lys Leu Thr Val Asp Lys Ser Arg Trp Gln Gln Gly Asn Val Phe
65                  70                  75                  80

Ser Cys Ser Val Met His Glu Ala Leu His Asn His Tyr Thr Gln Lys
                85                  90                  95

Ser Leu Ser Leu Ser Pro Gly Lys
            100
```

<210> SEQ ID NO 3
<211> LENGTH: 104
<212> TYPE: PRT
<213> ORGANISM: Homo Sapiens

<400> SEQUENCE: 3

```
Arg Glu Pro Gln Val Tyr Thr Leu Pro Pro Ser Gln Glu Glu Met Thr
1               5                   10                  15

Lys Asn Gln Val Ser Leu Thr Cys Leu Val Lys Gly Phe Tyr Pro Ser
            20                  25                  30

Asp Ile Ala Val Glu Trp Glu Ser Asn Gly Gln Pro Glu Asn Asn Tyr
        35                  40                  45

Lys Thr Thr Pro Pro Val Leu Asp Ser Asp Gly Ser Phe Phe Leu Tyr
    50                  55                  60
```

```
Ser Arg Leu Thr Val Asp Lys Ser Arg Trp Gln Glu Gly Asn Val Phe
65                  70                  75                  80

Ser Cys Ser Val Met His Glu Ala Leu His Asn His Tyr Thr Gln Lys
                85                  90                  95

Ser Leu Ser Leu Ser Leu Gly Lys
            100


<210> SEQ ID NO 4
<211> LENGTH: 104
<212> TYPE: PRT
<213> ORGANISM: Mus musculus

<400> SEQUENCE: 4

Arg Glu Pro Gln Val Tyr Thr Leu Pro Pro Ser Gln Glu Glu Met Thr
1               5                   10                  15

Lys Asn Gln Val Ser Leu Thr Cys Leu Val Lys Gly Phe Tyr Pro Ser
            20                  25                  30

Asp Ile Ala Val Glu Trp Glu Ser Asn Gly Gln Pro Glu Asn Asn Tyr
        35                  40                  45

Lys Thr Thr Pro Pro Val Leu Asp Ser Asp Gly Ser Phe Phe Leu Tyr
    50                  55                  60

Ser Arg Leu Thr Val Asp Lys Ser Arg Trp Gln Glu Gly Asn Val Phe
65                  70                  75                  80

Ser Cys Ser Val Met His Glu Ala Leu His Asn His Tyr Thr Gln Lys
                85                  90                  95

Ser Leu Ser Leu Ser Leu Gly Lys
            100


<210> SEQ ID NO 5
<211> LENGTH: 104
<212> TYPE: PRT
<213> ORGANISM: Mus musculus

<400> SEQUENCE: 5

Lys Ala Pro Gln Val Tyr Thr Ile Pro Pro Pro Lys Glu Gln Met Ala
1               5                   10                  15

Lys Asp Lys Val Ser Leu Thr Cys Met Ile Thr Asp Phe Phe Pro Glu
            20                  25                  30

Asp Ile Thr Val Glu Trp Gln Trp Asn Gly Gln Pro Ala Glu Asn Tyr
        35                  40                  45

Lys Asn Thr Gln Pro Ile Met Asn Thr Asn Gly Ser Tyr Phe Val Tyr
    50                  55                  60

Ser Lys Leu Asn Val Gln Lys Ser Asn Trp Glu Ala Gly Asn Thr Phe
65                  70                  75                  80

Thr Cys Ser Val Leu His Glu Gly Leu His Asn His His Thr Glu Lys
                85                  90                  95

Ser Leu Ser His Ser Pro Gly Lys
            100


<210> SEQ ID NO 6
<211> LENGTH: 104
<212> TYPE: PRT
<213> ORGANISM: Mus musculus

<400> SEQUENCE: 6

Arg Ala Pro Gln Val Tyr Val Leu Pro Pro Pro Glu Glu Glu Met Thr
1               5                   10                  15
```

```
Lys Lys Gln Val Thr Leu Thr Cys Met Val Thr Asp Phe Met Pro Glu
            20                  25                  30

Asp Ile Tyr Val Glu Trp Thr Asn Asn Gly Lys Thr Glu Leu Asn Tyr
        35                  40                  45

Lys Asn Thr Glu Pro Val Leu Asp Ser Asp Gly Ser Tyr Phe Met Tyr
    50                  55                  60

Ser Lys Leu Arg Val Glu Lys Lys Asn Trp Val Glu Arg Asn Ser Tyr
65                  70                  75                  80

Ser Cys Ser Val Val His Glu Gly Leu His Asn His His Thr Thr Lys
                85                  90                  95

Ser Phe Ser Arg Thr Pro Gly Lys
            100
```

<210> SEQ ID NO 7
<211> LENGTH: 104
<212> TYPE: PRT
<213> ORGANISM: Mus musculus

<400> SEQUENCE: 7

```
Arg Ala Pro Gln Val Tyr Ile Leu Pro Pro Pro Ala Glu Gln Leu Ser
1               5                   10                  15

Arg Lys Asp Val Ser Leu Thr Cys Leu Val Val Gly Phe Asn Pro Gly
            20                  25                  30

Asp Ile Ser Val Glu Trp Thr Ser Asn Gly His Thr Glu Glu Asn Tyr
        35                  40                  45

Lys Asp Thr Ala Pro Val Leu Asp Ser Asp Gly Ser Tyr Phe Ile Tyr
    50                  55                  60

Ser Lys Leu Asn Met Lys Thr Ser Lys Trp Glu Lys Thr Asp Ser Phe
65                  70                  75                  80

Ser Cys Asn Val Arg His Glu Gly Leu Lys Asn Tyr Tyr Leu Lys Lys
                85                  90                  95

Thr Ile Ser Arg Ser Pro Gly Lys
            100
```

<210> SEQ ID NO 8
<211> LENGTH: 104
<212> TYPE: PRT
<213> ORGANISM: Mus musculus

<400> SEQUENCE: 8

```
Gln Thr Pro Gln Val Tyr Thr Ile Pro Pro Pro Arg Glu Gln Met Ser
1               5                   10                  15

Lys Lys Lys Val Ser Leu Thr Cys Leu Val Thr Asn Phe Phe Ser Glu
            20                  25                  30

Ala Ile Ser Val Glu Trp Glu Arg Asn Gly Glu Leu Glu Gln Asp Tyr
        35                  40                  45

Lys Asn Thr Pro Pro Ile Leu Asp Ser Asp Gly Thr Tyr Phe Leu Tyr
    50                  55                  60

Ser Lys Leu Thr Val Asp Thr Asp Ser Trp Leu Gln Gly Glu Ile Phe
65                  70                  75                  80

Thr Cys Ser Val Val His Glu Ala Leu His Asn His His Thr Gln Lys
                85                  90                  95

Asn Leu Ser Arg Ser Pro Gly Lys
            100
```

<210> SEQ ID NO 9
<211> LENGTH: 108

```
<212> TYPE: PRT
<213> ORGANISM: Homo Sapiens

<400> SEQUENCE: 9

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro
            100                 105


<210> SEQ ID NO 10
<211> LENGTH: 108
<212> TYPE: PRT
<213> ORGANISM: Homo Sapiens

<400> SEQUENCE: 10

Ala Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Gln Phe Asn Trp Tyr Val Asp Gly Val Glu
        35                  40                  45

Val His Asn Ala Lys Thr Lys Pro Arg Glu Glu Gln Phe Asn Ser Thr
    50                  55                  60

Phe Arg Val Val Ser Val Leu Thr Val Val His Gln Asp Trp Leu Asn
65                  70                  75                  80

Gly Lys Glu Tyr Lys Cys Lys Val Ser Asn Lys Gly Leu Pro Ala Pro
                85                  90                  95

Ile Glu Lys Thr Ile Ser Lys Thr Lys Gly Gln Pro
            100                 105


<210> SEQ ID NO 11
<211> LENGTH: 108
<212> TYPE: PRT
<213> ORGANISM: Homo Sapiens

<400> SEQUENCE: 11

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Gln Phe Lys Trp Tyr Val Asp Gly Val Glu
        35                  40                  45

Val His Asn Ala Lys Thr Lys Pro Arg Glu Glu Gln Tyr Asn Ser Thr
    50                  55                  60

Phe Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
```

```
                85                  90                  95

Ile Glu Lys Thr Ile Ser Lys Thr Lys Gly Gln Pro
            100                 105


<210> SEQ ID NO 12
<211> LENGTH: 108
<212> TYPE: PRT
<213> ORGANISM: Homo Sapiens

<400> SEQUENCE: 12

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

Gln Glu Asp Pro Glu Val Gln Phe Asn Trp Tyr Val Asp Gly Val Glu
        35                  40                  45

Val His Asn Ala Lys Thr Lys Pro Arg Glu Glu Gln Phe Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Gly Leu Pro Ser Ser
                85                  90                  95

Ile Glu Lys Thr Ile Ser Lys Ala Lys Gly Gln Pro
            100                 105


<210> SEQ ID NO 13
<211> LENGTH: 108
<212> TYPE: PRT
<213> ORGANISM: Mus musculus

<400> SEQUENCE: 13

Glu Val Ser Ser Val Phe Ile Phe Pro Pro Lys Pro Lys Asp Val Leu
1               5                   10                  15

Thr Ile Thr Leu Thr Pro Lys Val Thr Cys Val Val Val Asp Ile Ser
            20                  25                  30

Lys Asp Asp Pro Glu Val Gln Phe Ser Trp Phe Val Asp Asp Val Glu
        35                  40                  45

Val His Thr Ala Gln Thr Gln Pro Arg Glu Glu Gln Phe Asn Ser Thr
    50                  55                  60

Phe Arg Ser Val Ser Glu Leu Pro Ile Met His Gln Asp Trp Leu Asn
65                  70                  75                  80

Gly Lys Glu Phe Lys Cys Arg Val Asn Ser Ala Ala Phe Pro Ala Pro
                85                  90                  95

Ile Glu Lys Thr Ile Ser Lys Thr Lys Gly Arg Pro
            100                 105


<210> SEQ ID NO 14
<211> LENGTH: 108
<212> TYPE: PRT
<213> ORGANISM: Mus musculus

<400> SEQUENCE: 14

Gly Gly Pro Ser Val Phe Ile Phe Pro Pro Lys Ile Lys Asp Val Leu
1               5                   10                  15

Met Ile Ser Leu Ser Pro Ile Val Thr Cys Val Val Val Asp Val Ser
            20                  25                  30

Glu Asp Asp Pro Asp Val Gln Ile Ser Trp Phe Val Asn Asn Val Glu
        35                  40                  45
```

Val His Thr Ala Gln Thr Gln Thr His Arg Glu Asp Tyr Asn Ser Thr
    50                  55                  60

Leu Arg Val Val Ser Ala Leu Pro Ile Gln His Gln Asp Trp Met Ser
65                  70                  75                  80

Gly Lys Glu Phe Lys Cys Lys Val Asn Asn Lys Asp Leu Pro Ala Pro
                85                  90                  95

Ile Glu Arg Thr Ile Ser Lys Pro Lys Gly Ser Val
            100                 105

<210> SEQ ID NO 15
<211> LENGTH: 108
<212> TYPE: PRT
<213> ORGANISM: Mus musculus

<400> SEQUENCE: 15

Gly Gly Pro Ser Val Phe Ile Phe Pro Pro Asn Ile Lys Asp Val Leu
1               5                   10                  15

Met Ile Ser Leu Thr Pro Lys Val Thr Cys Val Val Val Asp Val Ser
            20                  25                  30

Glu Asp Asp Pro Asp Val Gln Ile Ser Trp Phe Val Asn Asn Val Glu
        35                  40                  45

Val His Thr Ala Gln Thr Gln Thr His Arg Glu Asp Tyr Asn Ser Thr
    50                  55                  60

Ile Arg Val Val Ser Thr Leu Pro Ile Gln His Gln Asp Trp Met Ser
65                  70                  75                  80

Gly Lys Glu Phe Lys Cys Lys Val Asn Asn Lys Asp Leu Pro Ser Pro
                85                  90                  95

Ile Glu Arg Thr Ile Ser Lys Ile Lys Gly Leu Val
            100                 105

<210> SEQ ID NO 16
<211> LENGTH: 108
<212> TYPE: PRT
<213> ORGANISM: Mus musculus

<400> SEQUENCE: 16

Gly Gly Pro Ser Val Phe Ile Phe Pro Pro Lys Pro Lys Asp Ala Leu
1               5                   10                  15

Met Ile Ser Leu Thr Pro Lys Val Thr Cys Val Val Val Asp Val Ser
            20                  25                  30

Glu Asp Asp Pro Asp Val His Val Ser Trp Phe Val Asp Asn Lys Glu
        35                  40                  45

Val His Thr Ala Trp Thr Gln Pro Arg Glu Ala Gln Tyr Asn Ser Thr
    50                  55                  60

Phe Arg Val Val Ser Ala Leu Pro Ile Gln His Gln Asp Trp Met Arg
65                  70                  75                  80

Gly Lys Glu Phe Lys Cys Lys Val Asn Asn Lys Ala Leu Pro Ala Pro
                85                  90                  95

Ile Glu Arg Thr Ile Ser Lys Pro Lys Gly Arg Ala
            100                 105

<210> SEQ ID NO 17
<211> LENGTH: 238
<212> TYPE: PRT
<213> ORGANISM: Artificial Sequence
<220> FEATURE:
<223> OTHER INFORMATION: Synthetic Construct

<400> SEQUENCE: 17

Met Lys Ala Val Val Leu Ala Val Ala Leu Val Phe Leu Thr Gly Ser
1 5 10 15

Gln Ala Arg His His His His His His Gly Gly Gly Pro Ser Val Phe
20 25 30

Leu Phe Pro Pro Lys Pro Lys Asp Thr Leu Met Ile Ser Arg Thr Pro
35 40 45

Glu Val Thr Cys Val Val Val Asp Val Ser His Glu Asp Pro Glu Val
50 55 60

Lys Phe Asn Trp Tyr Val Asp Gly Val Glu Val His Asn Ala Lys Thr
65 70 75 80

Lys Pro Arg Glu Glu Gln Tyr Asn Ser Thr Tyr Arg Val Val Ser Val
85 90 95

Leu Thr Val Leu His Gln Asp Trp Leu Asn Gly Lys Glu Tyr Lys Cys
100 105 110

Lys Val Ser Asn Lys Ala Leu Pro Ala Pro Ile Glu Lys Thr Ile Ser
115 120 125

Lys Ala Lys Gly Gln Pro Arg Glu Pro Asn Val Thr Thr Leu Pro Pro
130 135 140

Ser Arg Glu Glu Met Thr Lys Asn Gln Val Ser Leu Thr Cys Leu Val
145 150 155 160

Lys Gly Phe Tyr Pro Ser Asp Ile Ala Val Glu Trp Glu Ser Asn Gly
165 170 175

Gln Pro Glu Asn Asn Tyr Lys Thr Thr Pro Pro Val Leu Asp Ser Asp
180 185 190

Gly Ser Phe Phe Leu Tyr Ser Lys Leu Thr Val Asp Lys Ser Arg Trp
195 200 205

Gln Gln Gly Asn Val Phe Ser Cys Ser Val Met His Glu Ala Leu His
210 215 220

Asn His Tyr Thr Gln Lys Ser Leu Ser Leu Ser Pro Gly Lys
225 230 235

<210> SEQ ID NO 18
<211> LENGTH: 717
<212> TYPE: DNA
<213> ORGANISM: Artificial Sequence
<220> FEATURE:
<223> OTHER INFORMATION: Synthetic Construct

<400> SEQUENCE: 18
atgaaagctg tggtgctggc cgtggctctg gtcttcctga cagggagcca ggctcggcat 60
catcatcacc atcacggcgg gggaccgtca gtcttcctct tcccccaaa acccaaggac 120 accctcatga tctcccggac ccctgaggtc acatgcgtgg tggtggacgt gagccacgaa 180
gaccctgagg tcaagttcaa ctggtacgtg gacggcgtgg aggtgcataa tgccaagaca 240
aagccgcggg aggagcagta caacagcacg taccgtgtgg tcagcgtcct caccgtcctg 300
caccaggact ggctgaatgg caaggagtac aagtgcaagg tctccaacaa agccctccca 360
gcccccatcg agaaaaccat ctccaaagcc aaagggcagc cccgagaacc aaacgtgacc 420
accctgcccc catcccggga ggagatgacc aagaaccagg tcagcctgac ctgcctggtc 480
aaaggcttct atcccagcga catcgccgtg gagtgggaga gcaatgggca gccggagaac 540
aactacaaga ccacgcctcc cgtgctggac tccgacggct ccttcttcct ctatagcaag 600
ctcaccgtgg acaagagcag gtggcagcag gggaacgtct tctcatgctc cgtgatgcat 660
gaggctctgc acaaccacta cacgcagaag agcctctccc tgtccccggg taaatga 717

<210> SEQ ID NO 19
<211> LENGTH: 238
<212> TYPE: PRT
<213> ORGANISM: Artificial Sequence
<220> FEATURE:
<223> OTHER INFORMATION: Synthetic Construct

<400> SEQUENCE: 19

Met Lys Ala Val Val Leu Ala Val Ala Leu Val Phe Leu Thr Gly Ser
1 5 10 15

Gln Ala Arg His His His His His His Gly Gly Gly Pro Ser Val Phe
20 25 30

Leu Phe Pro Pro Lys Pro Lys Asp Thr Leu Met Ile Ser Arg Thr Pro
35 40 45

Glu Val Thr Cys Val Val Val Asp Val Ser His Glu Asp Pro Glu Val
50 55 60

Lys Phe Asn Trp Tyr Val Asp Gly Val Glu Val His Asn Ala Lys Thr
65 70 75 80

Lys Pro Arg Glu Glu Gln Tyr Asn Ser Thr Tyr Arg Val Val Ser Val
85 90 95

Leu Thr Val Leu His Gln Asp Trp Leu Asn Gly Lys Glu Tyr Lys Cys
100 105 110

Lys Val Ser Asn Lys Ala Leu Pro Ala Pro Ile Glu Lys Thr Ile Ser
115 120 125

Lys Ala Lys Gly Gln Pro Arg Glu Pro Gln Val Tyr Thr Leu Pro Pro
130 135 140

Ser Arg Glu Glu Met Thr Lys Asn Gln Val Asn Leu Thr Cys Leu Val
145 150 155 160

Lys Gly Phe Tyr Pro Ser Asp Ile Ala Val Glu Trp Glu Ser Asn Gly
165 170 175

Gln Pro Glu Asn Asn Tyr Lys Thr Thr Pro Pro Val Leu Asp Ser Asp
180 185 190

Gly Ser Phe Phe Leu Tyr Ser Lys Leu Thr Val Asp Lys Ser Arg Trp
195 200 205

Gln Gln Gly Asn Val Phe Ser Cys Ser Val Met His Glu Ala Leu His
210 215 220

Asn His Tyr Thr Gln Lys Ser Leu Ser Leu Ser Pro Gly Lys
225 230 235

<210> SEQ ID NO 20
<211> LENGTH: 717
<212> TYPE: DNA
<213> ORGANISM: Artificial Sequence
<220> FEATURE:
<223> OTHER INFORMATION: Synthetic Construct

<400> SEQUENCE: 20
atgaaagctg tggtgctggc cgtggctctg gtcttcctga cagggagcca ggctcggcat 60
catcatcacc atcacggcgg gggaccgtca gtcttcctct tccccccaaa acccaaggac 120
accctcatga tctcccggac ccctgaggtc acatgcgtgg tggtggacgt gagccacgaa 180
gaccctgagg tcaagttcaa ctggtacgtg gacggcgtgg aggtgcataa tgccaagaca 240
aagccgcggg aggagcagta caacagcacg taccgtgtgg tcagcgtcct caccgtcctg 300
caccaggact ggctgaatgg caaggagtac aagtgcaagg tctccaacaa agccctccca 360

-continued gcccccatcg agaaaaccat ctccaaagcc aaagggcagc cccgagaacc acaggtgtac 420
accctgcccc catcccggga ggagatgacc aagaaccagg tcaacctgac ctgcctggtc 480
aaaggcttct atcccagcga catcgccgtg gagtgggaga gcaatgggca gccggagaac 540
aactacaaga ccacgcctcc cgtgctggac tccgacggct ccttcttcct ctatagcaag 600
ctcaccgtgg acaagagcag gtggcagcag gggaacgtct tctcatgctc cgtgatgcat 660
gaggctctgc acaaccacta cacgcagaag agcctctccc tgtccccggg taaatga 717

<210> SEQ ID NO 21
<211> LENGTH: 238
<212> TYPE: PRT
<213> ORGANISM: Artificial Sequence
<220> FEATURE:
<223> OTHER INFORMATION: Synthetic Construct

<400> SEQUENCE: 21

Met Lys Ala Val Val Leu Ala Val Ala Leu Val Phe Leu Thr Gly Ser
1 5 10 15

Gln Ala Arg His His His His His His Gly Gly Gly Pro Ser Val Phe
20 25 30

Leu Phe Pro Pro Lys Pro Lys Asp Thr Leu Met Ile Ser Arg Thr Pro
35 40 45

Glu Val Thr Cys Val Val Val Asp Val Ser His Glu Asp Pro Glu Val
50 55 60

Lys Phe Asn Trp Tyr Val Asp Gly Val Glu Val His Asn Ala Lys Thr
65 70 75 80

Lys Pro Arg Glu Glu Gln Tyr Asn Ser Thr Tyr Arg Val Val Ser Val
85 90 95

Leu Thr Val Leu His Gln Asp Trp Leu Asn Gly Lys Glu Tyr Lys Cys
100 105 110

Lys Val Ser Asn Lys Ala Leu Pro Ala Pro Ile Glu Lys Thr Ile Ser
115 120 125

Lys Ala Lys Gly Gln Pro Arg Glu Pro Gln Val Tyr Thr Leu Pro Pro
130 135 140

Ser Arg Glu Glu Met Thr Lys Asn Gln Val Ser Leu Asn Cys Thr Val
145 150 155 160

Lys Gly Phe Tyr Pro Ser Asp Ile Ala Val Glu Trp Glu Ser Asn Gly
165 170 175

Gln Pro Glu Asn Asn Tyr Lys Thr Thr Pro Pro Val Leu Asp Ser Asp
180 185 190

Gly Ser Phe Phe Leu Tyr Ser Lys Leu Thr Val Asp Lys Ser Arg Trp
195 200 205

Gln Gln Gly Asn Val Phe Ser Cys Ser Val Met His Glu Ala Leu His
210 215 220

Asn His Tyr Thr Gln Lys Ser Leu Ser Leu Ser Pro Gly Lys
225 230 235

<210> SEQ ID NO 22
<211> LENGTH: 717
<212> TYPE: DNA
<213> ORGANISM: Artificial Sequence
<220> FEATURE:
<223> OTHER INFORMATION: Synthetic Construct

<400> SEQUENCE: 22
atgaaagctg tggtgctggc cgtggctctg gtcttcctga cagggagcca ggctcggcat 60

```
catcatcacc atcacggcgg gggaccgtca gtcttcctct tccccccaaa acccaaggac    120

accctcatga tctcccggac ccctgaggtc acatgcgtgg tggtggacgt gagccacgaa    180

gaccctgagg tcaagttcaa ctggtacgtg gacggcgtgg aggtgcataa tgccaagaca    240

aagccgcggg aggagcagta caacagcacg taccgtgtgg tcagcgtcct caccgtcctg    300

caccaggact ggctgaatgg caaggagtac aagtgcaagg tctccaacaa agccctccca    360

gcccccatcg agaaaaccat ctccaaagcc aaagggcagc cccgagaacc acaggtgtac    420

accctgcccc catcccggga ggagatgacc aagaaccagg tcagcctgaa ctgcaccgtc    480

aaaggcttct atcccagcga catcgccgtg gagtgggaga gcaatgggca gccggagaac    540

aactacaaga ccacgcctcc cgtgctggac tccgacggct ccttcttcct ctatagcaag    600

ctcaccgtgg acaagagcag gtggcagcag gggaacgtct tctcatgctc cgtgatgcat    660

gaggctctgc acaaccacta cacgcagaag agcctctccc tgtccccggg taaatga       717

<210> SEQ ID NO 23
<211> LENGTH: 238
<212> TYPE: PRT
<213> ORGANISM: Artificial Sequence
<220> FEATURE:
<223> OTHER INFORMATION: Synthetic Construct

<400> SEQUENCE: 23

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Asn Val
145                 150                 155                 160

Thr Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235

<210> SEQ ID NO 24
```

```
<211> LENGTH: 717
<212> TYPE: DNA
<213> ORGANISM: Artificial Sequence
<220> FEATURE:
<223> OTHER INFORMATION: Synthetic Construct

<400> SEQUENCE: 24

atgaaagctg tggtgctggc cgtggctctg gtcttcctga cagggagcca ggctcggcat     60

catcatcacc atcacggcgg gggaccgtca gtcttcctct tccccccaaa acccaaggac    120

accctcatga tctcccggac ccctgaggtc acatgcgtgg tggtggacgt gagccacgaa    180

gaccctgagg tcaagttcaa ctggtacgtg gacggcgtgg aggtgcataa tgccaagaca    240

aagccgcggg aggagcagta caacagcacg taccgtgtgg tcagcgtcct caccgtcctg    300

caccaggact ggctgaatgg caaggagtac aagtgcaagg tctccaacaa agccctccca    360

gcccccatcg agaaaaccat ctccaaagcc aaagggcagc cccgagaacc acaggtgtac    420

accctgcccc catcccggga ggagatgacc aagaaccagg tcagcctgac ctgcaacgtc    480

accggcttct atcccagcga catcgccgtg gagtgggaga gcaatgggca gccggagaac    540

aactacaaga ccacgcctcc cgtgctggac tccgacggct ccttcttcct ctatagcaag    600

ctcaccgtgg acaagagcag gtggcagcag gggaacgtct tctcatgctc cgtgatgcat    660

gaggctctgc acaaccacta cacgcagaag agcctctccc tgtccccggg taaatga       717

<210> SEQ ID NO 25
<211> LENGTH: 238
<212> TYPE: PRT
<213> ORGANISM: Artificial Sequence
<220> FEATURE:
<223> OTHER INFORMATION: Synthetic Construct

<400> SEQUENCE: 25

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Thr Thr Thr Pro Pro Val Leu Asp Ser Asp
            180                 185                 190

Gly Ser Phe Phe Leu Tyr Ser Lys Leu Thr Val Asp Lys Ser Arg Trp
```

```
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235


<210> SEQ ID NO 26
<211> LENGTH: 717
<212> TYPE: DNA
<213> ORGANISM: Artificial Sequence
<220> FEATURE:
<223> OTHER INFORMATION: Synthetic Construct

<400> SEQUENCE: 26

atgaaagctg tggtgctggc cgtggctctg gtcttcctga cagggagcca ggctcggcat      60

catcatcacc atcacggcgg gggaccgtca gtcttcctct tccccccaaa acccaaggac     120

accctcatga tctcccggac ccctgaggtc acatgcgtgg tggtggacgt gagccacgaa     180

gaccctgagg tcaagttcaa ctggtacgtg gacggcgtgg aggtgcataa tgccaagaca     240

aagccgcggg aggagcagta caacagcacg taccgtgtgg tcagcgtcct caccgtcctg     300

caccaggact ggctgaatgg caaggagtac aagtgcaagg tctccaacaa agccctccca     360

gcccccatcg agaaaaccat ctccaaagcc aaagggcagc cccgagaacc acaggtgtac     420

accctgcccc catcccggga ggagatgacc aagaaccagg tcagcctgac ctgcctggtc     480

aaaggcttct atcccagcga catcgccgtg gagtgggaga gcaatgggca gccggagaac     540

aactacacca ccacgcctcc cgtgctggac tccgacggct ccttcttcct ctatagcaag     600

ctcaccgtgg acaagagcag gtggcagcag gggaacgtct tctcatgctc cgtgatgcat     660

gaggctctgc acaaccacta cacgcagaag agcctctccc tgtccccggg taaatga        717


<210> SEQ ID NO 27
<211> LENGTH: 238
<212> TYPE: PRT
<213> ORGANISM: Artificial Sequence
<220> FEATURE:
<223> OTHER INFORMATION: Synthetic Construct

<400> SEQUENCE: 27

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140
```

```
Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asn
            180                 185                 190

Gly Thr Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235


<210> SEQ ID NO 28
<211> LENGTH: 717
<212> TYPE: DNA
<213> ORGANISM: Artificial Sequence
<220> FEATURE:
<223> OTHER INFORMATION: Synthetic Construct

<400> SEQUENCE: 28

atgaaagctg tggtgctggc cgtggctctg gtcttcctga cagggagcca ggctcggcat      60

catcatcacc atcacggcgg gggaccgtca gtcttcctct tccccccaaa acccaaggac     120

accctcatga tctcccggac ccctgaggtc acatgcgtgg tggtggacgt gagccacgaa     180

gaccctgagg tcaagttcaa ctggtacgtg gacggcgtgg aggtgcataa tgccaagaca     240

aagccgcggg aggagcagta caacagcacg taccgtgtgg tcagcgtcct caccgtcctg     300

caccaggact ggctgaatgg caaggagtac aagtgcaagg tctccaacaa agccctccca     360

gcccccatcg agaaaaccat ctccaaagcc aaagggcagc cccgagaacc acaggtgtac     420

accctgcccc catcccggga ggagatgacc aagaaccagg tcagcctgac ctgcctggtc     480

aaaggcttct atcccagcga catcgccgtg gagtgggaga gcaatgggca gccggagaac     540

aactacaaga ccacgcctcc cgtgctggac tccaacggca ccttcttcct ctatagcaag     600

ctcaccgtgg acaagagcag gtggcagcag gggaacgtct tctcatgctc cgtgatgcat     660

gaggctctgc acaaccacta cacgcagaag agcctctccc tgtccccggg taaatga        717


<210> SEQ ID NO 29
<211> LENGTH: 238
<212> TYPE: PRT
<213> ORGANISM: Artificial Sequence
<220> FEATURE:
<223> OTHER INFORMATION: Synthetic Construct

<400> SEQUENCE: 29

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95
```

```
Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Asn Leu Thr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235

<210> SEQ ID NO 30
<211> LENGTH: 717
<212> TYPE: DNA
<213> ORGANISM: Artificial Sequence
<220> FEATURE:
<223> OTHER INFORMATION: Synthetic Construct

<400> SEQUENCE: 30

atgaaagctg tggtgctggc cgtggctctg gtcttcctga cagggagcca ggctcggcat      60

catcatcacc atcacggcgg gggaccgtca gtcttcctct tccccccaaa acccaaggac     120

accctcatga tctcccggac ccctgaggtc acatgcgtgg tggtggacgt gagccacgaa     180

gaccctgagg tcaagttcaa ctggtacgtg gacggcgtgg aggtgcataa tgccaagaca     240

aagccgcggg aggagcagta caacagcacg taccgtgtgg tcagcgtcct caccgtcctg     300

caccaggact ggctgaatgg caaggagtac aagtgcaagg tctccaacaa agccctccca     360

gcccccatcg agaaaaccat ctccaaagcc aaagggcagc cccgagaacc acaggtgtac     420

accctgcccc catcccggga ggagatgacc aagaaccagg tcagcctgac ctgcctggtc     480

aaaggcttct atcccagcga catcgccgtg gagtgggaga gcaatgggca gccggagaac     540

aactacaaga ccacgcctcc cgtgctggac tccgacggct ccttcaacct caccagcaag     600

ctcaccgtgg acaagagcag gtggcagcag gggaacgtct tctcatgctc cgtgatgcat     660

gaggctctgc acaaccacta cacgcagaag agcctctccc tgtccccggg taaatga        717

<210> SEQ ID NO 31
<211> LENGTH: 238
<212> TYPE: PRT
<213> ORGANISM: Artificial Sequence
<220> FEATURE:
<223> OTHER INFORMATION: Synthetic Construct

<400> SEQUENCE: 31

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
```

```
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Asn Ser Thr Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

<210> SEQ ID NO 32
<211> LENGTH: 717
<212> TYPE: DNA
<213> ORGANISM: Artificial Sequence
<220> FEATURE:
<223> OTHER INFORMATION: Synthetic Construct

<400> SEQUENCE: 32

```
atgaaagctg tggtgctggc cgtggctctg gtcttcctga cagggagcca ggctcggcat      60

catcatcacc atcacggcgg gggaccgtca gtcttcctct tccccccaaa acccaaggac     120

accctcatga tctcccggac ccctgaggtc acatgcgtgg tggtggacgt gagccacgaa     180

gaccctgagg tcaagttcaa ctggtacgtg gacggcgtgg aggtgcataa tgccaagaca     240

aagccgcggg aggagcagta caacagcacg taccgtgtgg tcagcgtcct caccgtcctg     300

caccaggact ggctgaatgg caaggagtac aagtgcaagg tctccaacaa agccctccca     360

gcccccatcg agaaaaccat ctccaaagcc aaagggcagc cccgagaacc acaggtgtac     420

accctgcccc catcccggga ggagatgacc aagaaccagg tcagcctgac ctgcctggtc     480

aaaggcttct atcccagcga catcgccgtg gagtgggaga gcaatgggca gccggagaac     540

aactacaaga ccacgcctcc cgtgctggac tccgacggct ccttcttcct caacagcacc     600

ctcaccgtgg acaagagcag gtggcagcag gggaacgtct tctcatgctc cgtgatgcat     660

gaggctctgc acaaccacta cacgcagaag agcctctccc tgtccccggg taaatga        717
```

<210> SEQ ID NO 33
<211> LENGTH: 238
<212> TYPE: PRT
<213> ORGANISM: Artificial Sequence
<220> FEATURE:
<223> OTHER INFORMATION: Synthetic Construct

<400> SEQUENCE: 33

```
Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Asn Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

<210> SEQ ID NO 34
<211> LENGTH: 717
<212> TYPE: DNA
<213> ORGANISM: Artificial Sequence
<220> FEATURE:
<223> OTHER INFORMATION: Synthetic Construct

<400> SEQUENCE: 34

```
atgaaagctg tggtgctggc cgtggctctg gtcttcctga cagggagcca ggctcggcat     60

catcatcacc atcacggcgg gggaccgtca gtcttcctct tccccccaaa acccaaggac    120

accctcatga tctcccggac ccctgaggtc acatgcgtgg tggtggacgt gagccacgaa    180

gaccctgagg tcaagttcaa ctggtacgtg gacggcgtgg aggtgcataa tgccaagaca    240

aagccgcggg aggagcagta caacagcacg taccgtgtgg tcagcgtcct caccgtcctg    300

caccaggact ggctgaatgg caaggagtac aagtgcaagg tctccaacaa agccctccca    360

gcccccatcg agaaaaccat ctccaaagcc aaagggcagc cccgagaacc acaggtgtac    420

accctgcccc catcccggga ggagatgacc aagaaccagg tcagcctgac ctgcctggtc    480

aaaggcttct atcccagcga catcgccgtg gagtgggaga gcaatgggca gccggagaac    540

aactacaaga ccacgcctcc cgtgctggac tccgacggct ccttcttcct ctatagcaac    600

ctcaccgtgg acaagagcag gtggcagcag gggaacgtct tctcatgctc cgtgatgcat    660
```

gaggctctgc acaaccacta cacgcagaag agcctctccc tgtccccggg taaatga 717

<210> SEQ ID NO 35
<211> LENGTH: 238
<212> TYPE: PRT
<213> ORGANISM: Artificial Sequence
<220> FEATURE:
<223> OTHER INFORMATION: Synthetic Construct

<400> SEQUENCE: 35

Met Lys Ala Val Val Leu Ala Val Ala Leu Val Phe Leu Thr Gly Ser
1 5 10 15

Gln Ala Arg His His His His His His Gly Gly Gly Pro Ser Val Phe
20 25 30

Leu Phe Pro Pro Lys Pro Lys Asp Thr Leu Met Ile Ser Arg Thr Pro
35 40 45

Glu Val Thr Cys Val Val Val Asp Val Ser Gln Glu Asp Pro Glu Val
50 55 60

Gln Phe Asn Trp Tyr Val Asp Gly Val Glu Val His Asn Ala Lys Thr
65 70 75 80

Lys Pro Arg Glu Glu Gln Phe Asn Ser Thr Tyr Arg Val Val Ser Val
85 90 95

Leu Thr Val Leu His Gln Asp Trp Leu Asn Gly Lys Glu Tyr Lys Cys
100 105 110

Lys Val Ser Asn Lys Gly Leu Pro Ser Ser Ile Glu Lys Thr Ile Ser
115 120 125

Lys Ala Lys Gly Gln Pro Arg Glu Pro Asn Val Thr Thr Leu Pro Pro
130 135 140

Ser Gln Glu Glu Met Thr Lys Asn Gln Val Ser Leu Thr Cys Leu Val
145 150 155 160

Lys Gly Phe Tyr Pro Ser Asp Ile Ala Val Glu Trp Glu Ser Asn Gly
165 170 175

Gln Pro Glu Asn Asn Tyr Lys Thr Thr Pro Pro Val Leu Asp Ser Asp
180 185 190

Gly Ser Phe Phe Leu Tyr Ser Arg Leu Thr Val Asp Lys Ser Arg Trp
195 200 205

Gln Glu Gly Asn Val Phe Ser Cys Ser Val Met His Glu Ala Leu His
210 215 220

Asn His Tyr Thr Gln Lys Ser Leu Ser Leu Ser Leu Gly Lys
225 230 235

<210> SEQ ID NO 36
<211> LENGTH: 717
<212> TYPE: DNA
<213> ORGANISM: Artificial Sequence
<220> FEATURE:
<223> OTHER INFORMATION: Synthetic Construct

<400> SEQUENCE: 36
atgaaagctg tggtgctggc cgtggctctg gtcttcctga cagggagcca ggctcggcat 60
catcatcacc atcacggcgg gggaccatca gtcttcctgt tcccccaaa acccaaggac 120 actctcatga tctcccggac ccctgaggtc acgtgcgtgg tggtggacgt gagccaggaa 180
gaccccgagg tccagttcaa ctggtacgtg gatggcgtgg aggtgcataa tgccaagaca 240
aagccgcggg aggagcagtt caacagcacg taccgtgtgg tcagcgtcct caccgtcctg 300
caccaggact ggctgaacgg caaggagtac aagtgcaagg tctccaacaa aggcctcccg 360

```
tcctccatcg agaaaaccat ctccaaagcc aaaggtcagc cccgagagcc aaacgtgacc    420

accctgcccc catcccagga ggagatgacc aagaaccagg tcagcctgac ctgcctggtc    480

aaaggcttct accccagcga catcgccgtg gagtgggaga gcaatgggca gccggagaac    540

aactacaaga ccacgcctcc cgtgctggac tccgacggct ccttcttcct ctacagcagg    600

ctaaccgtgg acaagagcag gtggcaggag gggaatgtct tctcatgctc cgtgatgcat    660

gaggctctgc acaaccacta cacacagaag agcctctccc tgtctctggg taaatga       717


<210> SEQ ID NO 37
<211> LENGTH: 238
<212> TYPE: PRT
<213> ORGANISM: Artificial Sequence
<220> FEATURE:
<223> OTHER INFORMATION: Synthetic Construct

<400> SEQUENCE: 37

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser Gln Glu Asp Pro Glu Val
    50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Gly Leu Pro Ser Ser Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Gln Glu Glu Met Thr Lys Asn Gln Val Asn Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Arg Leu Thr Val Asp Lys Ser Arg Trp
        195                 200                 205

Gln Glu Gly Asn Val Phe Ser Cys Ser Val Met His Glu Ala Leu His
    210                 215                 220

Asn His Tyr Thr Gln Lys Ser Leu Ser Leu Ser Leu Gly Lys
225                 230                 235


<210> SEQ ID NO 38
<211> LENGTH: 717
<212> TYPE: DNA
<213> ORGANISM: Artificial Sequence
<220> FEATURE:
<223> OTHER INFORMATION: Synthetic Construct

<400> SEQUENCE: 38

atgaaagctg tggtgctggc cgtggctctg gtcttcctga cagggagcca ggctcggcat     60
```

```
catcatcacc atcacggcgg gggaccatca gtcttcctgt tccccccaaa acccaaggac    120

actctcatga tctcccggac ccctgaggtc acgtgcgtgg tggtggacgt gagccaggaa    180

gaccccgagg tccagttcaa ctggtacgtg gatggcgtgg aggtgcataa tgccaagaca    240

aagccgcggg aggagcagtt caacagcacg taccgtgtgg tcagcgtcct caccgtcctg    300

caccaggact ggctgaacgg caaggagtac aagtgcaagg tctccaacaa aggcctcccg    360

tcctccatcg agaaaaccat ctccaaagcc aaaggtcagc cccgagagcc acaggtgtac    420

accctgcccc catcccagga ggagatgacc aagaaccagg tcaacctgac ctgcctggtc    480

aaaggcttct accccagcga catcgccgtg gagtgggaga gcaatgggca gccggagaac    540

aactacaaga ccacgcctcc cgtgctggac tccgacggct ccttcttcct ctacagcagg    600

ctaaccgtgg acaagagcag gtggcaggag gggaatgtct tctcatgctc cgtgatgcat    660

gaggctctgc acaaccacta cacacagaag agcctctccc tgtctctggg taaatga       717
```

<210> SEQ ID NO 39
<211> LENGTH: 238
<212> TYPE: PRT
<213> ORGANISM: Artificial Sequence
<220> FEATURE:
<223> OTHER INFORMATION: Synthetic Construct

<400> SEQUENCE: 39

```
Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser Gln Glu Asp Pro Glu Val
    50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Gly Leu Pro Ser Ser Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Gln Glu Glu Met Thr Lys Asn Gln Val Ser Leu Asn Cys Thr Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Arg Leu Thr Val Asp Lys Ser Arg Trp
        195                 200                 205

Gln Glu Gly Asn Val Phe Ser Cys Ser Val Met His Glu Ala Leu His
    210                 215                 220

Asn His Tyr Thr Gln Lys Ser Leu Ser Leu Ser Leu Gly Lys
225                 230                 235
```

-continued

<210> SEQ ID NO 40
<211> LENGTH: 717
<212> TYPE: DNA
<213> ORGANISM: Artificial Sequence
<220> FEATURE:
<223> OTHER INFORMATION: Synthetic Construct

<400> SEQUENCE: 40

```
atgaaagctg tggtgctggc cgtggctctg gtcttcctga cagggagcca ggctcggcat      60

catcatcacc atcacggcgg gggaccatca gtcttcctgt tcccccccaaa acccaaggac    120

actctcatga tctcccggac ccctgaggtc acgtgcgtgg tggtggacgt gagccaggaa    180

gaccccgagg tccagttcaa ctggtacgtg gatggcgtgg aggtgcataa tgccaagaca    240

aagccgcggg aggagcagtt caacagcacg taccgtgtgg tcagcgtcct caccgtcctg    300

caccaggact ggctgaacgg caaggagtac aagtgcaagg tctccaacaa aggcctcccg    360

tcctccatcg agaaaaccat ctccaaagcc aaaggtcagc cccgagagcc acaggtgtac    420

accctgcccc catcccagga ggagatgacc aagaaccagg tcagcctgaa ctgcaccgtc    480

aaaggcttct accccagcga catcgccgtg gagtgggaga gcaatgggca gccggagaac    540

aactacaaga ccacgcctcc cgtgctggac tccgacggct ccttcttcct ctacagcagg    600

ctaaccgtgg acaagagcag gtggcaggag gggaatgtct tctcatgctc cgtgatgcat    660

gaggctctgc acaaccacta cacacagaag agcctctccc tgtctctggg taaatga       717
```

<210> SEQ ID NO 41
<211> LENGTH: 238
<212> TYPE: PRT
<213> ORGANISM: Artificial Sequence
<220> FEATURE:
<223> OTHER INFORMATION: Synthetic Construct

<400> SEQUENCE: 41

```
Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser Gln Glu Asp Pro Glu Val
    50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Gly Leu Pro Ser Ser Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Gln Glu Glu Met Thr Lys Asn Gln Val Ser Leu Thr Cys Asn Val
145                 150                 155                 160

Thr Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190
```

```
Gly Ser Phe Phe Leu Tyr Ser Arg Leu Thr Val Asp Lys Ser Arg Trp
        195                 200                 205

Gln Glu Gly Asn Val Phe Ser Cys Ser Val Met His Glu Ala Leu His
    210                 215                 220

Asn His Tyr Thr Gln Lys Ser Leu Ser Leu Ser Leu Gly Lys
225                 230                 235

<210> SEQ ID NO 42
<211> LENGTH: 717
<212> TYPE: DNA
<213> ORGANISM: Artificial Sequence
<220> FEATURE:
<223> OTHER INFORMATION: Synthetic Construct

<400> SEQUENCE: 42

atgaaagctg tggtgctggc cgtggctctg gtcttcctga cagggagcca ggctcggcat      60

catcatcacc atcacggcgg gggaccatca gtcttcctgt tccccccaaa acccaaggac     120

actctcatga tctcccggac ccctgaggtc acgtgcgtgg tggtggacgt gagccaggaa     180

gaccccgagg tccagttcaa ctggtacgtg gatggcgtgg aggtgcataa tgccaagaca     240

aagccgcggg aggagcagtt caacagcacg taccgtgtgg tcagcgtcct caccgtcctg     300

caccaggact ggctgaacgg caaggagtac aagtgcaagg tctccaacaa aggcctcccg     360

tcctccatcg agaaaaccat ctccaaagcc aaaggtcagc cccgagagcc acaggtgtac     420

accctgcccc catcccagga ggagatgacc aagaaccagg tcagcctgac ctgcaacgtc     480

accggcttct accccagcga catcgccgtg gagtgggaga gcaatgggca gccggagaac     540

aactacaaga ccacgcctcc cgtgctggac tccgacggct ccttcttcct ctacagcagg     600

ctaaccgtgg acaagagcag gtggcaggag gggaatgtct tctcatgctc cgtgatgcat     660

gaggctctgc acaaccacta cacacagaag agcctctccc tgtctctggg taaatga        717

<210> SEQ ID NO 43
<211> LENGTH: 238
<212> TYPE: PRT
<213> ORGANISM: Artificial Sequence
<220> FEATURE:
<223> OTHER INFORMATION: Synthetic Construct

<400> SEQUENCE: 43

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser Gln Glu Asp Pro Glu Val
    50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Gly Leu Pro Ser Ser Ile Glu Lys Thr Ile Ser
        115                 120                 125

Lys Ala Lys Gly Gln Pro Arg Glu Pro Gln Val Tyr Thr Leu Pro Pro
    130                 135                 140
```

```
Ser Gln Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Thr Thr Thr Pro Pro Val Leu Asp Ser Asp
            180                 185                 190

Gly Ser Phe Phe Leu Tyr Ser Arg Leu Thr Val Asp Lys Ser Arg Trp
        195                 200                 205

Gln Glu Gly Asn Val Phe Ser Cys Ser Val Met His Glu Ala Leu His
    210                 215                 220

Asn His Tyr Thr Gln Lys Ser Leu Ser Leu Ser Leu Gly Lys
225                 230                 235


<210> SEQ ID NO 44
<211> LENGTH: 717
<212> TYPE: DNA
<213> ORGANISM: Artificial Sequence
<220> FEATURE:
<223> OTHER INFORMATION: Synthetic Construct

<400> SEQUENCE: 44

atgaaagctg tggtgctggc cgtggctctg gtcttcctga cagggagcca ggctcggcat      60

catcatcacc atcacggcgg gggaccatca gtcttcctgt tcccccccaaa acccaaggac    120

actctcatga tctcccggac ccctgaggtc acgtgcgtgg tggtggacgt gagccaggaa     180

gaccccgagg tccagttcaa ctggtacgtg gatggcgtgg aggtgcataa tgccaagaca     240

aagccgcggg aggagcagtt caacagcacg taccgtgtgg tcagcgtcct caccgtcctg     300

caccaggact ggctgaacgg caaggagtac aagtgcaagg tctccaacaa aggcctcccg     360

tcctccatcg agaaaaccat ctccaaagcc aaaggtcagc cccgagagcc acaggtgtac     420

accctgcccc catcccagga ggagatgacc aagaaccagg tcagcctgac ctgcctggtc     480

aaaggcttct accccagcga catcgccgtg gagtgggaga gcaatgggca gccggagaac     540

aactacacca ccacgcctcc cgtgctggac tccgacggct ccttcttcct ctacagcagg     600

ctaaccgtgg acaagagcag gtggcaggag gggaatgtct tctcatgctc cgtgatgcat     660

gaggctctgc acaaccacta cacacagaag agcctctccc tgtctctggg taaatga        717


<210> SEQ ID NO 45
<211> LENGTH: 238
<212> TYPE: PRT
<213> ORGANISM: Artificial Sequence
<220> FEATURE:
<223> OTHER INFORMATION: Synthetic Construct

<400> SEQUENCE: 45

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser Gln Glu Asp Pro Glu Val
    50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Tyr Arg Val Val Ser Val
```

-continued

```
                85                  90                  95

Leu Thr Val Leu His Gln Asp Trp Leu Asn Gly Lys Glu Tyr Lys Cys
            100                 105                 110

Lys Val Ser Asn Lys Gly Leu Pro Ser Ser Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Gln Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asn
            180                 185                 190

Gly Thr Phe Phe Leu Tyr Ser Arg Leu Thr Val Asp Lys Ser Arg Trp
        195                 200                 205

Gln Glu Gly Asn Val Phe Ser Cys Ser Val Met His Glu Ala Leu His
    210                 215                 220

Asn His Tyr Thr Gln Lys Ser Leu Ser Leu Ser Leu Gly Lys
225                 230                 235
```

<210> SEQ ID NO 46
<211> LENGTH: 717
<212> TYPE: DNA
<213> ORGANISM: Artificial Sequence
<220> FEATURE:
<223> OTHER INFORMATION: Synthetic Construct

<400> SEQUENCE: 46

```
atgaaagctg tggtgctggc cgtggctctg gtcttcctga cagggagcca ggctcggcat     60

catcatcacc atcacggcgg gggaccatca gtcttcctgt tccccccaaa acccaaggac    120

actctcatga tctcccggac ccctgaggtc acgtgcgtgg tggtggacgt gagccaggaa    180

gaccccgagg tccagttcaa ctggtacgtg gatggcgtgg aggtgcataa tgccaagaca    240

aagccgcggg aggagcagtt caacagcacg taccgtgtgg tcagcgtcct caccgtcctg    300

caccaggact ggctgaacgg caaggagtac aagtgcaagg tctccaacaa aggcctcccg    360

tcctccatcg agaaaaccat ctccaaagcc aaaggtcagc cccgagagcc acaggtgtac    420

accctgcccc catcccagga ggagatgacc aagaaccagg tcagcctgac ctgcctggtc    480

aaaggcttct accccagcga catcgccgtg gagtgggaga gcaatgggca gccggagaac    540

aactacaaga ccacgcctcc cgtgctggac tccaacggca ccttcttcct ctacagcagg    600

ctaaccgtgg acaagagcag gtggcaggag gggaatgtct tctcatgctc cgtgatgcat    660

gaggctctgc acaaccacta cacacagaag agcctctccc tgtctctggg taaatga       717
```

<210> SEQ ID NO 47
<211> LENGTH: 238
<212> TYPE: PRT
<213> ORGANISM: Artificial Sequence
<220> FEATURE:
<223> OTHER INFORMATION: Synthetic Construct

<400> SEQUENCE: 47

```
Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30
```

```
Leu Phe Pro Pro Lys Pro Lys Asp Thr Leu Met Ile Ser Arg Thr Pro
        35                  40                  45

Glu Val Thr Cys Val Val Val Asp Val Ser Gln Glu Asp Pro Glu Val
    50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Gly Leu Pro Ser Ser Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Gln Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Asn Leu Thr Ser Arg Leu Thr Val Asp Lys Ser Arg Trp
        195                 200                 205

Gln Glu Gly Asn Val Phe Ser Cys Ser Val Met His Glu Ala Leu His
    210                 215                 220

Asn His Tyr Thr Gln Lys Ser Leu Ser Leu Ser Leu Gly Lys
225                 230                 235


<210> SEQ ID NO 48
<211> LENGTH: 717
<212> TYPE: DNA
<213> ORGANISM: Artificial Sequence
<220> FEATURE:
<223> OTHER INFORMATION: Synthetic Construct

<400> SEQUENCE: 48

atgaaagctg tggtgctggc cgtggctctg gtcttcctga cagggagcca ggctcggcat     60

catcatcacc atcacggcgg gggaccatca gtcttcctgt tccccccaaa acccaaggac    120

actctcatga tctcccggac ccctgaggtc acgtgcgtgg tggtggacgt gagccaggaa    180

gaccccgagg tccagttcaa ctggtacgtg gatggcgtgg aggtgcataa tgccaagaca    240

aagccgcggg aggagcagtt caacagcacg taccgtgtgg tcagcgtcct caccgtcctg    300

caccaggact ggctgaacgg caaggagtac aagtgcaagg tctccaacaa aggcctcccg    360

tcctccatcg agaaaaccat ctccaaagcc aaaggtcagc cccgagagcc acaggtgtac    420

accctgcccc catcccagga ggagatgacc aagaaccagg tcagcctgac ctgcctggtc    480

aaaggcttct accccagcga catcgccgtg gagtgggaga gcaatgggca gccggagaac    540

aactacaaga ccacgcctcc cgtgctggac tccgacggct ccttcaacct caccagcagg    600

ctaaccgtgg acaagagcag gtggcaggag gggaatgtct tctcatgctc cgtgatgcat    660

gaggctctgc acaaccacta cacacagaag agcctctccc tgtctctggg taaatga       717


<210> SEQ ID NO 49
<211> LENGTH: 238
<212> TYPE: PRT
<213> ORGANISM: Artificial Sequence
<220> FEATURE:
```

<223> OTHER INFORMATION: Synthetic Construct

<400> SEQUENCE: 49

```
Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser Gln Glu Asp Pro Glu Val
    50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Gly Leu Pro Ser Ser Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Gln Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Asn Ser Thr Leu Thr Val Asp Lys Ser Arg Trp
        195                 200                 205

Gln Glu Gly Asn Val Phe Ser Cys Ser Val Met His Glu Ala Leu His
    210                 215                 220

Asn His Tyr Thr Gln Lys Ser Leu Ser Leu Ser Leu Gly Lys
225                 230                 235
```

<210> SEQ ID NO 50
<211> LENGTH: 717
<212> TYPE: DNA
<213> ORGANISM: Artificial Sequence
<220> FEATURE:
<223> OTHER INFORMATION: Synthetic Construct

<400> SEQUENCE: 50

```
atgaaagctg tggtgctggc cgtggctctg gtcttcctga cagggagcca ggctcggcat     60

catcatcacc atcacggcgg gggaccatca gtcttcctgt tcccccccaaa acccaaggac    120

actctcatga tctcccggac ccctgaggtc acgtgcgtgg tggtggacgt gagccaggaa    180

gaccccgagg tccagttcaa ctggtacgtg gatggcgtgg aggtgcataa tgccaagaca    240

aagccgcggg aggagcagtt caacagcacg taccgtgtgg tcagcgtcct caccgtcctg    300

caccaggact ggctgaacgg caaggagtac aagtgcaagg tctccaacaa aggcctcccg    360

tcctccatcg agaaaaccat ctccaaagcc aaaggtcagc cccgagagcc acaggtgtac    420

accctgcccc catcccagga ggagatgacc aagaaccagg tcagcctgac ctgcctggtc    480

aaaggcttct accccagcga catcgccgtg gagtgggaga gcaatgggca gccggagaac    540

aactacaaga ccacgcctcc cgtgctggac tccgacggct ccttcttcct caacagcacc    600
```

```
ctaaccgtgg acaagagcag gtggcaggag gggaatgtct tctcatgctc cgtgatgcat    660

gaggctctgc acaaccacta cacacagaag agcctctccc tgtctctggg taaatga       717

<210> SEQ ID NO 51
<211> LENGTH: 238
<212> TYPE: PRT
<213> ORGANISM: Artificial Sequence
<220> FEATURE:
<223> OTHER INFORMATION: Synthetic Construct

<400> SEQUENCE: 51

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser Gln Glu Asp Pro Glu Val
    50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Gly Leu Pro Ser Ser Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Gln Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Asn Leu Thr Val Asp Lys Ser Arg Trp
        195                 200                 205

Gln Glu Gly Asn Val Phe Ser Cys Ser Val Met His Glu Ala Leu His
    210                 215                 220

Asn His Tyr Thr Gln Lys Ser Leu Ser Leu Ser Leu Gly Lys
225                 230                 235

<210> SEQ ID NO 52
<211> LENGTH: 717
<212> TYPE: DNA
<213> ORGANISM: Artificial Sequence
<220> FEATURE:
<223> OTHER INFORMATION: Synthetic Construct

<400> SEQUENCE: 52

atgaaagctg tggtgctggc cgtggctctg gtcttcctga cagggagcca ggctcggcat     60

catcatcacc atcacggcgg gggaccatca gtcttcctgt tccccccaaa acccaaggac    120

actctcatga tctcccggac ccctgaggtc acgtgcgtgg tggtggacgt gagccaggaa    180

gaccccgagg tccagttcaa ctggtacgtg gatggcgtgg aggtgcataa tgccaagaca    240

aagccgcggg aggagcagtt caacagcacg taccgtgtgg tcagcgtcct caccgtcctg    300
```

-continued

```
caccaggact ggctgaacgg caaggagtac aagtgcaagg tctccaacaa aggcctcccg    360

tcctccatcg agaaaaccat ctccaaagcc aaaggtcagc cccgagagcc acaggtgtac    420

accctgcccc catcccagga ggagatgacc aagaaccagg tcagcctgac ctgcctggtc    480

aaaggcttct accccagcga catcgccgtg gagtgggaga gcaatgggca gccggagaac    540

aactacaaga ccacgcctcc cgtgctggac tccgacggct ccttcttcct ctacagcaac    600

ctaaccgtgg acaagagcag gtggcaggag gggaatgtct tctcatgctc cgtgatgcat    660

gaggctctgc acaaccacta cacacagaag agcctctccc tgtctctggg taaatga       717
```

<210> SEQ ID NO 53
<211> LENGTH: 238
<212> TYPE: PRT
<213> ORGANISM: Artificial Sequence
<220> FEATURE:
<223> OTHER INFORMATION: Synthetic Construct

<400> SEQUENCE: 53

```
Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Asn Leu Thr Cys Asn Val
145                 150                 155                 160

Thr Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

<210> SEQ ID NO 54
<211> LENGTH: 717
<212> TYPE: DNA
<213> ORGANISM: Artificial Sequence
<220> FEATURE:
<223> OTHER INFORMATION: Synthetic Construct

<400> SEQUENCE: 54

-continued

```
atgaaagctg tggtgctggc cgtggctctg gtcttcctga cagggagcca ggctcggcat      60

catcatcacc atcacggcgg gggaccgtca gtcttcctct tccccccaaa acccaaggac     120

accctcatga tctcccggac ccctgaggtc acatgcgtgg tggtggacgt gagccacgaa     180

gaccctgagg tcaagttcaa ctggtacgtg gacggcgtgg aggtgcataa tgccaagaca     240

aagccgcggg aggagcagta caacagcacg taccgtgtgg tcagcgtcct caccgtcctg     300

caccaggact ggctgaatgg caaggagtac aagtgcaagg tctccaacaa agccctccca     360

gcccccatcg agaaaaccat ctccaaagcc aaagggcagc cccgagaacc acaggtgtac     420

accctgcccc catcccggga ggagatgacc aagaaccagg tcaacctgac ctgcaacgtc     480

accggcttct atcccagcga catcgccgtg gagtgggaga gcaatgggca gccggagaac     540

aactacaaga ccacgcctcc cgtgctggac tccgacggct ccttcttcct ctatagcaag     600

ctcaccgtgg acaagagcag gtggcagcag gggaacgtct tctcatgctc cgtgatgcat     660

gaggctctgc acaaccacta cacgcagaag agcctctccc tgtccccggg taaatga       717
```

```
<210> SEQ ID NO 55
<211> LENGTH: 238
<212> TYPE: PRT
<213> ORGANISM: Artificial Sequence
<220> FEATURE:
<223> OTHER INFORMATION: Synthetic Construct

<400> SEQUENCE: 55

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Asn Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Asn Leu Thr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

-continued

<210> SEQ ID NO 56
<211> LENGTH: 717
<212> TYPE: DNA
<213> ORGANISM: Artificial Sequence
<220> FEATURE:
<223> OTHER INFORMATION: Synthetic Construct

<400> SEQUENCE: 56
atgaaagctg tggtgctggc cgtggctctg gtcttcctga cagggagcca ggctcggcat 60
catcatcacc atcacggcgg gggaccgtca gtcttcctct tcccccccaaa acccaaggac 120 accctcatga tctcccggac ccctgaggtc acatgcgtgg tggtggacgt gagccacgaa 180
gaccctgagg tcaagttcaa ctggtacgtg gacggcgtgg aggtgcataa tgccaagaca 240
aagccgcggg aggagcagta caacagcacg taccgtgtgg tcagcgtcct caccgtcctg 300
caccaggact ggctgaatgg caaggagtac aagtgcaagg tctccaacaa agccctccca 360
gcccccatcg agaaaaccat ctccaaagcc aaagggcagc cccgagaacc acaggtgtac 420
accctgcccc catcccggga ggagatgacc aagaaccagg tcaacctgac ctgcctggtc 480
aaaggcttct atcccagcga catcgccgtg gagtgggaga gcaatgggca gccggagaac 540
aactacaaga ccacgcctcc cgtgctggac tccgacggct ccttcaacct caccagcaag 600
ctcaccgtgg acaagagcag gtggcagcag gggaacgtct tctcatgctc cgtgatgcat 660
gaggctctgc acaaccacta cacgcagaag agcctctccc tgtccccggg taaatga 717

<210> SEQ ID NO 57
<211> LENGTH: 238
<212> TYPE: PRT
<213> ORGANISM: Artificial Sequence
<220> FEATURE:
<223> OTHER INFORMATION: Synthetic Construct

<400> SEQUENCE: 57

Met Lys Ala Val Val Leu Ala Val Ala Leu Val Phe Leu Thr Gly Ser
1 5 10 15

Gln Ala Arg His His His His His His Gly Gly Gly Pro Ser Val Phe
20 25 30

Leu Phe Pro Pro Lys Pro Lys Asp Thr Leu Met Ile Ser Arg Thr Pro
35 40 45

Glu Val Thr Cys Val Val Val Asp Val Ser His Glu Asp Pro Glu Val
50 55 60

Lys Phe Asn Trp Tyr Val Asp Gly Val Glu Val His Asn Ala Lys Thr
65 70 75 80

Lys Pro Arg Glu Glu Gln Tyr Asn Ser Thr Tyr Arg Val Val Ser Val
85 90 95

Leu Thr Val Leu His Gln Asp Trp Leu Asn Gly Lys Glu Tyr Lys Cys
100 105 110

Lys Val Ser Asn Lys Ala Leu Pro Ala Pro Ile Glu Lys Thr Ile Ser
115 120 125

Lys Ala Lys Gly Gln Pro Arg Glu Pro Gln Val Tyr Thr Leu Pro Pro
130 135 140

Ser Arg Glu Glu Met Thr Lys Asn Gln Val Asn Leu Thr Cys Leu Val
145 150 155 160

Lys Gly Phe Tyr Pro Ser Asp Ile Ala Val Glu Trp Glu Ser Asn Gly
165 170 175

Gln Pro Glu Asn Asn Tyr Lys Thr Thr Pro Pro Val Leu Asp Ser Asp
180 185 190

```
Gly Ser Phe Phe Leu Asn Ser Thr Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235

<210> SEQ ID NO 58
<211> LENGTH: 717
<212> TYPE: DNA
<213> ORGANISM: Artificial Sequence
<220> FEATURE:
<223> OTHER INFORMATION: Synthetic Construct

<400> SEQUENCE: 58

atgaaagctg tggtgctggc cgtggctctg gtcttcctga cagggagcca ggctcggcat      60

catcatcacc atcacggcgg gggaccgtca gtcttcctct tccccccaaa acccaaggac     120

accctcatga tctcccggac ccctgaggtc acatgcgtgg tggtggacgt gagccacgaa     180

gaccctgagg tcaagttcaa ctggtacgtg gacggcgtgg aggtgcataa tgccaagaca     240

aagccgcggg aggagcagta caacagcacg taccgtgtgg tcagcgtcct caccgtcctg     300

caccaggact ggctgaatgg caaggagtac aagtgcaagg tctccaacaa agccctccca     360

gcccccatcg agaaaaccat ctccaaagcc aaagggcagc cccgagaacc acaggtgtac     420

accctgcccc catcccggga ggagatgacc aagaaccagg tcaacctgac ctgcctggtc     480

aaaggcttct atcccagcga catcgccgtg gagtgggaga gcaatgggca gccggagaac     540

aactacaaga ccacgcctcc cgtgctggac tccgacggct ccttcttcct caacagcacc     600

ctcaccgtgg acaagagcag gtggcagcag gggaacgtct tctcatgctc cgtgatgcat     660

gaggctctgc acaaccacta cacgcagaag agcctctccc tgtccccggg taaatga       717

<210> SEQ ID NO 59
<211> LENGTH: 238
<212> TYPE: PRT
<213> ORGANISM: Artificial Sequence
<220> FEATURE:
<223> OTHER INFORMATION: Synthetic Construct

<400> SEQUENCE: 59

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Asn Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
```

```
    130                 135                 140

Ser Arg Glu Glu Met Thr Lys Asn Gln Val Asn Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Asn Ser Thr Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235


<210> SEQ ID NO 60
<211> LENGTH: 717
<212> TYPE: DNA
<213> ORGANISM: Artificial Sequence
<220> FEATURE:
<223> OTHER INFORMATION: Synthetic Construct

<400> SEQUENCE: 60

atgaaagctg tggtgctggc cgtggctctg gtcttcctga cagggagcca ggctcggcat      60

catcatcacc atcacggcgg gggaccgtca gtcttcctct tccccccaaa acccaaggac     120

accctcatga tctcccggac ccctaacgtc acatgcgtgg tggtggacgt gagccacgaa     180

gaccctgagg tcaagttcaa ctggtacgtg gacggcgtgg aggtgcataa tgccaagaca     240

aagccgcggg aggagcagta caacagcacg taccgtgtgg tcagcgtcct caccgtcctg     300

caccaggact ggctgaatgg caaggagtac aagtgcaagg tctccaacaa agccctccca     360

gcccccatcg agaaaaccat ctccaaagcc aaagggcagc cccgagaacc acaggtgtac     420

accctgcccc catcccggga ggagatgacc aagaaccagg tcaacctgac ctgcctggtc     480

aaaggcttct atcccagcga catcgccgtg gagtgggaga gcaatgggca gccggagaac     540

aactacaaga ccacgcctcc cgtgctggac tccgacggct ccttcttcct caacagcacc     600

ctcaccgtgg acaagagcag gtggcagcag gggaacgtct tctcatgctc cgtgatgcat     660

gaggctctgc acaaccacta cacgcagaag agcctctccc tgtccccggg taaatga       717


<210> SEQ ID NO 61
<211> LENGTH: 238
<212> TYPE: PRT
<213> ORGANISM: Artificial Sequence
<220> FEATURE:
<223> OTHER INFORMATION: Synthetic Construct

<400> SEQUENCE: 61

Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Asn Cys Thr Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80
```

```
Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Asn Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Asn Ser Thr Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

<210> SEQ ID NO 62
<211> LENGTH: 717
<212> TYPE: DNA
<213> ORGANISM: Artificial Sequence
<220> FEATURE:
<223> OTHER INFORMATION: Synthetic Construct

<400> SEQUENCE: 62

```
atgaaagctg tggtgctggc cgtggctctg gtcttcctga cagggagcca ggctcggcat      60

catcatcacc atcacggcgg gggaccgtca gtcttcctct tccccccaaa acccaaggac     120

accctcatga tctcccggac ccctgaggtc aactgcaccg tggtggacgt gagccacgaa     180

gaccctgagg tcaagttcaa ctggtacgtg gacggcgtgg aggtgcataa tgccaagaca     240

aagccgcggg aggagcagta caacagcacg taccgtgtgg tcagcgtcct caccgtcctg     300

caccaggact ggctgaatgg caaggagtac aagtgcaagg tctccaacaa agccctccca     360

gcccccatcg agaaaaccat ctccaaagcc aaagggcagc cccgagaacc acaggtgtac     420

accctgcccc catcccggga ggagatgacc aagaaccagg tcaacctgac ctgcctggtc     480

aaaggcttct atcccagcga catcgccgtg gagtgggaga gcaatgggca gccggagaac     540

aactacaaga ccacgcctcc cgtgctggac tccgacggct ccttcttcct caacagcacc     600

ctcaccgtgg acaagagcag gtggcagcag gggaacgtct tctcatgctc cgtgatgcat     660

gaggctctgc acaaccacta cacgcagaag agcctctccc tgtccccggg taaatga        717
```

<210> SEQ ID NO 63
<211> LENGTH: 238
<212> TYPE: PRT
<213> ORGANISM: Artificial Sequence
<220> FEATURE:
<223> OTHER INFORMATION: Synthetic Construct

<400> SEQUENCE: 63

```
Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30
```

```
Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Thr Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Asn Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Asn Ser Thr Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

<210> SEQ ID NO 64
<211> LENGTH: 717
<212> TYPE: DNA
<213> ORGANISM: Artificial Sequence
<220> FEATURE:
<223> OTHER INFORMATION: Synthetic Construct

<400> SEQUENCE: 64

```
atgaaagctg tggtgctggc cgtggctctg gtcttcctga cagggagcca ggctcggcat      60

catcatcacc atcacggcgg gggaccgtca gtcttcctct tccccccaaa acccaaggac     120

accctcatga tctcccggac ccctgaggtc acatgcgtgg tggtggacgt gagccacgaa     180

gaccctgagg tcaagttcaa ctggtacgtg gacggcgtgg aggtgcataa tgccaccaca     240

aagccgcggg aggagcagta caacagcacg taccgtgtgg tcagcgtcct caccgtcctg     300

caccaggact ggctgaatgg caaggagtac aagtgcaagg tctccaacaa agccctccca     360

gcccccatcg agaaaaccat ctccaaagcc aaagggcagc cccgagaacc acaggtgtac     420

accctgcccc catcccggga ggagatgacc aagaaccagg tcaacctgac ctgcctggtc     480

aaaggcttct atcccagcga catcgccgtg gagtgggaga gcaatgggca gccggagaac     540

aactacaaga ccacgcctcc cgtgctggac tccgacggct ccttcttcct caacagcacc     600

ctcaccgtgg acaagagcag gtggcagcag gggaacgtct tctcatgctc cgtgatgcat     660

gaggctctgc acaaccacta cacgcagaag agcctctccc tgtccccggg taaatga        717
```

<210> SEQ ID NO 65
<211> LENGTH: 238
<212> TYPE: PRT
<213> ORGANISM: Artificial Sequence
<220> FEATURE:
<223> OTHER INFORMATION: Synthetic Construct

<400> SEQUENCE: 65

```
Met Lys Ala Val Val Leu Ala Val Ala Leu Val Phe Leu Thr Gly Ser
1               5                   10                  15

Gln Ala Arg His His His His His His Gly Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Asn
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Asn Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Asn Ser Thr Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

<210> SEQ ID NO 66
<211> LENGTH: 717
<212> TYPE: DNA
<213> ORGANISM: Artificial Sequence
<220> FEATURE:
<223> OTHER INFORMATION: Synthetic Construct

<400> SEQUENCE: 66

```
atgaaagctg tggtgctggc cgtggctctg gtcttcctga cagggagcca ggctcggcat      60

catcatcacc atcacggcgg gggaccgtca gtcttcctct tccccccaaa acccaaggac     120

accctcatga tctcccggac ccctgaggtc acatgcgtgg tggtggacgt gagccacgaa     180

gaccctgagg tcaagttcaa ctggtacgtg gacggcgtgg aggtgcataa tgccaagaca     240

aagccgcggg aggagcagta caacagcacg taccgtgtgg tcagcaacct caccgtcctg     300

caccaggact ggctgaatgg caaggagtac aagtgcaagg tctccaacaa agccctccca     360

gcccccatcg agaaaaccat ctccaaagcc aaagggcagc cccgagaacc acaggtgtac     420

accctgcccc catcccggga ggagatgacc aagaaccagg tcaacctgac ctgcctggtc     480

aaaggcttct atcccagcga catcgccgtg gagtgggaga gcaatgggca gccggagaac     540

aactacaaga ccacgcctcc cgtgctggac tccgacggct ccttcttcct caacagcacc     600
```

```
ctcaccgtgg acaagagcag gtggcagcag gggaacgtct tctcatgctc cgtgatgcat    660

gaggctctgc acaaccacta cacgcagaag agcctctccc tgtccccggg taaatga       717


<210> SEQ ID NO 67
<211> LENGTH: 463
<212> TYPE: PRT
<213> ORGANISM: Artificial Sequence
<220> FEATURE:
<223> OTHER INFORMATION: Synthetic Construct

<400> SEQUENCE: 67

Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Asp Met Tyr Trp Val Arg Gln Thr Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Glu Lys Ser Ser Thr Ser Ala Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
```

```
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460


<210> SEQ ID NO 68
<211> LENGTH: 1404
<212> TYPE: DNA
<213> ORGANISM: Artificial Sequence
<220> FEATURE:
<223> OTHER INFORMATION: Synthetic Construct

<400> SEQUENCE: 68

atgggatgga gctgtatcat cctcttcttg gtagcaacag ctacaggcgc gcactccgag     60

gtgcagctgg tggagtctgg gggaggcttg gtacagcctg gggggtccct gagactctcc    120

tgtgcagcct ctggattcac cttcagtaac tacgacatgt actgggtccg ccaaactaca    180

ggaaaaggtc tggagtgggt ctcagctatt ggtactgctg gtgacacata ctatccaggc    240

tccgtgaagg gccgattcac catctccaga gaaaatgcca agaactcctt gtatcttcaa    300

atgaacagcc tgagagccgg ggacacggct gtgtattact gtgcaagaga gaagtctagc    360

acctcggcct ttgactactg gggccaggga accctggtca cagtctcctc agcgtcgacc    420

aagggcccat cggtcttccc cctggcaccc tcctccaaga gcacctctgg gggcacagcg    480

gccctgggct gcctggtcaa ggactacttc cccgaaccgg tgacggtgtc gtggaactca    540

ggcgccctga ccagcggcgt gcacaccttc ccggctgtcc tacagtcctc aggactctac    600

tccctcagca gcgtggtgac cgtgccctcc agcagcttgg gcacccagac ctacatctgc    660

aacgtgaatc acaagcccag caacaccaag gtggacaaga aagttgagcc caaatcttgt    720

gacaaaactc acacatgccc accgtgccca gcacctgaac tcctgggggg accgtcagtc    780

ttcctcttcc ccccaaaacc caaggacacc ctcatgatct cccggacccc tgaggtcaca    840

tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggagga gatgaccaag   1140

aaccaggtca gcctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcta tagcaagctc accgtggaca agagcaggtg gcagcagggg   1320

aacgtcttct catgctccgt gatgcatgag gctctgcaca accactacac gcagaagagc   1380
```

-continued

```
ctctccctgt ccccgggtaa atga                                   1404


<210> SEQ ID NO 69
<211> LENGTH: 231
<212> TYPE: PRT
<213> ORGANISM: Artificial Sequence
<220> FEATURE:
<223> OTHER INFORMATION: Synthetic Construct

<400> SEQUENCE: 69

Met Gly Trp Ser Cys Ile Ile Leu Phe Leu Val Ala Thr Ala Thr Gly
1               5                   10                  15

Ala His Ser Asp Ile Gln Met Thr Gln Ser Pro Ser Ser Leu Ser Val
            20                  25                  30

Ser Val Gly Asp Arg Val Thr Ile Thr Cys Gln Ala Gly Gln Asp Ile
        35                  40                  45

Arg Asn Tyr Leu Asn Trp Tyr Gln Gln Lys Pro Gly Lys Ala Pro Lys
    50                  55                  60

Leu Leu Ile Tyr Asp Ala Ser Asn Leu Glu Thr Gly Val Pro Ser Arg
65                  70                  75                  80

Phe Ser Gly Ser Gly Ser Gly Thr Ala Phe Thr Phe Thr Ile Ser Ser
                85                  90                  95

Leu Gln Pro Glu Asp Ile Ala Thr Tyr Tyr Cys Gln Gln Tyr Asp Asn
            100                 105                 110

Leu Thr Phe Gly Gln Gly Thr Lys Leu Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230


<210> SEQ ID NO 70
<211> LENGTH: 910
<212> TYPE: DNA
<213> ORGANISM: Artificial Sequence
<220> FEATURE:
<223> OTHER INFORMATION: Synthetic Construct

<400> SEQUENCE: 70

atgggatgga gctgtatcat cctcttcttg gtagcaacag ctacaggcgc gcactccgac      60

atccagatga cccagtctcc atcctccctg tctgtatctg tgggagacag agtcaccatc     120

acttgccagg cgggtcagga cattcgcaac tatttaaatt ggtatcagca gaaaccaggg     180

aaagccccta aactcctgat ctacgatgca tccaatttgg aaacaggggt cccatcaagg     240

ttcagtggaa gtggatctgg gacagctttt actttcacca tcagcagcct gcagcctgaa     300

gatattgcaa catattactg tcaacagtat gataatctca cttttggcca ggggaccaaa     360
```

```
ctggaaatca aacgtgagta gaataactct agaggaatag ggaagctagg aagaaactca    420

aaacatcaag attttaaata cgcttcttgg tctccttgct ataattatct gggataagca    480

tgctgttttc tgtctgtccc taacatgccc tgtgattatc cgcaaacaac acacccaagg    540

gcagaacttt gttacttaaa caccatcctg tttgcttctt tcctcaggaa ctgtggctgc    600

accatctgtc ttcatcttcc cgccatctga tgagcagttg aaatctggaa ctgcctctgt    660

tgtgtgcctg ctgaataact tctatcccag agaggccaaa gtacagtgga aggtggataa    720

cgccctccaa tcgggtaact cccaggagag tgtcacagag caggacagca aggacagcac    780

ctacagcctc agcagcaccc tgacgctgag caaagcagac tacgagaaac acaaagtcta    840

cgcctgcgaa gtcacccatc agggcctgag ctcgcccgtc acaaagagct tcaacagggg    900

agagtgttag                                                           910


<210> SEQ ID NO 71
<211> LENGTH: 467
<212> TYPE: PRT
<213> ORGANISM: Artificial Sequence
<220> FEATURE:
<223> OTHER INFORMATION: Synthetic Construct

<400> SEQUENCE: 71

Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Asp Met Tyr Trp Val Arg Gln Thr Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Glu Lys Ser Ser Thr Ser Ala Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Gly Gly Gly Gly Ser Gly Gly Gly Gly Ser Gly
                245                 250                 255

Gly Pro Ser Val Phe Leu Phe Pro Pro Lys Pro Lys Asp Thr Leu Met
```

```
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Asn
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Asn Ser Thr Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

<210> SEQ ID NO 72
<211> LENGTH: 1404
<212> TYPE: DNA
<213> ORGANISM: Artificial Sequence
<220> FEATURE:
<223> OTHER INFORMATION: Synthetic Construct

<400> SEQUENCE: 72

```
atgggatgga gctgtatcat cctcttcttg gtagcaacag ctacaggcgc gcactccgag      60

gtgcagctgg tggagtctgg gggaggcttg gtacagcctg gggggtccct gagactctcc     120

tgtgcagcct ctggattcac cttcagtaac tacgacatgt actgggtccg ccaaactaca     180

ggaaaaggtc tggagtgggt ctcagctatt ggtactgctg gtgacacata ctatccaggc     240

tccgtgaagg gccgattcac catctccaga gaaaatgcca agaactcctt gtatcttcaa     300

atgaacagcc tgagagccgg ggacacggct gtgtattact gtgcaagaga gaagtctagc     360

acctcggcct ttgactactg gggccaggga accctggtca ccgtctcctc agcctccacc     420

aagggcccga gcgtgtttcc gctggcaccg agcagcaaaa gcaccagcgg tggcacagca     480

gcactgggtt gtctggtgaa agattatttt ccggaaccgg ttacagttag ctggaatagc     540

ggtgccctga ccagcggtgt tcataccttt ccggcagttc tgcagagcag cggtctgtat     600

agcctgtcta gcgttgttac cgttccgagc agcagcctgg gcacccagac ctatatttgc     660

aatgtgaatc ataaaccgag caataccaaa gtggataaaa aagtggagcc taagagctgt     720

gacaaaactc acacaggtgg aggcgggtcc ggtggaggcg ggtccggggg accgtcagtc     780

ttcctcttcc ccccaaaacc caaggacacc ctcatgatct cccggacccc tgaggtcaca     840
```

-continued

```
tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggagga gatgaccaag   1140

aaccaggtca acctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcaa cagcaccctc accgtggaca agagcaggtg gcagcagggg   1320

aacgtcttct catgctccgt gatgcatgag gctctgcaca accactacac gcagaagagc   1380

ctctccctgt ccccgggtaa atga                                          1404


<210> SEQ ID NO 73
<211> LENGTH: 467
<212> TYPE: PRT
<213> ORGANISM: Artificial Sequence
<220> FEATURE:
<223> OTHER INFORMATION: Synthetic Construct

<400> SEQUENCE: 73

Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Asp Met Tyr Trp Val Arg Gln Thr Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Glu Lys Ser Ser Thr Ser Ala Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Gly Gly Gly Gly Ser Gly Gly Gly Gly Ser Gly
                245                 250                 255

Gly Pro Ser Val Phe Leu Phe Pro Pro Lys Pro Lys Asp Thr Leu Met
```

```
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Asn
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Asn Ser Thr Leu Thr Val
            420                 425                 430

Asp Lys Ser Arg Trp Gln Gln Gly Asn Val Phe Ser Cys Ser Val Leu
        435                 440                 445

His Glu Ala Leu His Ser His Tyr Thr Gln Lys Ser Leu Ser Leu Ser
    450                 455                 460

Pro Gly Lys
465


<210> SEQ ID NO 74
<211> LENGTH: 1404
<212> TYPE: DNA
<213> ORGANISM: Artificial Sequence
<220> FEATURE:
<223> OTHER INFORMATION: Synthetic Construct

<400> SEQUENCE: 74

atgggatgga gctgtatcat cctcttcttg gtagcaacag ctacaggcgc gcactccgag      60

gtgcagctgg tggagtctgg gggaggcttg gtacagcctg gggggtccct gagactctcc     120

tgtgcagcct ctggattcac cttcagtaac tacgacatgt actgggtccg ccaaactaca     180

ggaaaaggtc tggagtgggt ctcagctatt ggtactgctg gtgacacata ctatccaggc     240

tccgtgaagg gccgattcac catctccaga gaaaatgcca agaactcctt gtatcttcaa     300

atgaacagcc tgagagccgg ggacacggct gtgtattact gtgcaagaga gaagtctagc     360

acctcggcct ttgactactg gggccaggga accctggtca ccgtctcctc agcctccacc     420

aagggcccga gcgtgtttcc gctggcaccg agcagcaaaa gcaccagcgg tggcacagca     480

gcactgggtt gtctggtgaa agattatttt ccggaaccgg ttacagttag ctggaatagc     540

ggtgccctga ccagcggtgt tcataccttt ccggcagttc tgcagagcag cggtctgtat     600

agcctgtcta gcgttgttac cgttccgagc agcagcctgg gcacccagac ctatatttgc     660

aatgtgaatc ataaaccgag caataccaaa gtggataaaa aagtggagcc taagagctgt     720

gacaaaactc acacaggtgg aggcgggtcc ggtggaggcg ggtccggggg accgtcagtc     780

ttcctcttcc ccccaaaacc caaggacacc ctcatgatct cccggacccc tgaggtcaca     840
```

-continued

```
tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggagga gatgaccaag   1140

aaccaggtca acctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcaa cagcaccctc accgtggaca agagcaggtg gcagcagggg   1320

aacgtcttct catgctccgt gctgcatgag gctctgcaca gccactacac gcagaagagc   1380

ctctccctgt ccccgggtaa atga                                          1404


<210> SEQ ID NO 75
<211> LENGTH: 467
<212> TYPE: PRT
<213> ORGANISM: Artificial Sequence
<220> FEATURE:
<223> OTHER INFORMATION: Synthetic Construct

<400> SEQUENCE: 75

Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Asp Met Tyr Trp Val Arg Gln Thr Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Glu Lys Ser Ser Thr Ser Ala Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Gly Gly Gly Gly Ser Gly Gly Gly Gly Ser Gly
                245                 250                 255

Gly Pro Ser Val Phe Leu Phe Pro Pro Lys Pro Lys Asp Thr Leu Met
```

-continued

```
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu Ala Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Asn
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Asn Ser Thr Leu Thr Val
            420                 425                 430

Asp Lys Ser Arg Trp Gln Gln Gly Asn Val Phe Ser Cys Ser Val Met
        435                 440                 445

His Glu Ala Leu Ala Asn His Tyr Thr Gln Lys Ser Leu Ser Leu Ser
    450                 455                 460

Pro Gly Lys
465


<210> SEQ ID NO 76
<211> LENGTH: 1404
<212> TYPE: DNA
<213> ORGANISM: Artificial Sequence
<220> FEATURE:
<223> OTHER INFORMATION: Synthetic Construct

<400> SEQUENCE: 76

atgggatgga gctgtatcat cctcttcttg gtagcaacag ctacaggcgc gcactccgag      60

gtgcagctgg tggagtctgg gggaggcttg gtacagcctg gggggtccct gagactctcc     120

tgtgcagcct ctggattcac cttcagtaac tacgacatgt actgggtccg ccaaactaca     180

ggaaaaggtc tggagtgggt ctcagctatt ggtactgctg gtgacacata ctatccaggc     240

tccgtgaagg gccgattcac catctccaga gaaaatgcca agaactcctt gtatcttcaa     300

atgaacagcc tgagagccgg ggacacggct gtgtattact gtgcaagaga gaagtctagc     360

acctcggcct ttgactactg gggccaggga accctggtca ccgtctcctc agcctccacc     420

aagggcccga gcgtgtttcc gctggcaccg agcagcaaaa gcaccagcgg tggcacagca     480

gcactgggtt gtctggtgaa agattatttt ccggaaccgg ttacagttag ctggaatagc     540

ggtgccctga ccagcggtgt tcataccttt ccggcagttc tgcagagcag cggtctgtat     600

agcctgtcta gcgttgttac cgttccgagc agcagcctgg gcacccagac ctatatttgc     660

aatgtgaatc ataaaccgag caataccaaa gtggataaaa aagtggagcc taagagctgt     720

gacaaaactc acacaggtgg aggcgggtcc ggtggaggcg ggtccggggg accgtcagtc     780

ttcctcttcc ccccaaaacc caaggacacc ctcatgatct cccggacccc tgaggtcaca     840
```

-continued

```
tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctggcc caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggagga gatgaccaag   1140

aaccaggtca acctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcaa cagcaccctc accgtggaca agagcaggtg gcagcagggg   1320

aacgtcttct catgctccgt gatgcatgag gctctggcca accactacac gcagaagagc   1380

ctctccctgt ccccgggtaa atga                                           1404


<210> SEQ ID NO 77
<211> LENGTH: 677
<212> TYPE: PRT
<213> ORGANISM: Artificial Sequence
<220> FEATURE:
<223> OTHER INFORMATION: Synthetic Construct

<400> SEQUENCE: 77

Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Asp Met Tyr Trp Val Arg Gln Thr Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Glu Lys Ser Ser Thr Ser Ala Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Gly Gly Gly Gly Ser Gly Gly Gly Gly Ser Gly
                245                 250                 255

Gly Pro Ser Val Phe Leu Phe Pro Pro Lys Pro Lys Asp Thr Leu Met
```

-continued

```
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Asn
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Asn Ser Thr Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Pro Ser Val Phe Leu Phe Pro Pro Lys Pro Lys Asp Thr
465                 470                 475                 480

Leu Met Ile Ser Arg Thr Pro Glu Val Thr Cys Val Val Val Asp Val
                485                 490                 495

Ser His Glu Asp Pro Glu Val Lys Phe Asn Trp Tyr Val Asp Gly Val
            500                 505                 510

Glu Val His Asn Ala Lys Thr Lys Pro Arg Glu Glu Gln Tyr Asn Ser
        515                 520                 525

Thr Tyr Arg Val Val Ser Val Leu Thr Val Leu His Gln Asp Trp Leu
    530                 535                 540

Asn Gly Lys Glu Tyr Lys Cys Lys Val Ser Asn Lys Ala Leu Pro Ala
545                 550                 555                 560

Pro Ile Glu Lys Thr Ile Ser Lys Ala Lys Gly Gln Pro Arg Glu Pro
                565                 570                 575

Gln Val Tyr Thr Leu Pro Pro Ser Arg Glu Glu Met Thr Lys Asn Gln
            580                 585                 590

Val Asn Leu Thr Cys Leu Val Lys Gly Phe Tyr Pro Ser Asp Ile Ala
        595                 600                 605

Val Glu Trp Glu Ser Asn Gly Gln Pro Glu Asn Asn Tyr Lys Thr Thr
    610                 615                 620

Pro Pro Val Leu Asp Ser Asp Gly Ser Phe Phe Leu Asn Ser Thr Leu
625                 630                 635                 640

Thr Val Asp Lys Ser Arg Trp Gln Gln Gly Asn Val Phe Ser Cys Ser
                645                 650                 655

Val Met His Glu Ala Leu His Asn His Tyr Thr Gln Lys Ser Leu Ser
            660                 665                 670

Leu Ser Pro Gly Lys
        675
```

<210> SEQ ID NO 78
<211> LENGTH: 2037
<212> TYPE: DNA
<213> ORGANISM: Artificial Sequence
<220> FEATURE:
<223> OTHER INFORMATION: Synthetic Construct

<400> SEQUENCE: 78
atgggatgga gctgtatcat cctcttcttg gtagcaacag ctacaggcgc gcactccgag 60
gtgcagctgg tggagtctgg gggaggcttg gtacagcctg gggggtccct gagactctcc 120
tgtgcagcct ctggattcac cttcagtaac tacgacatgt actgggtccg ccaaactaca 180
ggaaaaggtc tggagtgggt ctcagctatt ggtactgctg gtgacacata ctatccaggc 240
tccgtgaagg gccgattcac catctccaga gaaaatgcca agaactcctt gtatcttcaa 300
atgaacagcc tgagagccgg ggacacggct gtgtattact gtgcaagaga gaagtctagc 360
acctcggcct ttgactactg gggccaggga accctggtca ccgtctcctc agcctccacc 420
aagggcccga gcgtgtttcc gctggcaccg agcagcaaaa gcaccagcgg tggcacagca 480
gcactgggtt gtctggtgaa agattatttt ccggaaccgg ttacagttag ctggaatagc 540
ggtgccctga ccagcggtgt tcataccttt ccggcagttc tgcagagcag cggtctgtat 600
agcctgtcta gcgttgttac cgttccgagc agcagcctgg gcacccagac ctatatttgc 660
aatgtgaatc ataaaccgag caataccaaa gtggataaaa aagtggagcc taagagctgt 720
gacaaaactc acacaggtgg aggcgggtcc ggtggaggcg ggtccggggg accgtcagtc 780
ttcctcttcc ccccaaaacc caaggacacc ctcatgatct cccggacccc tgaggtcaca 840
tgcgtggtgg tggacgtgag ccacgaagac cctgaggtca agttcaactg gtacgtggac 900
ggcgtggagg tgcataatgc caagacaaag ccgcgggagg agcagtacaa cagcacgtac 960
cgtgtggtca gcgtcctcac cgtcctgcac caggactggc tgaatggcaa ggagtacaag 1020
tgcaaggtct ccaacaaagc cctcccagcc cccatcgaga aaaccatctc caaagccaaa 1080
gggcagcccc gagaaccaca ggtgtacacc ctgcccccat cccgggagga gatgaccaag 1140
aaccaggtca acctgacctg cctggtcaaa ggcttctatc ccagcgacat cgccgtggag 1200
tgggagagca atgggcagcc ggagaacaac tacaagacca cgcctcccgt gctggactcc 1260
gacggctcct tcttcctcaa cagcaccctc accgtggaca agagcaggtg gcagcagggg 1320
aacgtcttct catgctccgt gatgcatgag gctctgcaca accactacac gcagaagagc 1380
ctctccctgt ccccgggtgg gggaccgtca gtcttcctct tccccccaaa acccaaggac 1440
accctcatga tctcccggac ccctgaggtc acatgcgtgg tggtggacgt gagccacgaa 1500
gaccctgagg tcaagttcaa ctggtacgtg gacggcgtgg aggtgcataa tgccaagaca 1560
aagccgcggg aggagcagta caacagcacg taccgtgtgg tcagcgtcct caccgtcctg 1620
caccaggact ggctgaatgg caaggagtac aagtgcaagg tctccaacaa agccctccca 1680
gcccccatcg agaaaaccat ctccaaagcc aaagggcagc cccgagaacc acaggtgtac 1740
accctgcccc catcccggga ggagatgacc aagaaccagg tcaacctgac ctgcctggtc 1800
aaaggcttct atcccagcga catcgccgtg gagtgggaga gcaatgggca gccggagaac 1860
aactacaaga ccacgcctcc cgtgctggac tccgacggct ccttcttcct caacagcacc 1920
ctcaccgtgg acaagagcag gtggcagcag gggaacgtct tctcatgctc cgtgatgcat 1980
gaggctctgc acaaccacta cacgcagaag agcctctccc tgtccccggg taaatga 2037

<210> SEQ ID NO 79
<211> LENGTH: 682
<212> TYPE: PRT
<213> ORGANISM: Artificial Sequence
<220> FEATURE:
<223> OTHER INFORMATION: Synthetic Construct

<400> SEQUENCE: 79

```
Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Asp Met Tyr Trp Val Arg Gln Thr Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Glu Lys Ser Ser Thr Ser Ala Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Gly Gly Gly Gly Ser Gly Gly Gly Gly Ser Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365
```

```
Tyr Thr Leu Pro Pro Ser Arg Glu Glu Met Thr Lys Asn Gln Val Asn
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Asn Ser Thr Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Gly Gly Ser Gly Gly Pro Ser Val Phe Leu Phe Pro Pro
465                 470                 475                 480

Lys Pro Lys Asp Thr Leu Met Ile Ser Arg Thr Pro Glu Val Thr Cys
                485                 490                 495

Val Val Val Asp Val Ser His Glu Asp Pro Glu Val Lys Phe Asn Trp
            500                 505                 510

Tyr Val Asp Gly Val Glu Val His Asn Ala Lys Thr Lys Pro Arg Glu
        515                 520                 525

Glu Gln Tyr Asn Ser Thr Tyr Arg Val Val Ser Val Leu Thr Val Leu
    530                 535                 540

His Gln Asp Trp Leu Asn Gly Lys Glu Tyr Lys Cys Lys Val Ser Asn
545                 550                 555                 560

Lys Ala Leu Pro Ala Pro Ile Glu Lys Thr Ile Ser Lys Ala Lys Gly
                565                 570                 575

Gln Pro Arg Glu Pro Gln Val Tyr Thr Leu Pro Pro Ser Arg Glu Glu
            580                 585                 590

Met Thr Lys Asn Gln Val Asn Leu Thr Cys Leu Val Lys Gly Phe Tyr
        595                 600                 605

Pro Ser Asp Ile Ala Val Glu Trp Glu Ser Asn Gly Gln Pro Glu Asn
    610                 615                 620

Asn Tyr Lys Thr Thr Pro Pro Val Leu Asp Ser Asp Gly Ser Phe Phe
625                 630                 635                 640

Leu Asn Ser Thr Leu Thr Val Asp Lys Ser Arg Trp Gln Gln Gly Asn
                645                 650                 655

Val Phe Ser Cys Ser Val Met His Glu Ala Leu His Asn His Tyr Thr
            660                 665                 670

Gln Lys Ser Leu Ser Leu Ser Pro Gly Lys
        675                 680
```

<210> SEQ ID NO 80
<211> LENGTH: 2049
<212> TYPE: DNA
<213> ORGANISM: Artificial Sequence
<220> FEATURE:
<223> OTHER INFORMATION: Synthetic Construct

<400> SEQUENCE: 80

```
atgggatgga gctgtatcat cctcttcttg gtagcaacag ctacaggcgc gcactccgag     60

gtgcagctgg tggagtctgg gggaggcttg gtacagcctg gggggtccct gagactctcc    120

tgtgcagcct ctggattcac cttcagtaac tacgacatgt actgggtccg ccaaactaca    180

ggaaaaggtc tggagtgggt ctcagctatt ggtactgctg gtgacacata ctatccaggc    240

tccgtgaagg gccgattcac catctccaga gaaaatgcca agaactcctt gtatcttcaa    300
```

-continued atgaacagcc tgagagccgg ggacacggct gtgtattact gtgcaagaga gaagtctagc 360
acctcggcct ttgactactg gggccaggga accctggtca ccgtctcctc agcctccacc 420
aagggcccga gcgtgtttcc gctggcaccg agcagcaaaa gcaccagcgg tggcacagca 480
gcactgggtt gtctggtgaa agattatttt ccggaaccgg ttacagttag ctggaatagc 540
ggtgccctga ccagcggtgt tcatacctttt ccggcagttc tgcagagcag cggtctgtat 600
agcctgtcta gcgttgttac cgttccgagc agcagcctgg gcacccagac ctatatttgc 660
aatgtgaatc ataaaccgag caataccaaa gtggataaaa aagtggagcc taagagctgt 720
gacaaaactc acacaggtgg aggcgggtcc ggtggaggcg ggtccggggg accgtcagtc 780
ttcctcttcc ccccaaaacc caaggacacc ctcatgatct cccggacccc tgaggtcaca 840
tgcgtggtgg tggacgtgag ccacgaagac cctgaggtca agttcaactg gtacgtggac 900
ggcgtggagg tgcataatgc caagacaaag ccgcgggagg agcagtacaa cagcacgtac 960
cgtgtggtca gcgtcctcac cgtcctgcac caggactggc tgaatggcaa ggagtacaag 1020
tgcaaggtct ccaacaaagc cctcccagcc cccatcgaga aaaccatctc caaagccaaa 1080
gggcagcccc gagaaccaca ggtgtacacc ctgcccccat cccgggagga gatgaccaag 1140
aaccaggtca acctgacctg cctggtcaaa ggcttctatc ccagcgacat cgccgtggag 1200
tgggagagca atgggcagcc ggagaacaac tacaagacca cgcctcccgt gctggactcc 1260
gacggctcct tcttcctcaa cagcaccctc accgtggaca agagcaggtg gcagcagggg 1320
aacgtcttct catgctccgt gatgcatgag gctctgcaca accactacac gcagaagagc 1380
ctctccctgt ccccgggtgg tggcggctcc gggggaccgt cagtcttcct cttcccccca 1440
aaacccaagg acaccctcat gatctcccgg acccctgagg tcacatgcgt ggtggtggac 1500
gtgagccacg aagaccctga ggtcaagttc aactggtacg tggacggcgt ggaggtgcat 1560
aatgccaaga caaagccgcg ggaggagcag tacaacagca cgtaccgtgt ggtcagcgtc 1620
ctcaccgtcc tgcaccagga ctggctgaat ggcaaggagt acaagtgcaa ggtctccaac 1680
aaagccctcc cagcccccat cgagaaaacc atctccaaag ccaaagggca gccccgagaa 1740
ccacaggtgt acaccctgcc cccatcccgg gaggagatga ccaagaacca ggtcaacctg 1800
acctgcctgg tcaaaggctt ctatcccagc gacatcgccg tggagtggga gagcaatggg 1860
cagccggaga acaactacaa gaccacgcct cccgtgctgg actccgacgg ctccttcttc 1920
ctcaacagca ccctcaccgt ggacaagagc aggtggcagc aggggaacgt cttctcatgc 1980
tccgtgatgc atgaggctct gcacaaccac tacacgcaga agagcctctc cctgtccccg 2040
ggtaaatga 2049

<210> SEQ ID NO 81
<211> LENGTH: 687
<212> TYPE: PRT
<213> ORGANISM: Artificial Sequence
<220> FEATURE:
<223> OTHER INFORMATION: Synthetic Construct

<400> SEQUENCE: 81

Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

-continued

Ser Asn Tyr Asp Met Tyr Trp Val Arg Gln Thr Thr Gly Lys Gly Leu
50 55 60

Glu Trp Val Ser Ala Ile Gly Thr Ala Gly Asp Thr Tyr Tyr Pro Gly
65 70 75 80

Ser Val Lys Gly Arg Phe Thr Ile Ser Arg Glu Asn Ala Lys Asn Ser
85 90 95

Leu Tyr Leu Gln Met Asn Ser Leu Arg Ala Gly Asp Thr Ala Val Tyr
100 105 110

Tyr Cys Ala Arg Glu Lys Ser Ser Thr Ser Ala Phe Asp Tyr Trp Gly
115 120 125

Gln Gly Thr Leu Val Thr Val Ser Ser Ala Ser Thr Lys Gly Pro Ser
130 135 140

Val Phe Pro Leu Ala Pro Ser Ser Lys Ser Thr Ser Gly Gly Thr Ala
145 150 155 160

Ala Leu Gly Cys Leu Val Lys Asp Tyr Phe Pro Glu Pro Val Thr Val
165 170 175

Ser Trp Asn Ser Gly Ala Leu Thr Ser Gly Val His Thr Phe Pro Ala
180 185 190

Val Leu Gln Ser Ser Gly Leu Tyr Ser Leu Ser Ser Val Val Thr Val
195 200 205

Pro Ser Ser Ser Leu Gly Thr Gln Thr Tyr Ile Cys Asn Val Asn His
210 215 220

Lys Pro Ser Asn Thr Lys Val Asp Lys Lys Val Glu Pro Lys Ser Cys
225 230 235 240

Asp Lys Thr His Thr Gly Gly Gly Gly Ser Gly Gly Gly Gly Ser Gly
245 250 255

Gly Pro Ser Val Phe Leu Phe Pro Pro Lys Pro Lys Asp Thr Leu Met
260 265 270

Ile Ser Arg Thr Pro Glu Val Thr Cys Val Val Val Asp Val Ser His
275 280 285

Glu Asp Pro Glu Val Lys Phe Asn Trp Tyr Val Asp Gly Val Glu Val
290 295 300

His Asn Ala Lys Thr Lys Pro Arg Glu Glu Gln Tyr Asn Ser Thr Tyr
305 310 315 320

Arg Val Val Ser Val Leu Thr Val Leu His Gln Asp Trp Leu Asn Gly
325 330 335

Lys Glu Tyr Lys Cys Lys Val Ser Asn Lys Ala Leu Pro Ala Pro Ile
340 345 350

Glu Lys Thr Ile Ser Lys Ala Lys Gly Gln Pro Arg Glu Pro Gln Val
355 360 365

Tyr Thr Leu Pro Pro Ser Arg Glu Glu Met Thr Lys Asn Gln Val Asn
370 375 380

Leu Thr Cys Leu Val Lys Gly Phe Tyr Pro Ser Asp Ile Ala Val Glu
385 390 395 400

Trp Glu Ser Asn Gly Gln Pro Glu Asn Asn Tyr Lys Thr Thr Pro Pro
405 410 415

Val Leu Asp Ser Asp Gly Ser Phe Phe Leu Asn Ser Thr Leu Thr Val
420 425 430

Asp Lys Ser Arg Trp Gln Gln Gly Asn Val Phe Ser Cys Ser Val Met
435 440 445

His Glu Ala Leu His Asn His Tyr Thr Gln Lys Ser Leu Ser Leu Ser
450 455 460

```
Pro Gly Gly Gly Gly Ser Gly Gly Gly Gly Ser Gly Gly Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser His Glu Asp Pro Glu
            500                 505                 510

Val Lys Phe Asn Trp Tyr Val Asp Gly Val Glu Val His Asn Ala Lys
        515                 520                 525

Thr Lys Pro Arg Glu Glu Gln Tyr Asn Ser Thr Tyr Arg Val Val Ser
    530                 535                 540

Val Leu Thr Val Leu His Gln Asp Trp Leu Asn Gly Lys Glu Tyr Lys
545                 550                 555                 560

Cys Lys Val Ser Asn Lys Ala Leu Pro Ala Pro Ile Glu Lys Thr Ile
                565                 570                 575

Ser Lys Ala Lys Gly Gln Pro Arg Glu Pro Gln Val Tyr Thr Leu Pro
            580                 585                 590

Pro Ser Arg Glu Glu Met Thr Lys Asn Gln Val Asn Leu Thr Cys Leu
        595                 600                 605

Val Lys Gly Phe Tyr Pro Ser Asp Ile Ala Val Glu Trp Glu Ser Asn
    610                 615                 620

Gly Gln Pro Glu Asn Asn Tyr Lys Thr Thr Pro Pro Val Leu Asp Ser
625                 630                 635                 640

Asp Gly Ser Phe Phe Leu Asn Ser Thr Leu Thr Val Asp Lys Ser Arg
                645                 650                 655

Trp Gln Gln Gly Asn Val Phe Ser Cys Ser Val Met His Glu Ala Leu
            660                 665                 670

His Asn His Tyr Thr Gln Lys Ser Leu Ser Leu Ser Pro Gly Lys
        675                 680                 685
```

<210> SEQ ID NO 82
<211> LENGTH: 2064
<212> TYPE: DNA
<213> ORGANISM: Artificial Sequence
<220> FEATURE:
<223> OTHER INFORMATION: Synthetic Construct

<400> SEQUENCE: 82

```
atgggatgga gctgtatcat cctcttcttg gtagcaacag ctacaggcgc gcactccgag     60

gtgcagctgg tggagtctgg gggaggcttg gtacagcctg gggggtccct gagactctcc    120

tgtgcagcct ctggattcac cttcagtaac tacgacatgt actgggtccg ccaaactaca    180

ggaaaaggtc tggagtgggt ctcagctatt ggtactgctg gtgacacata ctatccaggc    240

tccgtgaagg gccgattcac catctccaga gaaaatgcca agaactcctt gtatcttcaa    300

atgaacagcc tgagagccgg ggacacggct gtgtattact gtgcaagaga gaagtctagc    360

acctcggcct ttgactactg gggccaggga accctggtca ccgtctcctc agcctccacc    420

aagggcccga gcgtgtttcc gctggcaccg agcagcaaaa gcaccagcgg tggcacagca    480

gcactgggtt gtctggtgaa agattatttt ccggaaccgg ttacagttag ctggaatagc    540

ggtgccctga ccagcggtgt tcataccttt ccggcagttc tgcagagcag cggtctgtat    600

agcctgtcta gcgttgttac cgttccgagc agcagcctgg gcacccagac ctatatttgc    660

aatgtgaatc ataaaccgag caataccaaa gtggataaaa aagtggagcc taagagctgt    720

gacaaaactc acacaggtgg aggcgggtcc ggtggaggcg ggtccggggg accgtcagtc    780

ttcctcttcc ccccaaaacc caaggacacc ctcatgatct cccggacccc tgaggtcaca    840
```

tgcgtggtgg tggacgtgag ccacgaagac cctgaggtca agttcaactg gtacgtggac 900
ggcgtggagg tgcataatgc caagacaaag ccgcgggagg agcagtacaa cagcacgtac 960
cgtgtggtca gcgtcctcac cgtcctgcac caggactggc tgaatggcaa ggagtacaag 1020
tgcaaggtct ccaacaaagc cctcccagcc cccatcgaga aaaccatctc caaagccaaa 1080
gggcagcccc gagaaccaca ggtgtacacc ctgcccccat cccgggagga gatgaccaag 1140
aaccaggtca acctgacctg cctggtcaaa ggcttctatc ccagcgacat cgccgtggag 1200
tgggagagca atgggcagcc ggagaacaac tacaagacca cgcctcccgt gctggactcc 1260
gacggctcct tcttcctcaa cagcaccctc accgtggaca agagcaggtg gcagcagggg 1320
aacgtcttct catgctccgt gatgcatgag gctctgcaca accactacac gcagaagagc 1380
ctctccctgt ccccgggtgg tggcggctcc ggcggtggag ggtctggggg accgtcagtc 1440
ttcctcttcc ccccaaaacc caaggacacc ctcatgatct cccggacccc tgaggtcaca 1500
tgcgtggtgg tggacgtgag ccacgaagac cctgaggtca agttcaactg gtacgtggac 1560
ggcgtggagg tgcataatgc caagacaaag ccgcgggagg agcagtacaa cagcacgtac 1620
cgtgtggtca gcgtcctcac cgtcctgcac caggactggc tgaatggcaa ggagtacaag 1680
tgcaaggtct ccaacaaagc cctcccagcc cccatcgaga aaaccatctc caaagccaaa 1740
gggcagcccc gagaaccaca ggtgtacacc ctgcccccat cccgggagga gatgaccaag 1800
aaccaggtca acctgacctg cctggtcaaa ggcttctatc ccagcgacat cgccgtggag 1860
tgggagagca atgggcagcc ggagaacaac tacaagacca cgcctcccgt gctggactcc 1920
gacggctcct tcttcctcaa cagcaccctc accgtggaca agagcaggtg gcagcagggg 1980
aacgtcttct catgctccgt gatgcatgag gctctgcaca accactacac gcagaagagc 2040
ctctccctgt ccccgggtaa atga 2064

<210> SEQ ID NO 83
<211> LENGTH: 692
<212> TYPE: PRT
<213> ORGANISM: Artificial Sequence
<220> FEATURE:
<223> OTHER INFORMATION: Synthetic Construct

<400> SEQUENCE: 83

Met Gly Trp Ser Cys Ile Ile Leu Phe Leu Val Ala Thr Ala Thr Gly
1 5 10 15

Ala His Ser Glu Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Ser Asn Tyr Asp Met Tyr Trp Val Arg Gln Thr Thr Gly Lys Gly Leu
50 55 60

Glu Trp Val Ser Ala Ile Gly Thr Ala Gly Asp Thr Tyr Tyr Pro Gly
65 70 75 80

Ser Val Lys Gly Arg Phe Thr Ile Ser Arg Glu Asn Ala Lys Asn Ser
85 90 95

Leu Tyr Leu Gln Met Asn Ser Leu Arg Ala Gly Asp Thr Ala Val Tyr
100 105 110

Tyr Cys Ala Arg Glu Lys Ser Ser Thr Ser Ala Phe Asp Tyr Trp Gly
115 120 125

Gln Gly Thr Leu Val Thr Val Ser Ser Ala Ser Thr Lys Gly Pro Ser
130 135 140

-continued

```
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Gly Gly Gly Gly Ser Gly Gly Gly Gly Ser Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Asn
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Asn Ser Thr Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Gly Gly Ser Gly Gly Gly Gly Ser Gly Gly Gly Gly Ser
465                 470                 475                 480

Gly Gly Pro Ser Val Phe Leu Phe Pro Pro Lys Pro Lys Asp Thr Leu
                485                 490                 495

Met Ile Ser Arg Thr Pro Glu Val Thr Cys Val Val Val Asp Val Ser
            500                 505                 510

His Glu Asp Pro Glu Val Lys Phe Asn Trp Tyr Val Asp Gly Val Glu
        515                 520                 525

Val His Asn Ala Lys Thr Lys Pro Arg Glu Glu Gln Tyr Asn Ser Thr
    530                 535                 540

Tyr Arg Val Val Ser Val Leu Thr Val Leu His Gln Asp Trp Leu Asn
545                 550                 555                 560
```

-continued

```
Gly Lys Glu Tyr Lys Cys Lys Val Ser Asn Lys Ala Leu Pro Ala Pro
            565                 570                 575

Ile Glu Lys Thr Ile Ser Lys Ala Lys Gly Gln Pro Arg Glu Pro Gln
            580                 585                 590

Val Tyr Thr Leu Pro Pro Ser Arg Glu Glu Met Thr Lys Asn Gln Val
        595                 600                 605

Asn Leu Thr Cys Leu Val Lys Gly Phe Tyr Pro Ser Asp Ile Ala Val
    610                 615                 620

Glu Trp Glu Ser Asn Gly Gln Pro Glu Asn Asn Tyr Lys Thr Thr Pro
625                 630                 635                 640

Pro Val Leu Asp Ser Asp Gly Ser Phe Phe Leu Asn Ser Thr Leu Thr
            645                 650                 655

Val Asp Lys Ser Arg Trp Gln Gln Gly Asn Val Phe Ser Cys Ser Val
            660                 665                 670

Met His Glu Ala Leu His Asn His Tyr Thr Gln Lys Ser Leu Ser Leu
        675                 680                 685

Ser Pro Gly Lys
    690


<210> SEQ ID NO 84
<211> LENGTH: 2079
<212> TYPE: DNA
<213> ORGANISM: Artificial Sequence
<220> FEATURE:
<223> OTHER INFORMATION: Synthetic Construct

<400> SEQUENCE: 84

atgggatgga gctgtatcat cctcttcttg gtagcaacag ctacaggcgc gcactccgag      60

gtgcagctgg tggagtctgg gggaggcttg gtacagcctg gggggtccct gagactctcc     120

tgtgcagcct ctggattcac cttcagtaac tacgacatgt actgggtccg ccaaactaca     180

ggaaaaggtc tggagtgggt ctcagctatt ggtactgctg gtgacacata ctatccaggc     240

tccgtgaagg gccgattcac catctccaga gaaaatgcca agaactcctt gtatcttcaa     300

atgaacagcc tgagagccgg ggacacggct gtgtattact gtgcaagaga gaagtctagc     360

acctcggcct ttgactactg gggccaggga accctggtca ccgtctcctc agcctccacc     420

aagggcccga gcgtgtttcc gctggcaccg agcagcaaaa gcaccagcgg tggcacagca     480

gcactgggtt gtctggtgaa agattatttt ccggaaccgg ttacagttag ctggaatagc     540

ggtgccctga ccagcggtgt tcataccttt ccggcagttc tgcagagcag cggtctgtat     600

agcctgtcta gcgttgttac cgttccgagc agcagcctgg gcacccagac ctatatttgc     660

aatgtgaatc ataaaccgag caataccaaa gtggataaaa aagtggagcc taagagctgt     720

gacaaaactc acacaggtgg aggcgggtcc ggtggaggcg ggtccggggg accgtcagtc     780

ttcctcttcc ccccaaaacc caaggacacc ctcatgatct cccggacccc tgaggtcaca     840

tgcgtggtgg tggacgtgag ccacgaagac cctgaggtca agttcaactg gtacgtggac     900

ggcgtggagg tgcataatgc caagacaaag ccgcgggagg agcagtacaa cagcacgtac     960

cgtgtggtca gcgtcctcac cgtcctgcac caggactggc tgaatggcaa ggagtacaag    1020

tgcaaggtct ccaacaaagc cctcccagcc cccatcgaga aaaccatctc caaagccaaa    1080

gggcagcccc gagaaccaca ggtgtacacc ctgcccccat cccgggagga gatgaccaag    1140

aaccaggtca acctgacctg cctggtcaaa ggcttctatc ccagcgacat cgccgtggag    1200

tgggagagca atgggcagcc ggagaacaac tacaagacca cgcctcccgt gctggactcc    1260
```

```
gacggctcct tcttcctcaa cagcaccctc accgtggaca agagcaggtg gcagcagggg   1320

aacgtcttct catgctccgt gatgcatgag gctctgcaca accactacac gcagaagagc   1380

ctctccctgt ccccgggtgg tggcggctcc ggaggtggcg gaagcggcgg tggagggtct   1440

gggggaccgt cagtcttcct cttcccccca aaacccaagg acaccctcat gatctcccgg   1500

acccctgagg tcacatgcgt ggtggtggac gtgagccacg aagaccctga ggtcaagttc   1560

aactggtacg tggacggcgt ggaggtgcat aatgccaaga caaagccgcg ggaggagcag   1620

tacaacagca cgtaccgtgt ggtcagcgtc ctcaccgtcc tgcaccagga ctggctgaat   1680

ggcaaggagt acaagtgcaa ggtctccaac aaagccctcc cagcccccat cgagaaaacc   1740

atctccaaag ccaaagggca gccccgagaa ccacaggtgt acaccctgcc cccatcccgg   1800

gaggagatga ccaagaacca ggtcaacctg acctgcctgg tcaaaggctt ctatcccagc   1860

gacatcgccg tggagtggga gagcaatggg cagccggaga acaactacaa gaccacgcct   1920

cccgtgctgg actccgacgg ctccttcttc ctcaacagca ccctcaccgt ggacaagagc   1980

aggtggcagc aggggaacgt cttctcatgc tccgtgatgc atgaggctct gcacaaccac   2040

tacacgcaga agagcctctc cctgtccccg ggtaaatga                          2079
```

<210> SEQ ID NO 85
<211> LENGTH: 697
<212> TYPE: PRT
<213> ORGANISM: Artificial Sequence
<220> FEATURE:
<223> OTHER INFORMATION: Synthetic Construct

<400> SEQUENCE: 85

```
Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Asp Met Tyr Trp Val Arg Gln Thr Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Glu Lys Ser Ser Thr Ser Ala Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220
```

-continued

```
Lys Pro Ser Asn Thr Lys Val Asp Lys Lys Val Glu Pro Lys Ser Cys
225                 230                 235                 240

Asp Lys Thr His Thr Gly Gly Gly Gly Ser Gly Gly Gly Gly Ser Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Asn
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Asn Ser Thr Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Gly Gly Ser Gly Gly Gly Gly Ser Gly Gly Gly Gly Ser
465                 470                 475                 480

Gly Gly Gly Gly Ser Gly Gly Pro Ser Val Phe Leu Phe Pro Pro Lys
                485                 490                 495

Pro Lys Asp Thr Leu Met Ile Ser Arg Thr Pro Glu Val Thr Cys Val
            500                 505                 510

Val Val Asp Val Ser His Glu Asp Pro Glu Val Lys Phe Asn Trp Tyr
        515                 520                 525

Val Asp Gly Val Glu Val His Asn Ala Lys Thr Lys Pro Arg Glu Glu
    530                 535                 540

Gln Tyr Asn Ser Thr Tyr Arg Val Val Ser Val Leu Thr Val Leu His
545                 550                 555                 560

Gln Asp Trp Leu Asn Gly Lys Glu Tyr Lys Cys Lys Val Ser Asn Lys
                565                 570                 575

Ala Leu Pro Ala Pro Ile Glu Lys Thr Ile Ser Lys Ala Lys Gly Gln
            580                 585                 590

Pro Arg Glu Pro Gln Val Tyr Thr Leu Pro Pro Ser Arg Glu Glu Met
        595                 600                 605

Thr Lys Asn Gln Val Asn Leu Thr Cys Leu Val Lys Gly Phe Tyr Pro
    610                 615                 620

Ser Asp Ile Ala Val Glu Trp Glu Ser Asn Gly Gln Pro Glu Asn Asn
625                 630                 635                 640
```

```
Tyr Lys Thr Thr Pro Pro Val Leu Asp Ser Asp Gly Ser Phe Phe Leu
                645                 650                 655

Asn Ser Thr Leu Thr Val Asp Lys Ser Arg Trp Gln Gln Gly Asn Val
            660                 665                 670

Phe Ser Cys Ser Val Met His Glu Ala Leu His Asn His Tyr Thr Gln
        675                 680                 685

Lys Ser Leu Ser Leu Ser Pro Gly Lys
    690                 695


<210> SEQ ID NO 86
<211> LENGTH: 2094
<212> TYPE: DNA
<213> ORGANISM: Artificial Sequence
<220> FEATURE:
<223> OTHER INFORMATION: Synthetic Construct

<400> SEQUENCE: 86

atgggatgga gctgtatcat cctcttcttg gtagcaacag ctacaggcgc gcactccgag     60

gtgcagctgg tggagtctgg gggaggcttg gtacagcctg gggggtccct gagactctcc    120

tgtgcagcct ctggattcac cttcagtaac tacgacatgt actgggtccg ccaaactaca    180

ggaaaaggtc tggagtgggt ctcagctatt ggtactgctg gtgacacata ctatccaggc    240

tccgtgaagg gccgattcac catctccaga gaaaatgcca agaactcctt gtatcttcaa    300

atgaacagcc tgagagccgg ggacacggct gtgtattact gtgcaagaga gaagtctagc    360

acctcggcct ttgactactg gggccaggga accctggtca ccgtctcctc agcctccacc    420

aagggcccga gcgtgtttcc gctggcaccg agcagcaaaa gcaccagcgg tggcacagca    480

gcactgggtt gtctggtgaa agattatttt ccggaaccgg ttacagttag ctggaatagc    540

ggtgccctga ccagcggtgt tcataccttt ccggcagttc tgcagagcag cggtctgtat    600

agcctgtcta gcgttgttac cgttccgagc agcagcctgg gcacccagac ctatatttgc    660

aatgtgaatc ataaaccgag caataccaaa gtggataaaa aagtggagcc taagagctgt    720

gacaaaactc acacaggtgg aggcgggtcc ggtggaggcg ggtccggggg accgtcagtc    780

ttcctcttcc ccccaaaacc caaggacacc ctcatgatct cccggacccc tgaggtcaca    840

tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggagga gatgaccaag   1140

aaccaggtca acctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcaa cagcaccctc accgtggaca agagcaggtg gcagcagggg   1320

aacgtcttct catgctccgt gatgcatgag gctctgcaca accactacac gcagaagagc   1380

ctctccctgt ccccgggtgg tggcggctcc ggaggtggcg gaagcggcgg tggagggtct   1440

ggtggaggag ggtcaggggg accgtcagtc ttcctcttcc ccccaaaacc caaggacacc   1500

ctcatgatct cccggacccc tgaggtcaca tgcgtggtgg tggacgtgag ccacgaagac   1560

cctgaggtca agttcaactg gtacgtggac ggcgtggagg tgcataatgc caagacaaag   1620

ccgcgggagg agcagtacaa cagcacgtac cgtgtggtca gcgtcctcac cgtcctgcac   1680

caggactggc tgaatggcaa ggagtacaag tgcaaggtct ccaacaaagc cctcccagcc   1740
```

-continued

```
cccatcgaga aaaccatctc caaagccaaa gggcagcccc gagaaccaca ggtgtacacc   1800

ctgcccccat cccgggagga gatgaccaag aaccaggtca acctgacctg cctggtcaaa   1860

ggcttctatc ccagcgacat cgccgtggag tgggagagca atgggcagcc ggagaacaac   1920

tacaagacca cgcctcccgt gctggactcc gacggctcct tcttcctcaa cagcaccctc   1980

accgtggaca agagcaggtg gcagcagggg aacgtcttct catgctccgt gatgcatgag   2040

gctctgcaca accactacac gcagaagagc ctctccctgt ccccgggtaa atga         2094
```

<210> SEQ ID NO 87
<211> LENGTH: 702
<212> TYPE: PRT
<213> ORGANISM: Artificial Sequence
<220> FEATURE:
<223> OTHER INFORMATION: Synthetic Construct

<400> SEQUENCE: 87

```
Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Asp Met Tyr Trp Val Arg Gln Thr Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Glu Lys Ser Ser Thr Ser Ala Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Gly Gly Gly Gly Ser Gly Gly Gly Gly Ser Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300
```

```
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Asn
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Asn Ser Thr Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Gly Gly Ser Gly Gly Gly Gly Ser Gly Gly Gly Gly Ser
465                 470                 475                 480

Gly Gly Gly Gly Ser Gly Gly Gly Gly Ser Gly Gly Pro Ser Val Phe
                485                 490                 495

Leu Phe Pro Pro Lys Pro Lys Asp Thr Leu Met Ile Ser Arg Thr Pro
            500                 505                 510

Glu Val Thr Cys Val Val Val Asp Val Ser His Glu Asp Pro Glu Val
        515                 520                 525

Lys Phe Asn Trp Tyr Val Asp Gly Val Glu Val His Asn Ala Lys Thr
    530                 535                 540

Lys Pro Arg Glu Glu Gln Tyr Asn Ser Thr Tyr Arg Val Val Ser Val
545                 550                 555                 560

Leu Thr Val Leu His Gln Asp Trp Leu Asn Gly Lys Glu Tyr Lys Cys
                565                 570                 575

Lys Val Ser Asn Lys Ala Leu Pro Ala Pro Ile Glu Lys Thr Ile Ser
            580                 585                 590

Lys Ala Lys Gly Gln Pro Arg Glu Pro Gln Val Tyr Thr Leu Pro Pro
        595                 600                 605

Ser Arg Glu Glu Met Thr Lys Asn Gln Val Asn Leu Thr Cys Leu Val
    610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
                645                 650                 655

Gly Ser Phe Phe Leu Asn Ser Thr Leu Thr Val Asp Lys Ser Arg Trp
            660                 665                 670

Gln Gln Gly Asn Val Phe Ser Cys Ser Val Met His Glu Ala Leu His
        675                 680                 685

Asn His Tyr Thr Gln Lys Ser Leu Ser Leu Ser Pro Gly Lys
    690                 695                 700
```

<210> SEQ ID NO 88
<211> LENGTH: 2109

<212> TYPE: DNA
<213> ORGANISM: Artificial Sequence
<220> FEATURE:
<223> OTHER INFORMATION: Synthetic Construct

<400> SEQUENCE: 88
atgggatgga gctgtatcat cctcttcttg gtagcaacag ctacaggcgc gcactccgag 60
gtgcagctgg tggagtctgg gggaggcttg gtacagcctg gggggtccct gagactctcc 120
tgtgcagcct ctggattcac cttcagtaac tacgacatgt actgggtccg ccaaactaca 180
ggaaaaggtc tggagtgggt ctcagctatt ggtactgctg gtgacacata ctatccaggc 240
tccgtgaagg gccgattcac catctccaga gaaaatgcca agaactcctt gtatcttcaa 300
atgaacagcc tgagagccgg ggacacggct gtgtattact gtgcaagaga gaagtctagc 360
acctcggcct ttgactactg gggccaggga accctggtca ccgtctcctc agcctccacc 420
aagggcccga gcgtgtttcc gctggcaccg agcagcaaaa gcaccagcgg tggcacagca 480
gcactgggtt gtctggtgaa agattatttt ccggaaccgg ttacagttag ctggaatagc 540
ggtgccctga ccagcggtgt tcataccttt ccggcagttc tgcagagcag cggtctgtat 600
agcctgtcta gcgttgttac cgttccgagc agcagcctgg gcacccagac ctatatttgc 660
aatgtgaatc ataaaccgag caataccaaa gtggataaaa aagtggagcc taagagctgt 720
gacaaaactc acacaggtgg aggcgggtcc ggtggaggcg ggtccggggg accgtcagtc 780
ttcctcttcc ccccaaaacc caaggacacc ctcatgatct cccggacccc tgaggtcaca 840
tgcgtggtgg tggacgtgag ccacgaagac cctgaggtca agttcaactg gtacgtggac 900
ggcgtggagg tgcataatgc caagacaaag ccgcgggagg agcagtacaa cagcacgtac 960
cgtgtggtca gcgtcctcac cgtcctgcac caggactggc tgaatggcaa ggagtacaag 1020
tgcaaggtct ccaacaaagc cctcccagcc cccatcgaga aaaccatctc caaagccaaa 1080
gggcagcccc gagaaccaca ggtgtacacc ctgcccccat cccgggagga gatgaccaag 1140
aaccaggtca acctgacctg cctggtcaaa ggcttctatc ccagcgacat cgccgtggag 1200
tgggagagca atgggcagcc ggagaacaac tacaagacca cgcctcccgt gctggactcc 1260
gacggctcct tcttcctcaa cagcaccctc accgtggaca agagcaggtg gcagcagggg 1320
aacgtcttct catgctccgt gatgcatgag gctctgcaca accactacac gcagaagagc 1380
ctctccctgt ccccgggtgg tggcggctcc ggaggcggag gctccggagg tggcggaagc 1440
ggcggtggag ggtctggtgg aggagggtca gggggaccgt cagtcttcct cttcccccca 1500
aaacccaagg acaccctcat gatctcccgg acccctgagg tcacatgcgt ggtggtggac 1560
gtgagccacg aagaccctga ggtcaagttc aactggtacg tggacggcgt ggaggtgcat 1620
aatgccaaga caaagccgcg ggaggagcag tacaacagca cgtaccgtgt ggtcagcgtc 1680
ctcaccgtcc tgcaccagga ctggctgaat ggcaaggagt acaagtgcaa ggtctccaac 1740
aaagccctcc cagcccccat cgagaaaacc atctccaaag ccaaagggca gccccgagaa 1800
ccacaggtgt acaccctgcc cccatcccgg gaggagatga ccaagaacca ggtcaacctg 1860
acctgcctgg tcaaaggctt ctatcccagc gacatcgccg tggagtggga gagcaatggg 1920
cagccggaga acaactacaa gaccacgcct cccgtgctgg actccgacgg ctccttcttc 1980
ctcaacagca ccctcaccgt ggacaagagc aggtggcagc aggggaacgt cttctcatgc 2040
tccgtgatgc atgaggctct gcacaaccac tacacgcaga agagcctctc cctgtccccg 2100
ggtaaatga 2109

-continued

```
<210> SEQ ID NO 89
<211> LENGTH: 5
<212> TYPE: PRT
<213> ORGANISM: Artificial Sequence
<220> FEATURE:
<223> OTHER INFORMATION: Synthetic Construct

<400> SEQUENCE: 89

Gly Gly Gly Gly Ser
1               5


<210> SEQ ID NO 90
<211> LENGTH: 10
<212> TYPE: PRT
<213> ORGANISM: Artificial Sequence
<220> FEATURE:
<223> OTHER INFORMATION: Synthetic Construct

<400> SEQUENCE: 90

Gly Gly Gly Gly Ser Gly Gly Gly Gly Ser
1               5                   10


<210> SEQ ID NO 91
<211> LENGTH: 15
<212> TYPE: PRT
<213> ORGANISM: Artificial Sequence
<220> FEATURE:
<223> OTHER INFORMATION: Synthetic Construct

<400> SEQUENCE: 91

Gly Gly Gly Gly Ser Gly Gly Gly Gly Ser Gly Gly Gly Gly Ser
1               5                   10                  15


<210> SEQ ID NO 92
<211> LENGTH: 20
<212> TYPE: PRT
<213> ORGANISM: Artificial Sequence
<220> FEATURE:
<223> OTHER INFORMATION: Synthetic Construct

<400> SEQUENCE: 92

Gly Gly Gly Gly Ser Gly Gly Gly Gly Ser Gly Gly Gly Gly Ser Gly
1               5                   10                  15

Gly Gly Gly Ser
            20


<210> SEQ ID NO 93
<211> LENGTH: 25
<212> TYPE: PRT
<213> ORGANISM: Artificial Sequence
<220> FEATURE:
<223> OTHER INFORMATION: Synthetic Construct

<400> SEQUENCE: 93

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```